United States Patent
Koskelainen et al.

(10) Patent No.: US 7,425,568 B2
(45) Date of Patent: *Sep. 16, 2008

(54) COMPOUNDS, WHICH ARE POTENT INHIBITORS OF $NA^+/CA^{2+}$ EXCHANGE MECHANISM AND ARE USEFUL IN THE TREATMENT OF ARRHYTHMIAS

(75) Inventors: Tuula Koskelainen, Lohja as (FI); Leena Otsomaa, Espoo (FI); Arto Karjalainen, Espoo (FI); Pekka Kotovuori, Vantaa (FI); Jukka Tenhunen, Klaukkala (FI); Sirpa Rasku, Helsinki (FI); Pentti Nore, Helsinki (FI); Eija Tiainen, Espoo (FI); Olli Törmäkangas, Turku (FI)

(73) Assignee: Orion Corporation, Espoo (FI)

( * ) Notice: Subject to any disclaimer, the term of this patent is extended or adjusted under 35 U.S.C. 154(b) by 438 days.

This patent is subject to a terminal disclaimer.

(21) Appl. No.: 10/482,396

(22) PCT Filed: Jul. 10, 2002

(86) PCT No.: PCT/FI02/00621

§ 371 (c)(1),
(2), (4) Date: Jun. 8, 2004

(87) PCT Pub. No.: WO03/006452

PCT Pub. Date: Jan. 23, 2003

(65) Prior Publication Data
US 2004/0235905 A1 Nov. 25, 2004

(30) Foreign Application Priority Data
Jul. 10, 2001 (FI) ................................. 20011507

(51) Int. Cl.
*A61K 31/4433* (2006.01)
*C07D 405/12* (2006.01)
(52) U.S. Cl. .................................. 514/337; 546/282.7
(58) Field of Classification Search .............. 546/282.7; 514/337
See application file for complete search history.

(56) References Cited

U.S. PATENT DOCUMENTS

| 2,820,817 | A |   | 1/1958 | Sam |
| 3,862,232 | A | * | 1/1975 | Lednicer ............ 564/338 |
| 5,703,118 | A |   | 12/1997 | Durand et al. |
| 6,177,449 | B1 |   | 1/2001 | Brendel et al. |
| 2006/0241147 | A1 |   | 10/2006 | Otsomaa et al. |

FOREIGN PATENT DOCUMENTS

| EP | 0 978 506 A1 | 2/2000 |
| EP | 1 031 556 A1 | 8/2000 |
| GB | 1068751 | 5/1967 |
| GB | 1154119 | 6/1969 |
| JP | 9-67336 | 3/1997 |
| JP | 09067336 A2 | 3/1997 |
| JP | 11049752 A2 | 2/1999 |
| JP | 11302235 A2 | 11/1999 |
| WO | WO 00/64445 | 11/2000 |
| WO | WO 01/21610 A1 | 3/2001 |

OTHER PUBLICATIONS

Spido et al., "Sodium Calcium Exchange as a Target, etc.,", Handbook of Experimental Pharmacology, NY: Springer-Verlag, 2006 (171) 159-199.*
Noble, "Simulation of Na/Ca Exchange, etc.," Ann. N.Y. Acad. Sci. 976:431-437 (2002).*
Sipido et al. "Altered Na/Ca exchange activity, etc.," Cardiovascular Research 53 (2002) 782-805.*
Patent Abstracts of Japan, vol. 200, No. 2, Feb. 29, 2000 and JP 11 302235 A (Taisho Pharmaceut Co LTD), Nov. 2, 1999 (Abstract).
Patent Abstracts of Japan, vol. 199, No. 905, May 31, 1999 & JP 11 049752 A (Taisho Pharmaceut Co LTD), Feb. 23, 1999 (Abstract).
Database WPI: Week 199718, Derwent Publications Ltd., JP 9067336.

* cited by examiner

*Primary Examiner*—Patricia L Morris
(74) *Attorney, Agent, or Firm*—Finnegan, Henderson, Farabow, Garrett & Dunner, LLP

(57) ABSTRACT

Therapeutically active compounds of formula (I):

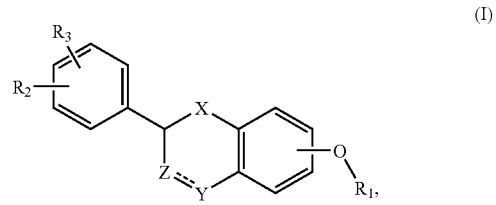

wherein the variables shown in formula (I) are defined in the disclosure; and pharmaceutically acceptable salts and esters thereof. The compounds are potent inhibitors of the $Na^+/Ca^{2+}$ exchange mechanism.

9 Claims, 1 Drawing Sheet

COMPOUNDS, WHICH ARE POTENT INHIBITORS OF NA+/CA2+ EXCHANGE MECHANISM AND ARE USEFUL IN THE TREATMENT OF ARRHYTHMIAS

This application is a U.S. national stage filing of PCT International application Ser. No. PCT/FI02/00621, filed on Jul. 10, 2002, which claims the benefit of priority to Finnish patent application no. 20011507, filed on Jul. 10, 2001.

TECHNICAL FIELD

The present invention relates to new therapeutically active compounds and pharmaceutically acceptable salts and esters thereof. The invention also relates to pharmaceutical compositions containing these compounds as active ingredients. The compounds of the invention are potent inhibitors of $Na^+/Ca^{2+}$ exchange mechanism.

BACKGROUND OF THE INVENTION $Na^+/Ca^{2+}$ exchange mechanism is one of the ion transport mechanisms that regulate the concentration of sodium and calcium ions in the cells. Compounds which selectively inhibit $Na^+/Ca^{2+}$ exchange mechanism and thereby prevent overload of $Ca^{2+}$ in cells are regarded useful in preventing the cell injury mechanism of cardiac muscle and the like after ischemia and reperfusion. Such compounds are useful in the treatment of ischemic heart diseases, ischemic cerebral diseases, ischemic renal diseases and in the protection of cells during thrombolytic therapy, angioplasty, bypass operation of coronary artery or organ transplantation and arrhythmias.

Compounds capable of inhibiting $Na^+/Ca^{2+}$ exchange system have been described earlier e.g. in patent publications WO 97/09306, EP 0978506, EP 1031556, JP 11049752 and JP 11302235.

SUMMARY OF THE INVENTION

It has now been found that compounds of formula (I) are particularly potent inhibitors of $Na^+/Ca^{2+}$ exchange mechanism and are particularly useful in the treatment of arrhythmias.

The compounds of the present invention have a structure represented by formula (I):

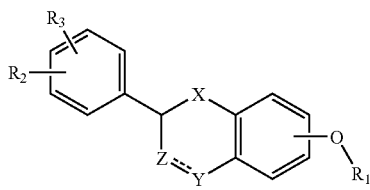

(I)

wherein
X is —O—, —CH$_2$— or —C(O)—;
Z is —CHR$_9$— or valence bond;
Y is —CH$_2$—, —C(O)—, CH(OR$_{10}$)—, —CH(NR$_{11}$R$_{12}$)—, —O—, —S—, —S(O)— or —S(O$_2$)—
provided that in case Z is a valence bond, Y is not C(O);
the dashed line represents an optional double bond in which case Z is —CR$_9$— and Y is —CH—, C(OR$_{10}$)— or —C(NR$_{11}$R$_{12}$)—;

R$_1$ is —(CH$_2$)$_n$NR$_4$R$_7$ or one of the following groups:

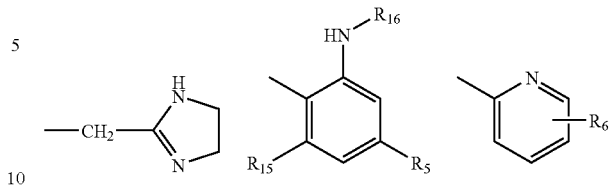

n is 1-4,
R$_2$ and R$_3$ are independently H, lower alkyl, lower alkoxy, —NO$_2$, halogen, —CF$_3$, —OH, —NHR$_8$ or —COOH,
R$_4$ and R$_7$ are independently H, lower alkyl or lower hydroxyalkyl,
R$_5$ is H, lower alkoxy, —CF$_3$, —NH$_2$ or —CN,
R$_6$ is —NO$_2$, —NR$_{14}$R$_{19}$, —CF$_3$ or

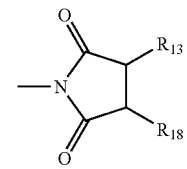

R$_8$ and R$_{16}$ are independently H or acyl,
R$_9$ is H or lower alkyl,
R$_{10}$ is H, alkylsulfonyl or acyl;
R$_{11}$ and R$_{12}$ are independently H, lower alkyl or acyl,
R$_{13}$ and R$_{18}$ are independently H or —OR$_{20}$,
R$_{14}$ and R$_{19}$ are independently H, acyl, alkylsulfonyl, C(S)NHR$_{17}$ or C(O)NHR$_{17}$,
R$_{15}$ is H or NH$_2$,
R$_{17}$ is H or lower alkyl,
R$_{20}$ is H or acyl,
and pharmaceutically acceptable salts and esters thereof.

In one class of preferred compounds and pharmaceutically acceptable salts and esters thereof are compounds of formula

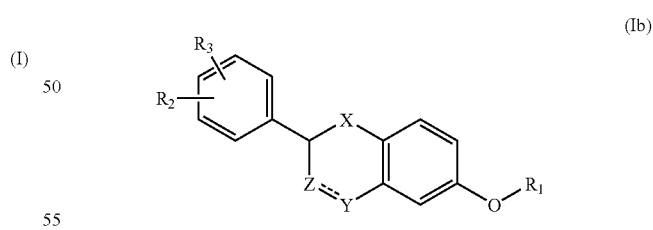

(Ib)

wherein R$_1$, R$_2$, R$_3$, X, Y and Z are as defined above. In another class of preferred compounds and pharmaceutically acceptable salts and esters thereof are compounds of formula (I), wherein X is O, and Z and Y is —CH$_2$—. In another class of preferred compounds and pharmaceutically acceptable salts and esters thereof are compounds of formula (I), wherein X is O, and Z is —CH$_2$— and Y is CHOH.

In one subclass of preferred compounds and pharmaceutically acceptable salts and esters thereof are compounds of formula (I) wherein R$_1$ is one of the following groups

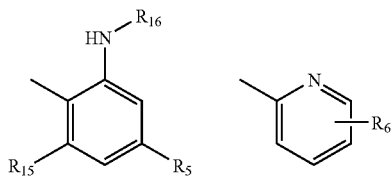

In another subclass of preferred compounds are compounds, wherein $R_6$ is —$NO_2$ or —$NR_{14}R_{19}$. In a group of this subclass R14 and R19 are independently H, acyl or alkylsulfonyl, $R_{15}$ and $R_{16}$ is preferably H and $R_5$ is H or lower alkoxy.

In one subclass of preferred compounds are compounds, wherein $R_2$ and $R_3$ are independently H or halogen. Fluorine is the preferred halogen.

In one class of preferred compounds are compounds wherein n=2. $R_4$ and $R_7$ are preferably methyl.

The present invention also provides a pharmaceutical composition comprising a compound of formula (I) together with a pharmaceutically acceptable carrier.

The present invention further provides a method for inhibiting $Na^+/Ca^{2+}$ exchange mechanism in a cell, comprising administering to a subject in need thereof a therapeutically effective amount of a compound of formula (I).

The present invention further provides a method for preventing overload of $Ca^{2+}$ ions in cells, comprising administering to a subject in need thereof a therapeutically effective amount of a compound of formula (I).

The present invention further provides a method for treating arrhythmias, comprising administering to a subject in need thereof a therapeutically effective amount of a compound of formula (I).

DETAILED DESCRIPTION OF THE INVENTION

Figure 1:
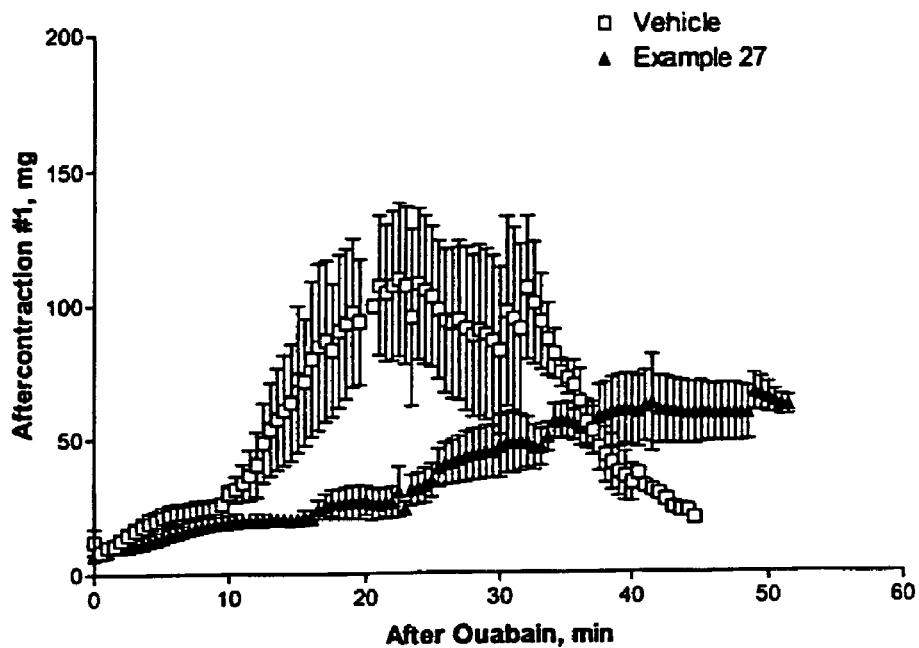
FIG. 1 shows the antiarrhythmic effects of the compound of Example 27 on ouabain-induced aftercontractions in guinea-pig isolated papillary muscles.

The compounds of the invention can be prepared from corresponding phenol derivatives (II), wherein $R_2$, $R_3$, X, Z and Y are the same as defined above.

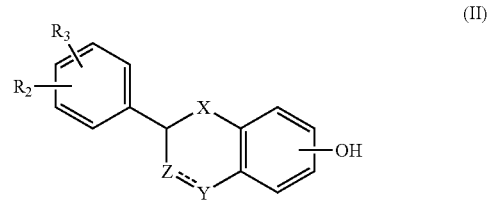

The syntheses are shown in Scheme 1, wherein formula (II) is abbreviated as Ar—OH (II), and $R_4$, $R_5$, $R_6$, $R_7$, $R_{15}$ and $R_{16}$ are the same as defined above, and Hal means halogen.

Compounds of formula (II) can be reacted with 1-chloro-2-nitrobenzene derivatives to result in nitrophenoxy compounds (10), which in turn by hydrogenation gives phenylamine derivatives (11). 5-Nitropyridin-2-yloxy derivatives (12) are obtained by reactions with 2-chloro-5-nitropyridine.

2-Oxymethyl imidazoline derivatives (14) can be synthesised from phenol derivatives (II) via cyano methyl ether (13), which is converted to imidazoline (14) by a known method (e.g. J. Med. Chem. 1994, 37(12), 1874). Alkoxyazide derivatives (16) are obtained via corresponding haloalkoxy derivatives (15) by reaction with sodium azide. Azides (16) are converted to amines (17) by reaction with triphenylamine. 2-(Dimethylamino)ethoxy derivatives (18) are obtained by direct reactions of phenols of formula (II) with 2-(dimethylamino)ethyl chloride.

The reduction of nitropyridines (22) followed by acylation, mesylation etc. produces compounds of formula (24), as shown by Scheme 2.

SCHEME 1

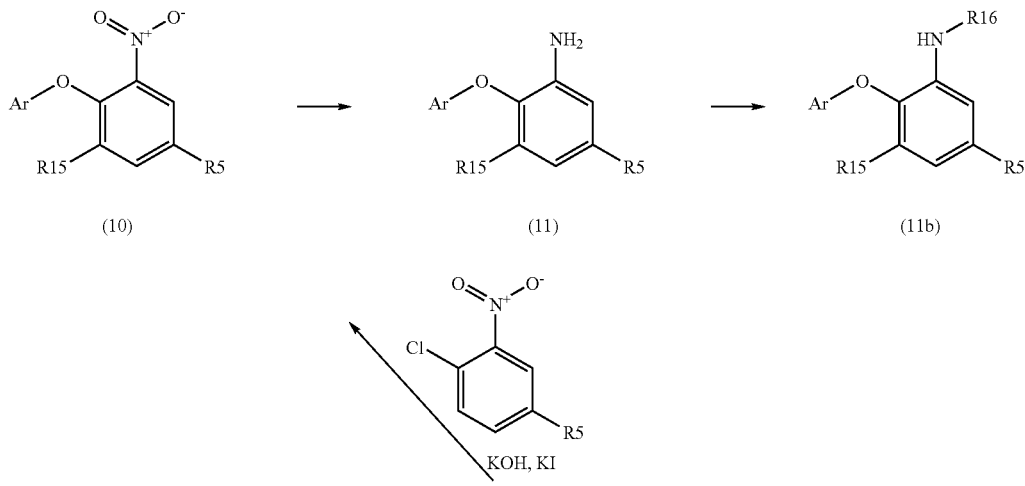

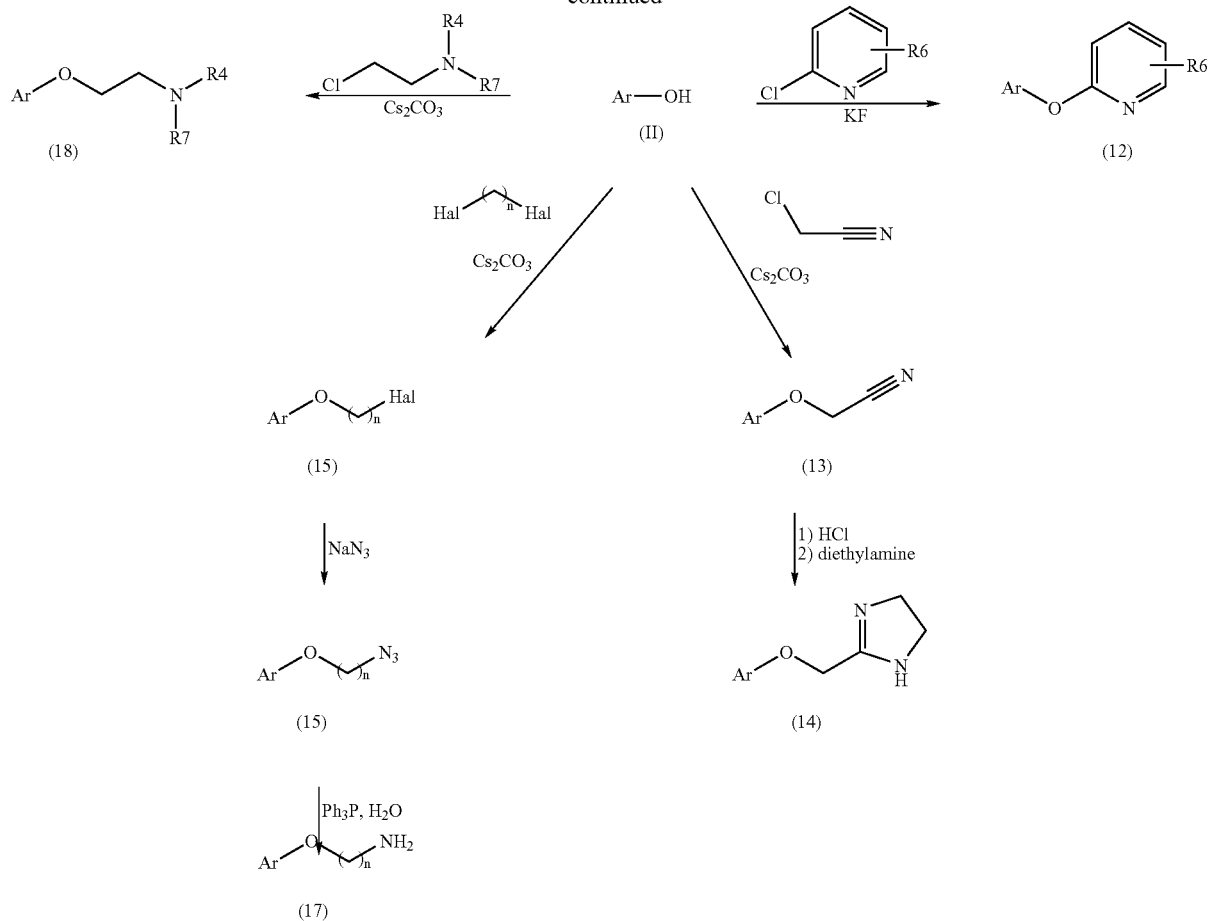
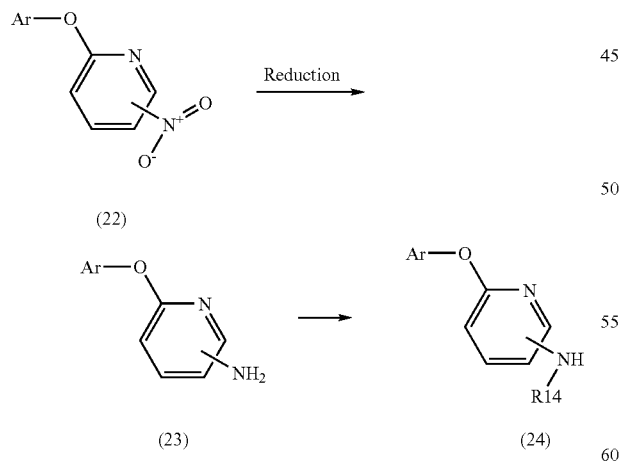
ods described in the literature, e.g. *J. Org Chem.*, 1960, 25, 1247-9 and *J. Org. Chem.*, 1958, 23, 1159-61 or as described later in Scheme 5.
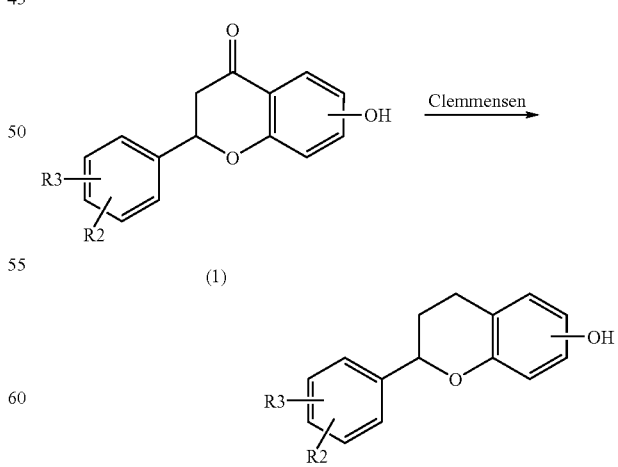
As shown in the following Scheme 3, wherein $R_2$ and $R_3$ are the same as defined above, 6- and 7-hydroxyflavane derivatives (2) are obtained from corresponding flavanones (1) by Clemmensen reduction. 6- and 7-hydroxyflavanones (1) are commercially available or can be synthesised by meth- The following Scheme 4, wherein $R_2$ and $R_3$ are the same as defined above, describes the synthesis of 2-phenyl indan-5-ols (9). Condensation of p-anisaldehyde (3) with substituted phenyl acetic acid (4) gives mixture of cis- and trans-isomers of the corresponding acrylic acid (5). After hydrogenation and intramolecular Friedel-Crafts reaction carbonyl functionality of 1-indanones (7) can be reduced by Clemmensen reduction. Finally methoxy indane (8) is refluxed in concentrated hydrobromic acid to obtain 2-phenyl indan-5-ols (9).

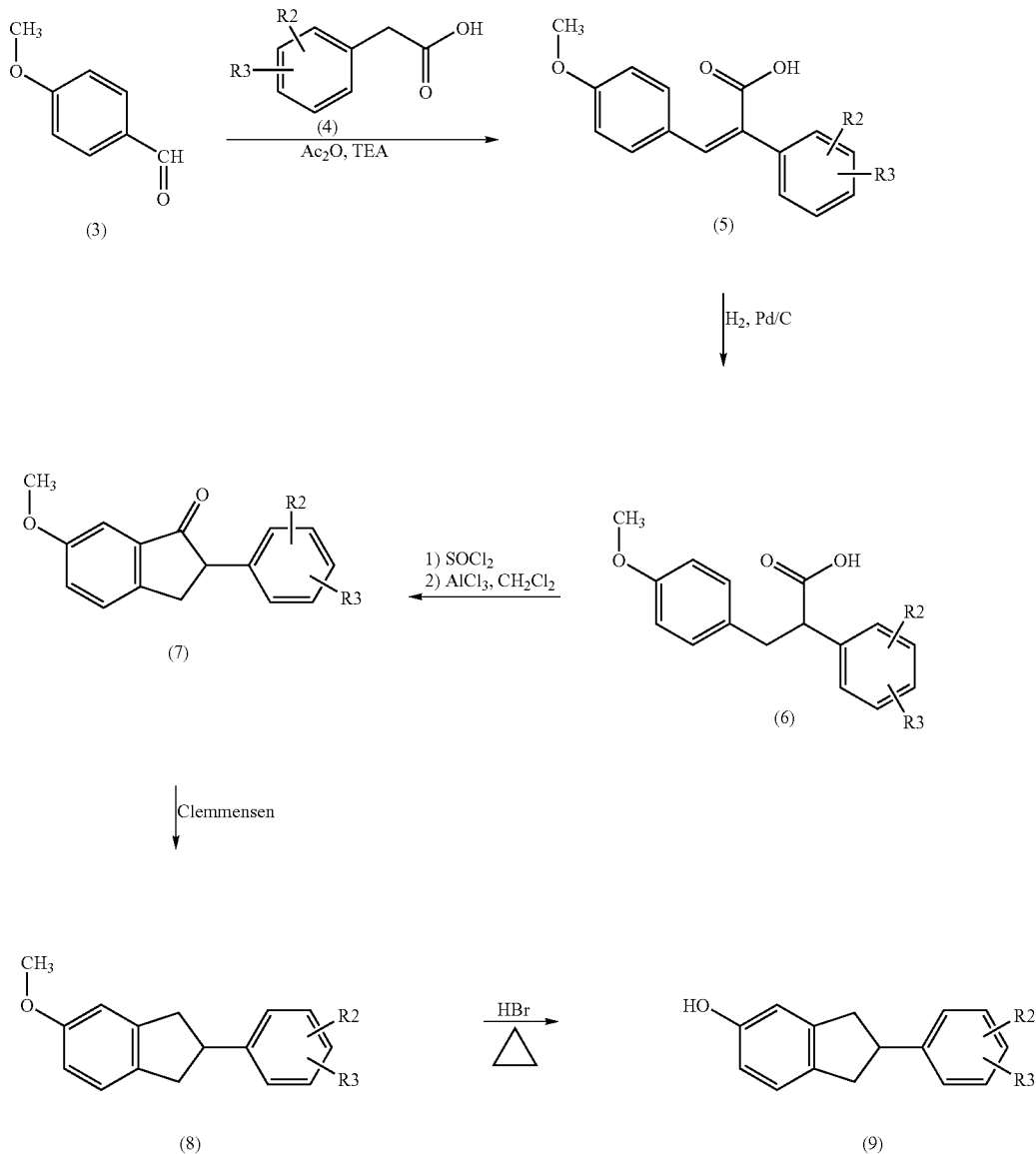

6-Hydroxyflavanone derivatives can be synthesised as shown in Scheme 5. 2',5'-Dihydroxyacetophenone or corresponding propiophenone is condensed with appropriate benzaldehyde resulting in a mixture of desired 6-hydroxyflavanone (36) and the corresponding chalcone (35). The chalcone can be cyclised to flavanone.

SCHEME 5

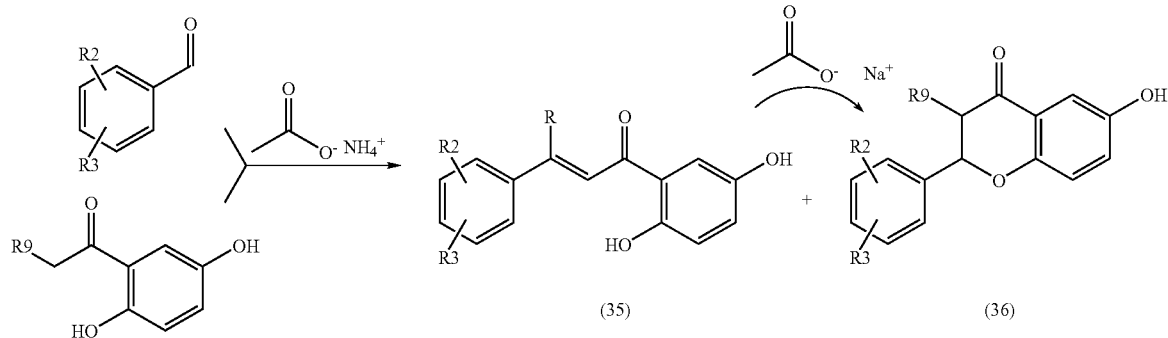

(35)   (36)

2-Phenylchroman-4,6-diol derivatives (37) are obtained from corresponding 6-hydroxyflavanones (36) by reduction as shown in Scheme 6. These diol derivatives can be reduced further into 6-hydroxyflavanes (38).

SCHEME 6

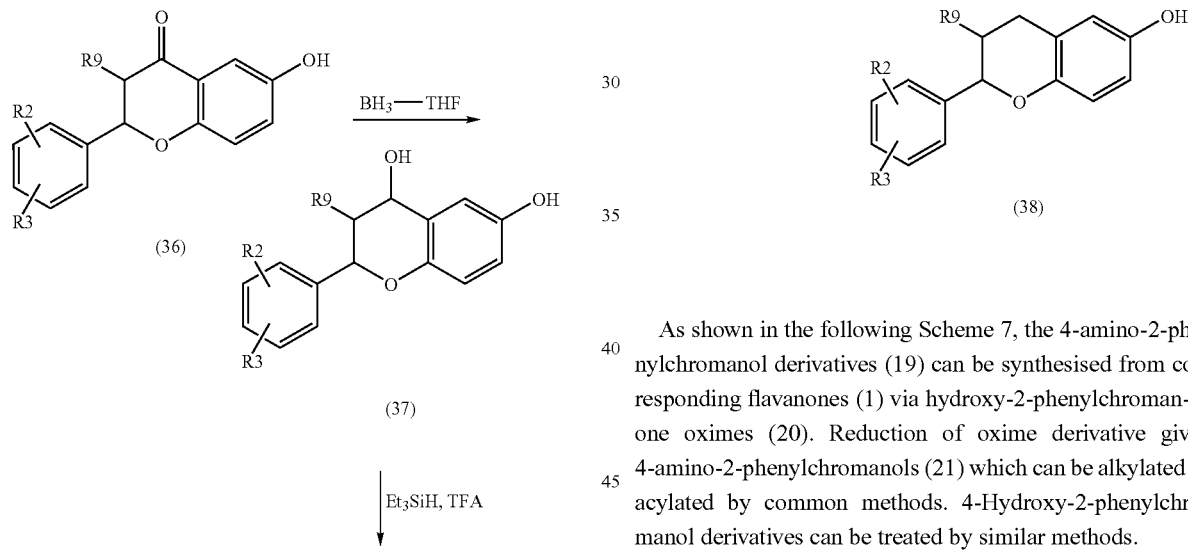

-continued (38)

As shown in the following Scheme 7, the 4-amino-2-phenylchromanol derivatives (19) can be synthesised from corresponding flavanones (1) via hydroxy-2-phenylchroman-4-one oximes (20). Reduction of oxime derivative gives 4-amino-2-phenylchromanols (21) which can be alkylated or acylated by common methods. 4-Hydroxy-2-phenylchromanol derivatives can be treated by similar methods.

SCHEME 7

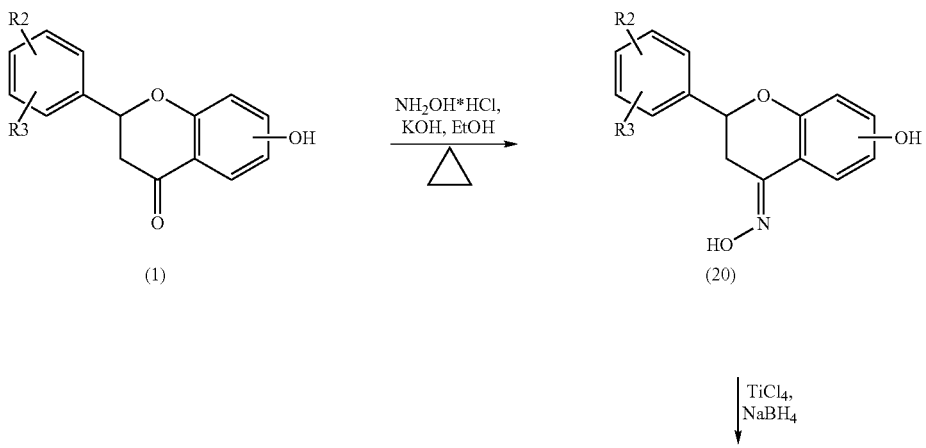

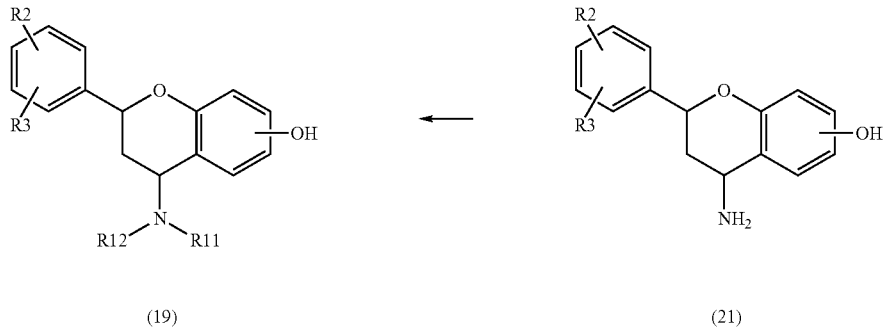

The following Scheme 8, wherein $R_2$ and $R_3$ are the same as defined above, describes the synthesis of 7-hydroxyisoflavones (29) and 7-hydroxyisoflavans (30). Acylation of 3-methoxyphenol with substituted phenyl acetic acids gives the corresponding 2-hydroxydeoxybenzoins (27) which can be cyclised with triethylortoformate to yield isoflavones (28). Deprotection with hydrobromic acid and catalytic hydrogenation gives 7-hydroxyisoflavans (30).

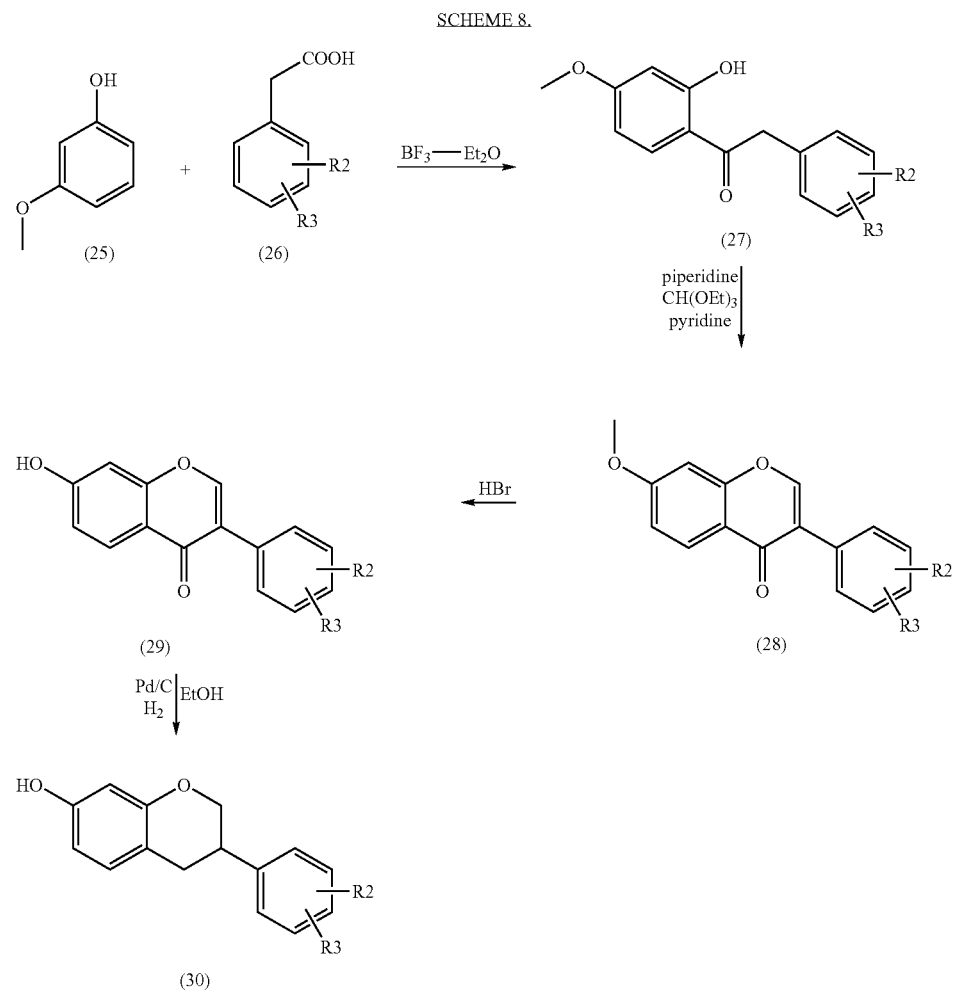

The following Scheme 9 describes the synthesis of 2-phenyl-2,3-dihydro-enzo[1,4]oxathiin-6-ol (34). The reaction of 2-mercaptobenzene-1,4-diol with styrene epoxide in the presence of base gives sulfide (33). The ring closure with an acid ion exchanger affords 2-phenyl-2,3-dihydrobenzo[1,4]oxathiin-6-ol (34).

The following Scheme 10 describes the synthesis of 6-phenyl-5,6,7,8-tetrahydro-naphthalen-2-ol (41) and 6-hydroxy-2-phenyl-3,4-dihydro-2H-naphthalen-1-one (40). Pd-catalyzed α-arylation of 6-methoxy-1-tetralone gives 6-methoxy-2-phenyl-3,4-dihydro-2H-naphthalen-1-one (39) which after demethylation leads to the phenolic compound (40).

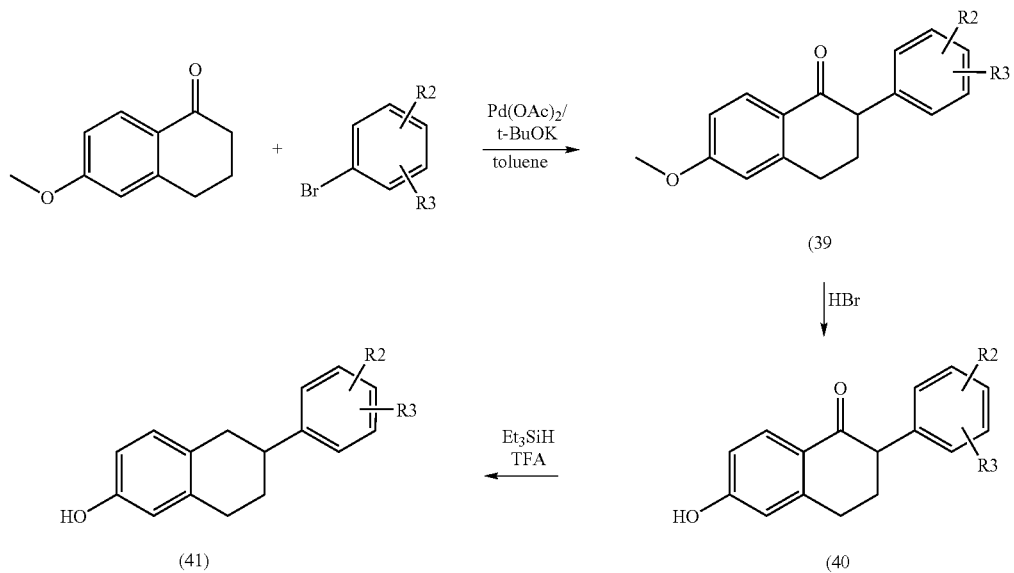

The following Scheme (11), wherein $R_2$ and $R_3$ are the same as defined above, describes the synthesis of 2,3-dihydro-2-phenyl-benzo[1,4]dioxin-6-ols (45). After protecting hydroxyl groups of 2,5-dihydroxyacetophenone this ketone rearranges with peracids and gives a phenol after hydrolysis. The phenol is condensed with a haloketone and after reduction and removal of protection groups the hydroxyphenol (44) is cyclised to a 2,3-dihydro-2-phenyl-benzo[1,4]-dioxin-6-ol (45).

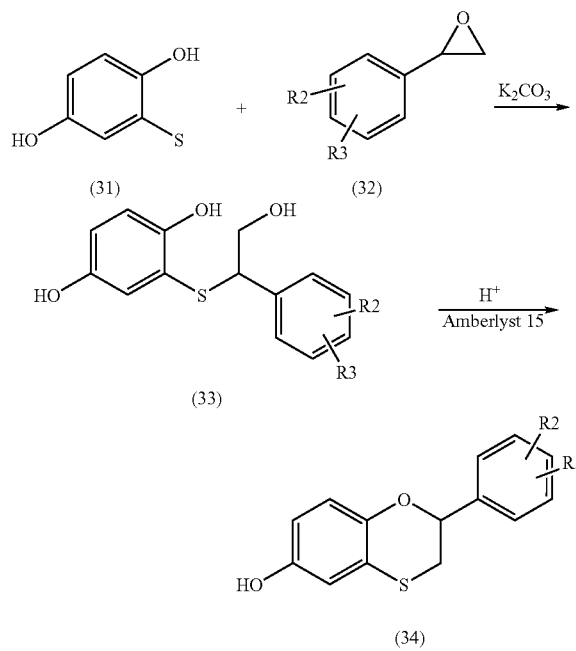

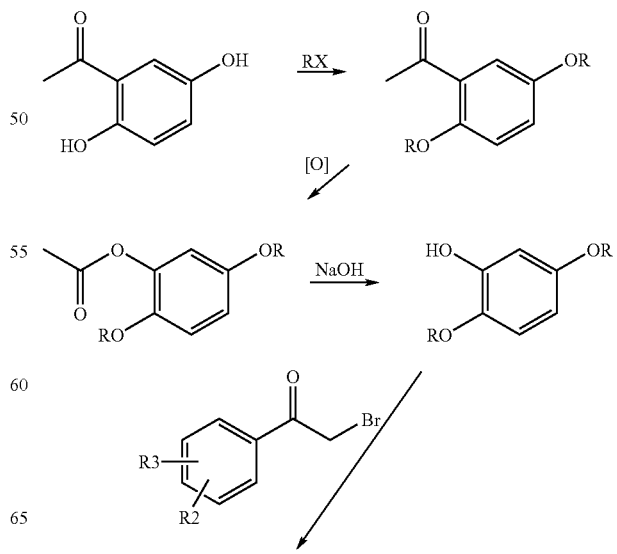

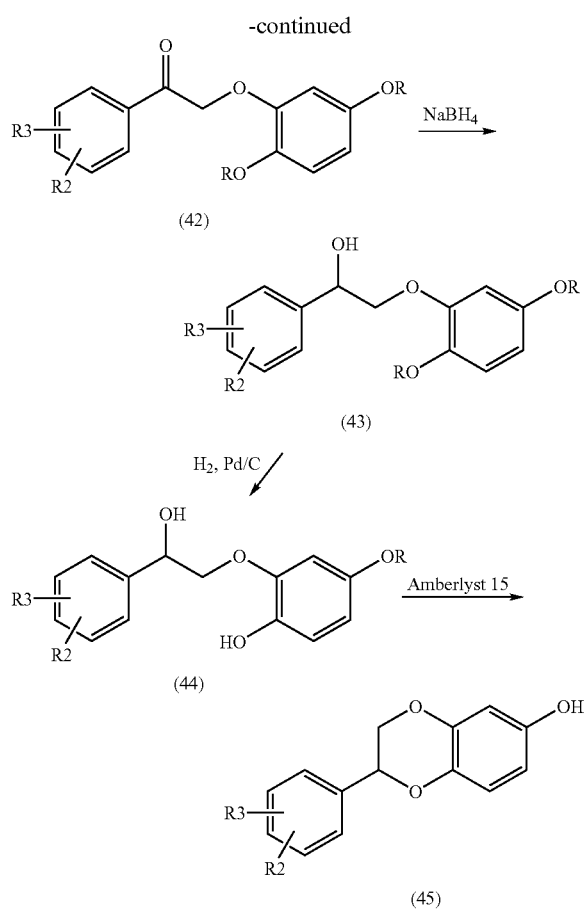

Salts and esters of the compounds, when applicable, may be prepared by known methods. Physiologically acceptable salts are useful as active medicaments. Examples are the salts with inorganic acids such as hydrochloric acid, hydrobromic acid or nitric acid, and salts with organic acids such as methanesulfonic acid, citric acid or tartaric acid. Physiologically acceptable esters are also useful as active medicaments. Examples are the esters with aliphatic or aromatic acids such as acetic acid or with aliphatic or aromatic alcohols.

The term "alkyl" as employed herein by itself or as part of another group includes both straight, branched and cyclized chain radicals of up to 18 carbon atoms, preferably 1 to 7 carbon atoms, most preferably 1 to 4 carbon atoms. The term "lower alkyl" as employed herein by itself or as part of another group includes straight, branched and cyclized chain radicals of 1 to 7, preferably 1 to 4, most preferably 1 or 2 carbon atoms. Specific examples for the alkyl and lower alkyl residues, respectively, are methyl, ethyl, propyl, isopropyl, butyl, tert. butyl, pentyl, cyclopentyl, hexyl, cyclohexyl, octyl, decyl and dodecyl including the various branched chain isomers thereof.

The term "alkoxy" as employed herein by itself or as part of another group includes an alkyl group as defined above linked to an oxygen atom.

The term "acyl" as employed herein by itself or as part of another group refers to an alkylcarbonyl or alkenylcarbonyl group, the alkyl and alkenyl groups being defined above.

Compounds of the invention may be administered to a patient in therapeutically effective amounts which range usually from about 0.05 to 200 mg, preferably 0.1 to 100 mg, more preferably 0.5 to 50, mg per day depending on the age, weight, condition of the patient, administration route and the $Na^+/Ca^{2+}$ exchange inhibitor used. The compounds of the invention can be formulated into dosage forms using the principles known in the art. It can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 0.5 to about 20%, per weight of the total composition.

Experiments

The effects of the compounds of the invention were tested on ouabain-induced arrhythmias in guinea-pig papillary muscles.

Methods

Guinea-pig papillary muscles were mounted into horizontal muscle cuvette. A hook connected to force transducer was attached to another end of the muscle. Muscle preparations were electrically paced at 1 Hz with field stimulation via platinum electrodes. Modified Tyrode solution was used for superfusion of muscle preparations. The composition of the Tyrode solution was the following (mM): NaCl 135, $MgCl_2 \times 6H_2O$ 1, KCl 5, $CaCl_2 \times 2H_2O$ 2, $NaHCO_3$ 15, $Na_2HPO_4 \times 2H_2O$ 1, and glucose 10. The Tyrode solution was gassed with carbogen (95% $O_2$, 5% $CO_2$) to set pH at 7.4. Experiments were carried out at 37° C. Acquisition and analysis of twitch tensions with Action Potential and Force Measurement System (ACFO v1.0, Fision Ltd, Finland).

Inhibition of Ouabain-Induced Arrhythmias

Ouabain by blocking of sodium-potassium ATPase increase intracellular sodium which is changed for calcium via NCX. Increased intracellular calcium is leading to overload of sarcoplasmic reticulum (SR) and spontaneous calcium release from SR inducing delayed afterpolarizations (DADs). Equivalence for DADs in force signal is aftercontractions (ACs) which are seen as spontaneous twitches after the pacing controlled twitch.

Figure 2:
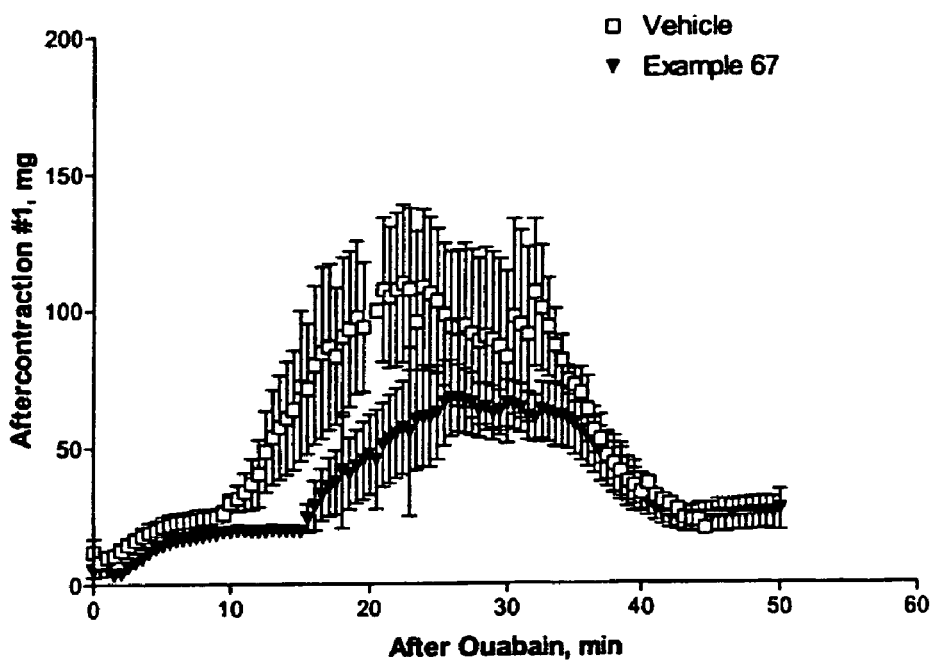
FIG. 2 shows the antiarrhythmic effects of the compound of Example 67 on ouabain-induced aftercontractions in guinea-pig isolated papillary muscles.

The compounds of the invention delayed appearance and decreased amplitude of aftercontractions. As shown in FIG. 1, the title compound of Example 27, at 30 μM concentration, delayed appearance [38±7.5 min vs vehicle: 25±8.9 min (mean±SD), p=0.013, n=5] and decreased maximum amplitude of aftercontractions #1 (74±16 mg vs vehicle: 143±54 mg, p=0.008, One-way ANOVA followed by LSD; n=5). As shown in FIG. 2, the title compound of Example 67, at 10 μM, decreased maximum amplitude of aftercontractions #1 (88±20 mg vs vehicle: 143±54 mg, p=0.027, n=5).

EXAMPLES

Example 1

5-Nitro-2-(2-phenylchroman-6-yloxy)pyridine a) 2-phenylchroman-6-ol

Zinc (5.4 g, 83.2 mmol), mercury (II) chloride (340 mg), concentrated hydrogen chloride (0.2 ml) and water were mixed at room temperature for 15 minutes and the mixture was decanted. 6-Hydroxyflavanone (1.0 g) was added as a suspension in a mixture of acetic acid (25 ml), concentrated hydrogen chloride (5.2 ml) and water (2 ml). The reaction mixture was refluxed for 1½ hours. After cooling into room temperature, the reaction mixture was filtered and the filtrate was extracted with ethyl acetate. The combined organic layers were washed with saturated $NaHCO_3$-solution, then with water and dried with $Na_2SO_4$. The 2-phenylchroman-6-ol was purified by column chromatography using heptane-ethyl acetate (2:1) as an eluant. $^1$H NMR (400 MHz, $d_6$-DMSO) δ: 8.78 (s, 1H), 7.43-7.31 (m, 5H), 6.63 (d, 1H, J 8.6 Hz), 6.51 (dd, 1H, J 8.6, 2.9 Hz), 6.48 (d, 1H, J 2.9 Hz), 4.98 (dd, 1H, J, 9.9, 2.2 Hz), 2.89 (ddd, 1H, J −16.7, 11.3, 6.1 Hz), 2.63 (ddd, 1H, J −16.7, 5.5, 3.3 Hz) 2.10 (m, 1H), 1.94 (m, 1H).

b) 5-Nitro-2-(2-phenylchroman-6-yloxy)pyridine

Potassium fluoride (225 mg) was added into a solution of 2-phenylchroman-6-ol (300 mg) in dry DMF (3 ml). After stirring the resulting mixture at 120° C. for 30 minutes 2-chloro-5-nitropyridine (195 mg) was added. The reaction mixture was stirred for a further 6½ hours at 120° C. After cooling into room temperature 1 M HCl-solution was added and the mixture was extracted with ethyl acetate. The combined organic layers were washed with water then with saturated NaCl-solution and dried with $Na_2SO_4$. 5-Nitro-2-(2-phenylchroman-6-yloxy)pyridine was recrystallised from acetone-2-propanol (1:5). $^1$H NMR (400 MHz, $d_6$-DMSO) δ: 9.00 (d, 1H, J 2.9 Hz), 8.60 (dd, 1H, J 9.2, 2.9 Hz), 7.47-7.32 (m, 5H), 7.20 (d, 1H, J 9.2 Hz), 7.00-6.89 (m, 3H), 5.15 (dd, 1H, J 10.1, 2.2 Hz), 2.99 (ddd, 1H, J −16.8, 11.3, 6.2 Hz), 2.75 (ddd, 1H, J −16.8, 5.4, 3.3 Hz), 2.18 (m, 1H), 2.02 (m, 1H).

Example 2

Dimethyl[2-(2-phenylchroman-6-yloxy)ethyl]amine

Cesium carbonate (230 mg) and an excess of 2-(dimethylamino)ethyl chloride in ethyl acetate were added into a solution of 2-phenylchroman-6-ol (150 mg) in acetonitrile (5 ml). The reaction mixture was refluxed for 30 minutes. After removing the solvents, the residue was taken up in water and extracted with ethyl acetate. The combined organic layers were washed with water and then with saturated NaCl-solution and dried with $Na_2SO_4$. The dimethyl[2-(2-phenylchroman-6-yloxy)-ethyl]amine was crystallised from heptane. $^1$H NMR (400 MHz, $d_6$-DMSO) δ: 7.43-7.30 (m, 5H), 6.75-6.67 (m, 3H), 5.03 (dd, 1H, J 10.0, 2.2 Hz), 3.95 (t, 2H, J 5.9 Hz), 2.94 (ddd, 1H, J −16.7, 10.9, 5.8 Hz), 2.69 (ddd, 1H, J −16.7, 5.2, 3.3 Hz), 2.58 (t, 2H, J 5.9 Hz), 2.13 (m, 1H), 1.96 (m, 1H).

Example 3

5-Methoxy-2-(2-phenylchroman-6-yloxy) phenylamine Hydrochloride a) 6-(4-Methoxy-2-nitrophenoxy)-2-phenylchroman The 2-phenylchroman-6-ol (500 mg) and 1-chloro-4-methoxy-2-nitrobenzene (390 mg) were dissolved in DMSO (10 ml). Potassium hydroxide (230 mg) and potassium iodide (520 mg) were added and the resulting mixture was stirred at 90° C. for 1 hour. After cooling it was poured in to 1 M HCl-solution (20 ml) and extracted with dichloromethane. The combined organic layers were washed with water until neutral and then with saturated NaCl-solution and dried with $Na_2SO_4$. After evaporating the solvents the 6-(4-Methoxy-2-nitrophenoxy)-2-phenylchroman was obtained by trituration with methanol. $^1$H NMR (400 MHz, $d_6$-DMSO) δ: 7.58 (d, 1H, J 3.1 Hz), 7.45-7.33 (m, 6H), 7.28 (dd, 1H, J 9.2 Hz, 3.1 Hz), 7.10 (d, 1H, J 9.2 Hz), 6.86-6.78 (m, 3H), 5.10 (dd, 1H, J 10.0, 1.9 Hz), 3.83 (s, 3H), 2.92 (ddd, 1H, J −16.9, 11.2, 5.9 Hz), 2.75 (ddd, 1H, J −16.9, 7.9, 4.2 Hz), 2.15 (m, 1H), 1.97 (m, 1H).

b)
5-Methoxy-2-(2-phenylchroman-6-yloxy)phenylamine Hydrochloride 6-(4-Methoxy-2-nitrophenoxy)-2-phenylchroman (360 mg) was dissolved ethyl acetate and 10% palladium on carbon (90 mg) was added. The reaction mixture was hydrogenated for 2 hours at normal pressure and room temperature. It was then filtered through Celite and washed with ethyl acetate. The 5-methoxy-2-(2-phenylchroman-6-yloxy)phenylamine was isolated as its hydrochloride salt. $^1$H NMR (400 MHz, $d_6$-DMSO) δ: 7.44-7.33 (m, 5H), 6.83-6.72 (m, 4H), 6.68 (d, 1H, J 2.9 Hz), 6.48 (dd, 1H, J 8.9, 2.8 Hz), 5.07 (dd, 1H, J 10.0, 2.2 Hz), 3.70 (s, 3H), 2.93 (ddd, 1H, J −17.0, 11.1, 6.1 Hz), 2.68 (ddd, 1H, J −17.0, 8.3, 4.5 Hz), 2.15 (m, 1H), 1.97 (m, 1H).

Example 4

2-(2-Phenylchroman-6-yloxy)ethylamine Methane Sulfonate a) 6-(2-azidoethoxy)-2-phenylchroman 2-Phenylchroman-6-ol (340 mg), 1-bromo-2-chloroethane (1.25 ml) and cesium carbonate (977 mg) were dissolved in acetonitrile (4 ml). The reaction mixture was refluxed for 4 hours. After cooling into room temperature it was poured in 1 M HCl-solution and extracted with dichloromethane. The combined dichloromethane extracts were washed with water and dried with $Na_2SO_4$. The mixture was passed through silica gel column using ethyl acetate-hexane (1:7) as an eluant resulting 190 mg of haloethane derivative. It was dissolved in DMF (5 ml) and sodium azide (214 mg) was added. The reaction mixture was refluxed for 2 hours. The mixture was filtered. Ethyl acetate was added to the filtrate and it was then washed once with 1 M HCl-solution and then several times with water and dried with $Na_2SO_4$. The solvents were evaporated under reduced pressure to give 6-(2-azidoethoxy)-2-phenylchroman. $^1$H NMR (400 MHz, $d_6$-DMSO) δ: 7.44-7.32 (m, 5H), 6.78-6.71 (m, 3H), 5.04 (dd, 1H, J 10.1, 2.3 Hz), 4.10 (t, 2H, J 4.8 Hz), 3.60 (t, 2H, J 4.8 Hz), 2.95 (ddd, 1H, J −16.8, 11.1, 6.0 Hz), 2.70 (ddd, 1H, J −16.8, 5.3, 3.3 Hz), 2.14 (m, 1H), 1.97 (m, 1H).

b) 2-(2-Phenylchroman-6-yloxy)ethylamine Methane Sulfonate

Triphenylphosphine (165 mg) and 40 µl of water were added into a solution of 6-(2-azidoethoxy)-2-phenylchroman (155 mg) in tetrahydrofuran. The resulting mixture was stirred for 2 hours at room temperature. 2-(2-Phenylchroman-6-yloxy)-ethylamine was isolated as its methane sulfonate salt. $^1$H NMR (400 MHz, $d_6$-DMSO) δ: 7.91 (bs, 3H), 7.44-7.32 (m, 5H), 6.81-6.75 (m, 3H), 5.05 (dd, 1H, J 9.9, 2.3 Hz), 4.08 (t, 2H, J 5.1 Hz), 3.19 (m, 2H), 2.95 (ddd, 1H, J −16.8, 11.0, 5.9. Hz), 2.71 (ddd, 1H, J −16.8, 5.2, 3.4 Hz), 2.30 (s, 3H), 2.15 (m, 1H), 1.97 (m, 1H).

Example 5

2-(2-Phenylchroman-6-yloxymethyl)-4,5-dihydro-1H-imidazole Hydrochloride a) (2-phenylchroman-6-yloxy)acetonitrile

Cesium carbonate (310 mg) and chloroacetonitrile (62 μl) were added into a solution of 2-phenylchroman-6-ol (200 mg) in acetonitrile (3 ml). The resulting mixture was refluxed for 6 hours. The reaction mixture was allowed to cool to room temperature and 1 M HCl-solution was added and it was extracted with ethyl acetate. The combined organic layers were washed with water and saturated NaCl-solution and dried with $Na_2SO_4$. The solvents were evaporated under reduced pressure to give (2-phenylchroman-6-yloxy)acetonitrile. $^1$H NMR (400 MHz, $d_6$-DMSO) δ: 7.44-7.30 (m, 5H), 6.86-6.81 (m, 3H), 5.08 (dd, 1H, J 9.8, 2.2 Hz), 5.07 (s, 2H), 2.97 (ddd, 1H, J −16.9, 10.9, 6.0. Hz), 2.71 (ddd, 1H, J −16.9, 5.0, 3.4 Hz), 2.15 (m, 1H), 1.97 (m, 1H).

b) 2-(2-Phenylchroman-6-yloxymethyl)4,5-dihydro 1H-imidazole Hydrochloride

Dry HCl was passed through a solution of (2-phenylchroman-6-yloxy)acetonitrile (270 mg) in diethyl ether and 90 μl of absolute ethanol while cooling with ice bath. Reaction mixture was evaporated to the dryness after formation of the intermediate imidate. Precipitate was dissolved in absolute ethanol and 252 μl ethylene diamine was added to the cooled solution. Reaction mixture was allowed to warm to room temperature, evaporated to dryness, dissolved in dichloromethane and washed with water. Combined organic layers were dried and treated with charcoal. The 2-(2-Phenylchroman-6-yloxymethyl)4,5-dihydro-1H-imidazole was isolated as its HCl-salt. $^1$H-NMR ($d_4$-MeOH): 7.5-7.2 (m, 5H), 6.85-6.75 (m, 3H), 5.01 (d, 1H, J 8.8 Hz), 4.97 (s, 2H), 4.00 (s, 4H), 3.02-2.90 (m, 1H), 2.80-2.70 (m, 1H), 2.21-2.12 m, 1H), 2.05-1.90 (m, 1H). (M)$^+$=308 (100%)

Example 6

6-(5-Nitropyridin-2-yloxy)-2-phenylchroman-4-one 6-(5-Nitropyridin-2-yloxy)-2-phenylchroman-4one was prepared as described for 5-Nitro-2-(2-phenylchroman-6-yloxy)pyridine in Example 1(b) using 200 mg of 6-hydroxyflavanone. $^1$H NMR (400 MHz, $d_6$-DMSO) δ: 9.03 (bs, 1H), 8.64 (d, 1H, J 9.0 Hz), 7.59-7.41 (m, 7H), 7.31 (d, 1H, J 9.0 Hz), 7.23 (d, 1H, 8.8 Hz), 5.75 (dd, 1H, J 12.3, 2.9 Hz), 3.30 (dd, 1H, −16.3, 12.3 Hz), 2.87 (dd, 1H, −16.3, 2.9 Hz).

Example 7

7-(5-Nitropyridin-2-yloxy)-2-phenylchroman-4-one 7-(5-Nitropyridin-2-yloxy)-2-phenylchroman-4-one was prepared as described for 5-Nitro-2-(2-phenylchroman-6-yloxy)pyridine in Example 1(b) using 150 mg of 7-hydroxyflavanone. $^1$H NMR (400 MHz, $d_6$-DMSO) δ: 9.07 (d, 1H, J 2.8 Hz), 8.67 (dd, 1H, J 9.0, 2.8 Hz), 7.89 (d, 1H, J 8.6 Hz), 7.60-7.35 (m, 6H), 7.04 (d, 1H, 2.1 Hz), 6.97 (dd, 1 H, 8.6, 2.1 HZ), 5.75 (dd, 1H, J 13.0, 2.7 Hz), 3.32 (dd, 1H, 16.9, 13.0 Hz), 2.85 (dd, 1H, −16.9, 2.7 Hz).

Example 8

6-(5-Nitropyridin-2-yloxy)-2-phenylchroman-4-ol a) 2-Phenylchroman-4,6-diol

Into a suspension of 6-hydroxyflavanone (1.0 g) in dry THF (11.5 ml) was added dropwise a solution of borane-THF complex (12.5 ml, 1.0 M in THF) under nitrogen. The reaction mixture was refluxed for 1 hour. After cooling to the room temperature it was poured into an ice-2 M HCl-solution. 2-Phenylchroman-4,6-diol was filtered. $^1$H NMR (400 MHz, $d_6$-DMSO) δ: 8.83 (s, 1H), 7.45-7.38 (m, 4H), 7.35 (m, 1H), 6.89 (d, 1H, J 2.8 Hz), 6.59 (d, 1H, J 8.7 Hz), 6.54 (dd, 1H, J 8.7, 2.8 Hz), 5.41 (d, 1H, J 7.0 Hz), 5.11 (dd, 1H, J 11.7, 1.2 Hz), 4.87 (m, 1H), 2.26 (m, 1H), 1.90 (m, 1H).

b) 6-(5-Nitropyridin-2-yloxy)-2-phenylchroman-4-ol 6-(5-Nitropyridin-2-yloxy)-2-phenylchroman-4-ol was prepared as described for 5-nitro-2-(2-phenylchroman-6-yloxy)pyridine in Example 1 (b) starting from 1.5 g of 2-phenylchroman-4,6-diol. The product was passed through a silica gel column using toluene-ethyl acetate (4:1) as an eluant and then crystallised from 2-propanol. $^1$H NMR (400 MHz, $d_6$-DMSO) δ: 9.04 (d, 1H, J 2.7 Hz), 8.61 (dd, 1H, J 9.1, 2.7 Hz), 7.50-7.36 (m, 5H), 7.25 (d, 1H, J 2.7 Hz), 7.22 (d, 1H, 9.1 Hz), 7.00 (dd, 1H, J 8.7, 2.7 Hz), 6.88 (d, 1H, J 8.7 Hz), 5.65 (d, 1H, J 6.3 Hz), 5.30 (dd, 1H, J 11.9, 1.3 Hz), 4.99 (m, 1H), 2.33 (m, 1H), 1.98 (m, 1H).

Example 9

2-[2-(3-Fluorophenyl)chroman-6-yloxy]-5-nitropyridine a) 2-(3-Fluorophenyl)-6-hydroxychroman-4-one

2',5'-Dihydroxyacetophenone (1.50 g) was dissolved in warm glacial acetic acid (26 ml). 3-Fluorobenzaldehyde (1.35 g) and ammonium acetate (0.98 g) were added. The reaction mixture was refluxed for 2 hours. It was allowed to cool to room temperature and poured in ice. The precipitate formed was filtered resulting in 2.2 g of a mixture of 2-(3-fluorophenyl)-6-hydroxychroman-4-one and 1-(2,5-dihydroxyphenyl)-3-(3-fluorophenyl)propenone. The obtained mixture was dissolved in ethanol (90 ml) and sodium acetate (1.75 g) was added. The reaction mixture was refluxed for 5 hours. It was then allowed to cool to room temperature and diluted with water and filtered. The 2-(3-fluorophenyl)-6-hydroxychroman-4-one was recrystallised from acetic acid. $^1$H NMR (400 MHz, $d_6$-DMSO) δ: 9.45 (s, 1H), 7.47 (m, 1H), 7.40-7.37 (m, 2H), 7.22 (m, 1H), 7.12 (d, 1H, J 3.0 Hz), 7.05 (dd, 1H, J 8.8, 3.0 Hz), 6.98 (d, 1H, J 8.8 Hz), 5.59 (dd, 1H, J 13.0, 2.9 Hz), 3.21 (dd, 1H, J −16.9, 13.0 Hz), 2.82 (dd, 1H, J −16.9, 2.9 Hz).

b) 2-(3-Fluorophenyl)chroman-4,6-diol 2-(3-Fluorophenyl)chroman-4,6-diol was prepared as described for 2-phenylchroman-4,6-diol in Example 8(a) starting from 220 mg of 2-(3-fluorophenyl)-6-hydroxychroman-4-one. $^1$H NMR (400 MHz, $d_6$-DMSO) δ: 8.85 (s, 1H), 7.45 (m, 1H), 7.30-7.25 (m, 2H), 7.15 (m, 1H), 6.88 (d, 1H, J 2.8 Hz), 6.62 (d, 1H, J 8.7 Hz), 6.55 (dd, 1H, J 8.7, 2.8 Hz), 5.44 (d, 1H, J 7.0 Hz), 5.15 (d, 1H, J 10.7 Hz), 4.86 (m, 1H), 2.29 (m, 1H), 1.86 (m, 1H).

c) 2-(3-Fluorophenyl)chroman-6-ol

Triethylsilane (960 μl) was added slowly into a solution of 2-(3-fluorophenyl)chroman-4,6-diol (195 mg) in dichloromethane (4 ml). Trifluoroacetic acid (1.9 ml) was then added dropwise into a reaction mixture and it was stirred at room temperature for 5 hours. The reaction mixture was poured on ice-water and extracted with dichloromethane. The residue was evaporated under reduced pressure with toluene to obtain 2-(3-fluorophenyl)chroman-6-ol. $^1$H NMR (400 MHz, d$_6$-DMSO) δ: 8.78 (s, 1H), 7.43 (m, 1H), 7.28-7.25 (m, 2H), 7.14 (m, 1H), 6.66 (d, 1H, J 8.5 Hz) 6.52 (dd, 1H, J 8.5, 2.7 Hz), 6.49 (d, 1H, J 2.7 Hz), 5.03 (dd, 1H, J 9.9, 2.1 Hz), 2.86 (m, 1H), 2.63 (m, 1H), 2.13 (m, 1H), 1.93 (m, 1H).

d) 2-[2-(3-Fluorophenyl)chroman-6-yloxy]-5-nitropyridine

2-[2-(3-Fluorophenyl)chroman-6-yloxy]-5-nitropyridine was prepared as described for 5-nitro-2-(2-phenylchroman-6-yloxy)pyridine in Example 1(b) starting from 210 mg of 2-(3-fluorophenyl)chroman-6-ol. The product was recrystallised from 2-propanol. $^1$H NMR (400 MHz, CDCl$_3$) δ: 9.07 (d, 1H, J 2.8 Hz), 8.46 (dd, 1H, J 9.0, 2.8 Hz), 7.36 (m, 1H), 7.21-7.15 (m, 2H), 7.03 (m, 1H), 7.01 (d, 1H, J 9.0 Hz), 6.98 (d, 1H, J 8.6 Hz), 6.92 (dd, 1H, J 8.6, 2.7 Hz), 6.90 (d, 1H, J 2.7 Hz), 5.09 (dd, 1H, J 10.3, 2.4 Hz), 3.01 (ddd, 1H, J −16.9, 11.4, 6.0 Hz), 2.82 (ddd, 1H, J −16.9, 5.1, 3.2 Hz), 2.24 (m, 1H), 2.09 (m, 1H).

Example 10

5-Nitro-2-(2-phenylchroman-7-yloxy)pyridine a) 2-Phenylchroman-7-ol

2-Phenyl-chroman-7-ol was prepared as described for 5-nitro-2-(2-phenylchroman-6-yloxy)pyridine in Example 1(a) starting from 1.0 g of 7-hydroxy-flavanone. The product was purified by column chromatography using heptane-ethyl acetate (2:1) as an eluant. $^1$H NMR (400 MHz, CD$_3$OD) δ: 7.41-7.28 (m, 5H), 6.86 (d, 1H, J 8.2 Hz), 6.32 (dd, 1H, J 8.2, 2.4 Hz), 6.29 (d, 1H, J 2.4 Hz), 5.00 (dd, 1H, J 9.9, 2.4 Hz), 2.84 (m, 1H), 2.64 (m, 1H), 2.15 (m, 1H), 1.99 (m, 1H).

b) 5-Nitro-2-(2-phenylchroman-7-yloxy)pyridine

5-Nitro-2-(2-phenylchroman-7-yloxy)pyridine was prepared as described for 5-nitro-2-(2-phenylchroman-6-yloxy)pyridine in Example 1(b) starting from 115 mg of 2-phenylchroman-7-ol. The product was purified on preparative TLC-plate covered with silica gel using toluene-ethyl acetate (15:1) as an eluant. $^1$H NMR (400 MHz, d$_6$-DMSO) δ: 9.04 (d, 1H, J 2.8 Hz), 8.60 (dd, 1H, J 9.1, 2.8 Hz), 7.46-7.32 (m, 5H), 7.22 (d, 1H, J 9.1 Hz), 7.20 (d, 1H, J 8.9 Hz), 6.72 (dd, 1H, J 8.9, 2.3 Hz), 6.72 (d, 1H, J 2.3 Hz), 5.16 (dd, 1H, J 10.1, 2.1 Hz), 2.97 (ddd, 1H, J −16.7, 11.3, 5.9 Hz), 2.77 (ddd, 1H, J −16.7, 8.1, 4.5 Hz), 2.20 (m, 1H), 2.02 (m, 1H).

Example 11

2-[2-(2,4-Dichlorophenyl)chroman-6-yloxy]-5-nitropyridine a) 2-(2,4-Dichlorophenyl)-6-hydroxychroman-4-one 2-(2,4-Dichlorophenyl)-6-hydroxychroman-4-one was prepared as described for 2-(3-fluorophenyl)-6-hydroxychroman-4-one in Example 9(a) starting from 1.0 g of 2',5'-dihydroxyacetophenone and 1.4 g of 2,4-dichlorobenzaldehyde. The product was recrystallised from acetic acid. $^1$H NMR (400 MHz, d$_6$-DMSO) δ: 9.49 (s, 1H), 7.78 (d, 1H, J 8.5 Hz), 7.71 (d, 1H, J 2.0 Hz), 7.57 (dd, 1H, J 8.5, 2.0 Hz), 7.14 (d, 1H, J 3.0 Hz), 7.06 (dd, 1H, J 8.8, 3.0 Hz), 6.97 (d, 1H, J 8.8 Hz), 5.77 (dd, 1H, J 13.5, 2.7 Hz), 3.18 (dd, 1H, J −16.9, 13.5 Hz), 2.78 (dd, 1H, J −16.9, 2.7 Hz).

b) 2-(2,4-Dichlorophenyl)chroman-4,6-diol 2-(2,4-Dichlorophenyl)chroman-4,6-diol was prepared as described for 2-phenylchroman-4,6-diol in Example 8(a) starting from 1.2 g of 2-(2,4-dichlorophenyl)-6-hydroxychroman-4-one. The product was purified by column chromatography using heptane-ethyl acetate (2:1) as an eluant. $^1$H NMR (400 MHz, d$_6$-DMSO) δ: 8.89 (s, 1H), 7.66 (d, 1H, J 2.1 Hz), 7.64 (d, 1H, J 8.5 Hz), 7.51 (dd, 1H, J 2.1, 8.5 Hz), 6.89 (d, 1H, J 2.7 Hz), 6.63 (d, 1H, J 8.7 Hz), 6.56 (dd, 1H, J 2.7, 8.7 Hz), 5.50 (d, 1H, J 6.8 Hz), 5.37 (d, 1H, J 10.4 Hz), 4.90 (m, 1H), 2.32 (m, 1H), 1.80 (m, 1H).

c) 2-(2,4-Dichlorophenyl)chroman-6-ol 2-(2,4-Dichlorophenyl)chroman-6-ol was prepared as described for 2-(3-fluorophenyl)chroman-6-ol in Example 9(c) starting from 625 mg of 2-(2,4-dichlorophenyl)chroman-4,6-diol. $^1$H NMR (400 MHz, d$_6$-DMSO) δ: 8.85 (s, 1H), 7.65 (d, 1H, J 2.2 Hz), 7.57 (d, 1H, J 8.4 Hz), 7.49 (dd, 1H, J 8.4, 2.2 Hz), 6.67-6.51 (m, 3H), 5.21 (dd, 1H, J 10.3, 2.1 Hz), 2.91 (m, 1H), 2.69 (m, 1H), 2.16 (m, 1H), 1.85 (m, 1H).

d) 2-[2-(2,4-Dichlorophenyl)chroman-6-yloxy]-5-nitropyridine

2-[2-(2,4-dichlorophenyl)chroman-6-yloxy]-5-nitropyridine was prepared as described for 5-nitro-2-(2-phenylchroman-6-yloxy)pyridine in Example 1(b) starting from 530 mg of 2-(2,4-dichlorophenyl)chroman-6-ol. The product was purified on preparative TLC-plate covered with silica gel using heptane-ethyl acetate (3:1) as an eluant. $^1$H NMR (400 MHz, CDCl$_3$) δ: 9.06 (d, 1H, J 2.7 Hz), 8.47 (dd, 1H, J 9.0, 2.7 Hz), 7.56 (d, 1H, J 8.4 Hz), 7.41 (d, 1H, J 2.0 Hz), 7.33 (dd, 1H, J 8.4, 2.0 Hz) 7.02 (d, 1H, J 9.0 Hz), 6.99-6.92 (m, 3H), 5.39 (dd, 1H, J 10.4, 2.2 Hz), 3.06 (ddd, 1H, J −16.9, 11.9, 6.0 Hz), 2.83 (ddd, 1H, J −16.9, 5.3, 2.7 Hz), 2.34 (m, 1H), 1.89 (m, 1H).

Example 12

2-[2-(3-Chlorophenyl)chroman-6-yloxy]-5-nitropyridine a) 2-(3-Chlorophenyl)-6-hydroxychroman-4-one 2-(3-Chlorophenyl)-6-hydroxychroman-4-one was prepared as described for 2-(3-fluorophenyl)-6-hydroxychroman-4-one in Example 9(a) starting from 2.0 g of 2',5'-dihydroxyacetophenone and 1.85 g of 3-chlorobenzaldehyde. The product was recrystallised from acetic acid. $^1$H NMR (400 MHz, d$_6$-DMSO) δ: 9.47 (s, 1H), 7.62 (s, 1H), 7.51-7.45 (m, 3H), 7.12 (d, 1H, J 3.0 Hz), 7.05 (dd, 1H, J 8.8, 3.0 Hz), 6.98 (d, 1H, J 8.8 Hz), 5.58 (dd, 1H, J 13.1, 2.9 Hz), 3.18 (dd, 1H, J −16.9, 13.1 Hz), 2.81 (dd, 1H, J −16.9, 2.9 Hz).

b) 2-(3-Chlorophenyl)chroman-4,6-diol 2-(3-Chlorophenyl)chroman-4,6-diol was prepared as described for 2-phenylchroman-4,6-diol in Example 8(a) starting from 730 mg of 2-(3-chloro-phenyl)-6-hydroxychroman-4-one. $^1$H NMR (400 MHz, d$_6$-DMSO) δ: 8.85 (s, 1H), 7.50 (d, 1H, J 1.7 Hz), 7.46-7.38 (m, 3H), 6.88 (d, 1H, J 2.5 Hz), 6.62 (d, 1H, J 8.6 Hz), 6.55 (dd, 1H, J 8.6, 2.5 Hz), 5.44 (d, 1H, J 6.6 Hz), 5.15 (dd, 1H, J 11.8, 1.4 Hz), 4.87 (m, 1H), 2.29 (m, 1H), 1.85 (m, 1H).

c) 2-(3-Chlorophenyl)chroman-6-ol 2-(3-Chlorophenyl)chroman-6-ol was prepared as described for 2-(3-fluorophenyl)chroman-6-ol in Example 9(c) starting from 635 mg of 2-(3-chloro-phenyl)chroman-4,6-diol. $^1$H NMR (300 MHz, d$_6$-DMSO) δ: 8.79 (s, 1H), 7.48 (d, 1H, J 0.7 Hz), 7.42-7.37 (m, 3H), 6.71-6.49 (m, 3H), 5.04 (m, 1H), 2.91 (m, 1H), 2.65 (m, 1H), 2.12 (m, 1H), 1.93 (m, 1H).

d) 2-[2-(3-Chlorophenyl)chroman-6-yloxy]-5-nitropyridine

2-[2-(3-Chlorophenyl)chroman-6-yloxy]-5-nitropyridine was prepared as described for 5-nitro-2-(2-phenylchroman-6-yloxy)pyridine in Example 1(b) starting from 590 mg of 2-(3-chlorophenyl)chroman-6-ol. The product was recrystallised from a 3:1 mixture of 2-propanol and ethyl acetate. $^1$H NMR (400 MHz, CDCl$_3$) δ: 9.04 (d, 1H, J 2.9 Hz), 8.60 (dd, 1H, J 9.0, 2.9 Hz), 7.53 (s, 1H), 7.467-7.42 (m, 3H), 7.20 (d, 1H, J 9.0 Hz), 7.00 (dd, 1H, J 8.7, 2.7 Hz), 6.97 (d, 1H, J 2.7 Hz), 6.94 (d, 1H, J 8.7 Hz), 5.18 (dd, 1H, J 10.2, 2.2 Hz), 2.97 (ddd, 1H, J −17.0, 11.5, 5.9 Hz), 2.83 (ddd, 1H, J −17.0, 8.1, 4.5 Hz), 2.21 (m, 1H), 2.00 (m, 1H).

Example 13

2-[2-(3,5-Difluorophenyl)chroman-6-yloxy]-5-nitropyridine a) 2-(3,5-Difluorophenyl)-6hydroxychroman-4-one 2-(3,5-Difluorophenyl)-6-hydroxychroman-4-one was prepared as described for 2-(3-fluorophenyl)-6-hydroxychroman-4-one in Example 9(a) starting from 1.0 g of 2',5'-dihydroxyacetophenone and 1.12 g of 3,5-difluorobenzaldehyde. The product was recrystallised from acetic acid. $^1$H NMR (400 MHz, d$_6$-DMSO) δ: 9.47 (s, 1H), 7.30-7.23 (m, 3H), 7.12 (d, 1H, J 2.9 Hz), 7.06 (dd, 1H, J 8.8, 2.9 Hz), 7.00 (d, 1H, J 8.8 Hz), 5.60 (dd, 1H, J 13.1, 2.8 Hz), 3.15 (dd, 1H, J −16.8, 13.1 Hz), 2.85 (dd, 1H, J −16.8, 2.8 Hz).

b) 2-(3,5-Difluorophenyl)chroman-4,6-diol 2-(3,5-Difluorophenyl)chroman-4,6-diol was prepared as described for 2-phenylchroman-4,6-diol in Example 8(a) starting from 800 mg of 2-(3,5-difluorophenyl)-6-hydroxychroman-4-one. $^1$H NMR (400 MHz, d$_6$-DMSO) δ: 8.87 (s, 1H), 7.21-7.17 (m, 3H), 6.88 (d, 1H, J 2.4 Hz), 6.64 (d, 1H, J 8.7 Hz), 6.55 (dd, 1H, J 2.4, 8.7 Hz), 5.47 (d, 1H, J 7.0 Hz), 5.17 (d, 1H, J 10.5 Hz), 4.86 (m, 1H), 2.32 (m, 1H), 1.85 (m, 1H).

c) 2-(3,5-Difluorophenyl)chroman-6-ol 2-(3,5-Difluorophenyl)chroman-6-ol was prepared as described for 2-(3-fluorophenyl)chroman-6-ol in Example 9(c) starting from 500 mg of 2-(3,5-difluorophenyl)chroman-4,6-diol. $^1$H NMR (300 MHz, d$_6$-DMSO) δ: 8.82 (s, 1H), 7.20-7.14 (m, 3H), 6.68 (d, 1H, J 8.6 Hz), 6.53 (d, 1H, J 2.9 Hz), 6.50 (dd, 1H, J 8.6, 2.9 Hz), 5.05 (dd, 1H, J 9.8, 2.2 Hz), 2.88 (ddd, 1H, J −16.7, 10.8, 5.9 Hz), 2.62 (ddd, 1H, J −16.7, 8.9, 5.0 Hz), 2.15 (m, 1H), 1.93 (m, 1H).

d) 2-[2-(3,5-Difluorophenyl)chroman-6-yloxy]-5-nitropyridine

2-[2-(3,5-Difluorophenyl)chroman-6-yloxy]-5-nitropyridine was prepared as described for 5-nitro-2-(2-phenylchroman-6-yloxy)pyridine in Example 1(b) starting from 340 mg of 2-(3,5-difluorophenyl)chroman-6-ol. The product was purified on preparative TLC-plate covered with silica gel using toluene-ethyl acetate as an eluant and then crystallised from 2-propanol. $^1$H NMR (400 MHz, d$_6$-DMSO) δ:9.04 (d, 1H, J 2.9 Hz), 8.60 (dd, 1H, J 9.1, 2.9 Hz), 7.23-7.19 (m, 4H), 7.01-6.95 (m, 3H), 5.18 (dd, 1H, J 10.0, 2.1 Hz), 2.97 (ddd, 1H, J −16.9, 10.9, 5.7 Hz), 2.76 (ddd, 1H, J −16.9, 8.4, 4.7 Hz), 2.22 (m, 1H), 1.99 (m, 1H).

Example 14

2-[2-(2.5-Difluorophenyl)chroman-6-yloxy]-5-nitropyridine a) 2-(2,5-Difluorophenyl)-6-hydroxychroman-4-one 2-(2,5-Difluorophenyl)-6-hydroxychroman-4-one was prepared as described for 2-(3-fluorophenyl)-6-hydroxychroman-4-one in Example 9(a) starting from 3.0 g of 2',5'-dihydroxyacetophenone and 2.57 ml of 2,5-difluorobenzaldehyde. The product was recrystallised from acetic acid. $^1$H NMR (300 MHz, d$_6$-DMSO) δ: 9.46 (s, 1H), 7.53 (m, 1H), 7.36-7.30 (m, 2H), 7.14 (d, 1H, J 3.0 Hz), 7.05 (dd, 1H, J 8.8, 3.0 Hz), 6.97 (d, 1H, J 8.8 Hz), 5.76 (dd, 1H, J 13.6, 2.7 Hz), 3.26 (dd, 1H, J −16.8, 13.6 Hz), 2.76 (dd, 1H, J −16.8, 2.7 Hz).

b) 2-(2,5-Difluorophenyl)chroman-4,6-diol 2-(2,5-Difluorophenyl)chroman-4,6-diol was prepared as described for 2-phenylchroman-4,6-diol in Example 8(a) starting from 1.0 g of 2-(2,5-difluorophenyl)-6-hydroxychroman-4-one. $^1$H NMR (400 MHz, d$_6$-DMSO) δ: 8.87 (s, 1H), 7.39-7.22 (m, 3H), 6.89 (d, 1H, J 2.8 Hz), 6.63 (d, 1H, J 8.7 Hz), 6.56 (dd, 1H, J 8.7, 2.8 Hz), 5.50 (d, 1H, J 6.8 Hz), 5.35 (d, 1H, J 11.2 Hz), 4.89 (m, 1H), 2.28 (m, 1H), 1.95 (m, 1H).

c) 2-(2,5-Difluorophenyl)chroman-6-ol 2-(2,5-Difluorophenyl)chroman-6-ol was prepared as described for 2-(3-fluorophenyl)chroman-6-ol in Example 9(c) starting from 420 mg of 2-(2,5-difluorophenyl)chroman-4,6-diol. $^1$H NMR (300 MHz, d$_6$-DMSO) δ: 8.82 (s, 1H), 7.34-7.22 (m, 3H), 6.71-6.51 (m, 3H), 5.20 (m, 1H), 2.93 (m, 1H), 2.68 (m, 1H), 2.11 (m, 1H), 1.98 (m, 1H).

d) 2-[2-(2,5-Difluorophenyl)chroman-6-yloxy]-5-nitropyridine

2-[2-(2,5-Difluorophenyl)chroman-6-yloxy]-5-nitropyridine was prepared as described for 5-nitro-2-(2-phenylchroman-6-yloxy)pyridine in Example 1(b) starting from 100 mg of 2-(2,5-difluorophenyl)chroman-6-ol. The product was recrystallised from 2-propanol. $^1$H NMR (400 MHz, CDCl$_3$) δ: 9.07 (dd, 1H, J 2.8, 0.4 Hz), 8.47 (dd, 1H, J 9.1, 2.8 Hz), 7.26 (m, 1H), 7.05-6.91 (m, 6H), 5.35 (dd, 1H, J 10.3, 1.5 Hz), 3.04 (ddd, 1H, J −16.9, 11.7, 6.0 Hz), 2.82 (ddd, 1H, J −16.9, 5.2, 3.0 Hz), 2.29 (m, 1H), 2.01 (m, 1H).

Example 15

2-[2-(3-Bromophenyl)chroman-6-yloxy]-5-nitropyridine a) 2-(3-Bromophenyl)-6-hydroxychroman-4-one 2-(3-Bromophenyl)-6-hydroxychroman-4-one was prepared as described for 2-(3-fluorophenyl)-6-hydroxychroman-4one in Example 9(a) starting from 3.0 g of 2',5'-dihydroxyacetophenone and 2.3 ml of 3-bromobenzaldehyde. The product was recrystallised from acetic acid. $^1$H NMR (300 MHz, $d_6$-DMSO) δ: 9.41 (s, 1H), 7.50 (m, 1H), 7.59-7.53 (m, 2H), 7.39 (m, 1H), 7.12 (d, 1H, J 2.9 Hz), 7.05 (dd, 1H, J 8.8, 2.9 Hz), 6.98 (d, 1H, J 8.8 Hz), 5.57 (dd, 1H, J 13.0, 2.9 Hz), 3.12 (dd, 1H, J −16.9, 13.0 Hz), 2.81 (dd, 1H, J −16.9, 2.9 Hz).

b) 2-(3-Bromo-phenyl)-chroman-4,6-diol 2-(3-Bromophenyl)-chroman-4,6-diol was prepared as described for 2-phenylchroman-4,6-diol in Example 8(a) starting from 1.0 g of 2-(3-bromophenyl)-6-hydroxychroman-4-one. $^1$H NMR (300 MHz, $d_6$-DMSO) δ: 8.83 (s, 1H), 7.63 (m, 1H), 7.53 (m, 1H), 7.46 (m, 1H), 7.37 (m, 1H), 6.88 (d, 1H, J 2.9 Hz), 6.62 (d, 1H, J 8.7 Hz), 6.55 (dd, 1H, J 8.7, 2.9 Hz), 5.42 (d, 1H, J 7.0 Hz), 5.14 (d, 1H, J 10.5 Hz), 4.86 (m, 1H), 2.29 (m, 1H), 1.84 (m, 1H).

c) 2-(3-Bromophenyl)chroman-6-ol 2-(3-Bromophenyl)chroman-6-ol was prepared as described for 2-(3-fluorophenyl)chroman-6-ol in Example 9(c) starting from 700 mg of 2-(3-bromophenyl)chroman-4,6-diol. $^1$H NMR (400 MHz, $d_6$-DMSO) δ: 8.81 (s, 1H), 7.61 (m, 1H), 7.51 (m, 1H), 7.43 (m, 1H), 7.35 (m, 1H), 6.67-6.48 (m, 3H), 5.01 (m, 1H), 2.87 (m, 1H), 2.63 (m, 1H), 2.12 (m, 1H), 1.92 (m, 1H).

d) 2-[2-(3-Bromophenyl)chroman-6-yloxy]-5-nitropyridine

2-[2-(3-Bromophenyl)chroman-6-yloxy]-5-nitropyridine was prepared as described for 5-nitro-2-(2-phenylchroman-6-yloxy)pyridine in Example 1(b) starting from 339 mg of 2-(3-bromophenyl)chroman-6-ol. The product was filtered through silica gel using toluene-ethyl acetate as an eluant and then crystallised from 2-propanol. $^1$H NMR (400 MHz, CDCl$_3$) δ: 9.04 (d, 1H, J 2.9 Hz), 8.60 (dd, 1H, J 9.2, 2.9 Hz), 7.66 (bs, 1H), 7.55 (m, 1H), 7.48 (m, 1H), 7.39 (m, 1H), 7.20 (d, 1H, J 9.2 Hz), 7.01-6.93 (m, 3H), 5.17 (dd, 1H, J 10.1, 2.2 Hz), 2.97 (m, 1H), 2.72 (m, 1H), 2.20 (m, 1H), 2.00 (m, 1H).

Example 16

2-[2-(4-Ethylphenyl)chroman-6-yloxy]-5-nitropyridine a) 2-(4-Ethylphenyl)-6-hydroxychroman-4-one 2-(4-Ethylphenyl)-6-hydroxychroman-4-one was prepared as described for 2-(3-fluorophenyl)-6-hydroxychroman-4-one in Example 9(a) starting from 1.0 g of 2',5'-dihydroxyacetophenone and 0.8 ml of 4-ethylbenzaldehyde. The product was recrystallised from acetic acid. $^1$H NMR (400 MHz, $d_6$-DMSO) δ: 7.43 (d, 2H, J 8.1 Hz), 7.25 (d, 2H, J 8.1 Hz), 7.11 (d, 1H, J 3.1 Hz), 7.03 (dd, 1H, J 8.9, 3.1 Hz), 6.93 (d, 1H, J 8.9 Hz), 5.51 (dd, 1H, J 13.0, 2.9 Hz), 3.15 (dd, 1H, J −16.9, 13.0 Hz), 2.75 (dd, 1H, J −16.9, 2.9 Hz), 2.62 (q, 2H, J 7.5 Hz), 1.18 (t, 3H, J 7.5 Hz).

b) 2-(4-Ethylphenyl)chroman-4,6-diol 2-(4Ethylphenyl)chroman-4,6-diol was prepared as described for 2-phenylchroman-4,6-diol in Example 8(a) starting from 474 mg of 2-(4-ethylphenyl)-6-hydroxychroman-4one. $^1$H NMR (400 MHz, $d_6$-DMSO) δ: 8.81 (s, 1H), 7.34 (d, 2H, J 8.0 Hz), 7.22 (d, 2H, J 8.0 Hz), 6.88 (d, 1H, J 2.8 Hz), 6.57 (d, 1H, J 8.6 Hz), 6.53 (dd, 1H, J 8.6, 2.8 Hz), 5.39 (d, 1H, J 7.1 Hz), 5.06 (d, 1H, J 10.7 Hz), 4.86 (m, 1H), 2.61 (q, 2H, J 7.6 Hz), 2.29 (m, 1H), 1.84 (m, 1H), 1.19 (t, 3H, J 7.6 Hz).

c) 2-(4-Ethylphenyl)chroman-6-ol 2-(4-Ethylphenyl)chroman-6-ol was prepared as described for 2-(3-fluorophenyl)chroman-6-ol in Example 9(c) starting from 425 mg of 2-(4-ethyl-phenyl)chroman-4,6-diol. The product was purified using heptane-ethyl acetate (3:1) as an eluant. $^1$H NMR (400 MHz, CD$_3$OD) δ: 7.26 (d, 2H, J 8.2 Hz), 7.13 (d, 2H, J 8.2 Hz), 6.65 (d, 1H, J 8.6 Hz), 6.55 (dd, 1H, J 8.6, 2.8 Hz), 6.51 (d, 1H, J 2.8 Hz), 4.83 (dd, 1H, J 10.1, 2.3 Hz), 2.84 (m, 1H), 2.62 (m, 1H), 2.59 (q, 2H, J 7.6 Hz), 2.03 (m, 1H), 1.93 (m, 1H), 1.19 (t, 3H, J 7.6 Hz).

d) 2-[2-(4-Ethylphenyl)chroman-6-yloxy]-5-nitropyridine

2-[2-(4-Ethylphenyl)chroman-6-yloxy]-5-nitropyridine was prepared as described for 5-nitro-2-(2-phenylchroman-6-yloxy)pyridine in Example 1(b) starting from 205 mg of 2-(4-ethylphenyl)chroman-6-ol. The product was recrystallised from a mixture of 2-propanol and acetone. $^1$H NMR (400 MHz, CDCl$_3$) δ: 9.04 (d, 1H, J 2.8 Hz), 8.60 (dd, 1H, J 9.1, 2.8 Hz), 7.36 (d, 2H, J 8.1 Hz), 7.24 (d, 2H, J 8.1 Hz), 7.20 (d, 1H, J 9.1 Hz), 7.00 (d, 1H, J 2.7 Hz), 6.96 (dd, 1H, J 8.8, 2.7 Hz), 6.89 (d, 1H, J 2.7 Hz), 5.11 (dd, 1H, J 10.1, 2.2 Hz), 2.98 (m, 1H), 2.75 (m, 1H), 2.62 (q, 2H, J 7.5 Hz), 2.16 (m, 1H), 2.01 (m, 1H), 1.19 (t, 3H, J 7.5 Hz).

Example 17

2-(3-Methyl-2-phenylchroman-6-yloxy)-5-nitropyridine a) 6-Hydroxy-3-methyl-2-phenylchroman-4-one

6-Hydroxy-3-methyl-2-phenylchroman-4-one was prepared as described for 2-(3-fluorophenyl)-6-hydroxychroman-4-one in Example 9(a) starting from 2.0 g of 2,5-dihydroxypropiophenone and 1.63 ml of benzaldehyde. The product was purified by column chromatography using heptane-ethyl acetate (3:1) as an eluant. $^1$H NMR (300 MHz, $d_6$-DMSO) δ: 9.37 (s, 1H), 7.53 (m, 2H), 7.47-7.39 (m, 3H), 7.13 (d, 1H, J 3.1 Hz), 7.02 (dd, 1H, J 8.9, 3.1 Hz), 6.89 (d, 1H, J 8.9 Hz), 5.17 (d, 1H, J 12.3), 3.18 (dq, 1H, J 12.3, 6.9 Hz), 0.84 (d, 3H, J 6.9 Hz).

b) 3-Methyl-2-phenylchroman-4,6diol

3-Methyl-2-phenylchroman-4,6-diol was prepared as described for 2-phenylchroman-4,6-diol in Example 8(a) starting from 474 mg of 6-hydroxy-3-methyl-2-phenylchroman-4-one. $^1$H NMR (300 MHz, $d_6$-DMSO) δ: 8.79 (s, 1H), 7.42-7.33 (m, 5H), 6.88 (bs, 1H), 6.53 (m, 2H), 5.37 (d, 1H, J 8.0 Hz), 4.70 (d, 1H, J 10.6 Hz), 1.94 (m, 1H), 0.73 (d, 3H, J 6.7 Hz).

c) 3-Methyl-2-phenylchroman-6-ol

3-Methyl-2-phenylchroman-6-ol was prepared as described for 2-(3-fluorophenyl)chroman-6-ol in Example 9(c) starting from 605 mg of 3-methyl-2-phenylchroman-4,6-diol. 1H NMR (400 MHz, $CD_3OD$) δ: 8.77 (s, 1H), 7.41-7.33 (m, 5H), 6.59-6.48 (m, 3H), 4.56 (d, 1H, J 9.2 Hz), 2.73 (dd, 1H, J −16.5, 5.0 Hz), 2.54 (dd, 1H, J −116.5, 5.8 Hz), 2.11 (m, 1H), 0.72 (d, 3H, J 6.6 Hz).

d) 2-(3-Methyl-2-phenylchroman-6-yloxy)-5-nitro-pyridine 2-(3-Methyl-2-phenylchroman-6-yloxy)-5nitropyridine was prepared as described for 5-nitro-2-(2-phenylchroman-6-yloxy)pyridine in Example 1(b) starting from 600 mg of 3-methyl-2-phenylchroman-6-ol. The product was purified by column chromatography using heptane-2-propanol (20:1) as an eluant. $^1$H NMR (400 MHz, $d_6$-DMSO) δ: 9.04 (d, 1H, J 2.8 Hz), 8.59 (dd, 1H, J 9.1, 2.8 Hz), 7.43-7.36 (m, 5H), 7.19 (d, 1H, J 9.1 Hz), 7.00 (d, 1H, J 2.6 Hz), 6.95 (dd, 1H, J 8.7, 2.6 Hz), 6.86 (d, 1H, J 8.7 Hz), 4.73 (d, 1H, J 9.3 Hz), 2.85 (dd, 1H, J −16.7, 5.0 Hz), 2.64 (dd, 1H, J −16.5, 10.9 Hz), 2.18 (m, 1H), 0.77 (d, 3H, J 6.7 Hz).

Example 18

3-Methyl-6-(5-nitropyridin-2-yloxy)-2-phenylchroman-4-one

Methyl-6-(5-nitropyridin-2-yloxy)-2-phenylchroman-4-one was prepared as described for 5-nitro-2-(2-phenylchroman-6-yloxy)pyridine in Example 1(b) starting from 200 mg of 6-hydroxy-3-methyl-2-phenylchroman-4-one. The product was purified by column chromatography using heptane-ethyl acetate (2:1) as an eluant and then crystallised from a mixture of 2-propanol and acetone. $^1$H NMR (400 MHz, $d_6$-DMSO) δ: 9.03 (d, 1H, J 2.9 Hz), 8.64 (dd, 1H, J 9.1, 2.9 Hz), 7.59-7.56 (m, 3H), 7.50-7.32 (m, 4H), 7.30 (d, 1H, J 9.1 Hz), 7.18 (d, 1H, J 8.9 Hz), 5.38 (d, 1H, J 12.5 Hz), 3.36 (dd, 1H, J 12.5, 6.9 Hz), 0.86 (d, 3H, J 6.9 Hz).

Example 19

2-[2-(2-Fluorophenyl)chroman-6-yloxy]-5-nitropyridine a) 2-(2-Fluorophenyl)-6-hydroxychroman-4-one 2-(2-Fluorophenyl)-6-hydroxychroman-4-one was prepared as described for 2-(3-fluorophenyl)-6-hydroxychroman-4-one in Example 9(a) starting from 2.0 g of 2',5'-dihydroxyacetophenone and 1.4 ml of 2-fluorobenzaldehyde. The product was recrystallised from acetic acid. $^1$H NMR (400 MHz, $d_6$-DMSO) δ: 9.45 (s, 1H), 7.67 (m, 1H), 7.47 (m, 1H), 7.32-7.25 (m, 2H), 7.14 (d, 1H, J 3.0 Hz), 7.04 (dd, 1H, J 8.9, 3.0 Hz), 6.95 (d, 1H, J 8.9 Hz), 5.77 (dd, 1H, J 13.5, 2.8 Hz), 3.26 (dd, 1H, J −16.9, 13.5 Hz), 2.76 (dd, 1H, J −16.9, 2.8 Hz).

b) 2-(2-Fluorophenyl)chroman-4,6-diol 2-(2-Fluorophenyl)chroman-4,6-diol was prepared as described for 2-phenylchroman-4,6-diol in Example 8(a) starting from 1.19 g of 2-(2-fluorophenyl)-6-hydroxychroman-4-one. $^1$H NMR (400 MHz, $d_6$-DMSO) δ: 8.85 (s, 1H), 7.56 (m, 1H), 7.40 (m, 1H), 7.28-7.21 (m, 2H), 6.89 (d, 1H, J 2.9 Hz), 6.60 (d, 1H, J 8.7 Hz), 6.54 (dd, 1H, J 8.7, 2.8 Hz), 5.46 (d, 1H, J 6.9 Hz), 5.35 (d, 1H, J 10.6 Hz), 4.89 (m, 1H), 2.26 (m, 1H), 1.98 (m, 1H).

c) 2-(2-Fluorophenyl)chroman-6-ol 2-(2-Fluorophenyl)chroman-6-ol was prepared as described for 2-(3-fluorophenyl)chroman-6-ol in Example 9(c) starting from 800 mg of 2-(2-fluorophenyl)chroman-4,6diol. $^1$H NMR (300 MHz, $d_6$-DMSO) δ: 7.50 (m, 1H), 7.39 (m, 1H), 7.26-7.19 (m, 2H), 6.63 (m, 1H), 6.53-6.50 (m, 2H), 5.21 (dd, 1H, J, 10.2, 2.3 Hz), 2.98 (ddd, 1H, J −16.9, 11.2, 6.0 Hz), 2.66 (ddd, 1H, J −16.9, 5.0, 2.9 Hz), 2.11 (m, 1H), 1.99 (m, 1H).

d) 2-[2-(2-Fluorophenyl)chroman-6-yloxy]-5-nitro-pyridine

2-[2-(2-Fluorophenyl)chroman-6-yloxy]-5-nitropyridine was prepared as described for 5-nitro-2-(2-phenylchroman-6-yloxy)pyridine in Example 1(b) starting from 390 mg of 2-(2-fluorophenyl)chroman-6-ol. The product was purified by column chromatography using heptane-ethyl acetate (4:1) as an eluant. $^1$H NMR (400 MHz, $CDCl_3$) δ: 9.04 (d, 1H, J 2.8 Hz), 8.60 (dd, 1H, J 9.1, 2.8 Hz), 7.56 (m, 1H), 7.43 (m, 1H), 7.30-7.22 (m, 2H), 7.20 (d, 1H, J 9.1 Hz), 7.02 (d, 1H, J 2.8 Hz), 6.98 (dd, 1H, J 8.7, 2.8 Hz), 6.91 (d, 1H, J 8.7 Hz), 5.37 (dd, 1H, J 10.4, 2.3 Hz), 3.04 (ddd, 1H, J −17.0, 11.5, 6.0 Hz), 2.82 (ddd, 1H, J −17.0, 5.1, 2.8 Hz), 2.18 (m, 1H), 2.08 (m, 1H).

Example 20

2-(2,3-Dihydro-2-phenyl-benzo[1,4]dioxin-6-yloxy)-5-nitropyridine a) 1-[2,5-Bis(benzyloxy)phenyl]ethanone

A mixture of 1-(2,5-dihydroxyphenyl)ethanone (3.16 g), benzyl chloride (7.04 g), potassium carbonate (12.4 g) and 18-Crown-6 (30 mg) in 2-butanone (50 ml) was heated under reflux for 5 hrs. After cooling the precipitate was filtered off. The filtrate was evaporated to dryness under reduced pressure and ether (50 ml) was added to it. The solution was washed twice with dilute sodium hydroxide solution, twice with dilute hydrochloric acid, dried over sodium sulphate and substantially evaporated to dryness under reduced pressure. The residue was triturated with cold n-heptane (30 ml), and the precipitate was filtered off with suction filtration giving after drying 2.85 g of 1-[2,5-Bis(benzyloxy)phenyl]ethanone. $^1$H NMR (400 MHz, DMSO-$d_6$) δ=2.50 (s, 3H), 5.08 (s, 2H), 5.18 (s, 2H), 7.20-7.50 (m, 13H).

b) Acetic Acid 2,5-bis(benzyloxy)phenyl Ester

A solution of 1-[2,5-bis(benzyloxy)phenyl]ethanone (2.25 g) and peracetic acid 40% (1.63 ml) in acetic acid (5.4 ml) was stirred at 60° C. for 1 h. After cooling to room temperature the precipitated product was collected by filtration, washed with cold ether and dried under reduced pressure. Acetic acid 2,5-bis(benzyloxy)phenyl ester was recrystallized from 2-propanol. Yield is 1.87 g. $^1$H NMR (DMSO-$d_6$) 2.23 (s, 1H), 5.03 (s, 2H), 5.05 (s, 2H), 6.84-7.44 (m, 13H).

c) 2,5-Bis(benzyloxy)phenol

A solution of acetic acid 2,5-bis(benzyloxy)phenyl ester (1.85 g) and 5M sodium hydroxide solution (10.6 ml) in ethanol (11 ml) was heated under reflux for 6.5 hrs. After ethanol was evaporated under reduced pressure the clear solution was made acidic with diluted hydrochloric acid. The precipitated product was collected by filtration, washed with cold water and dried under reduced pressure. Yield is 0.56 g. $^1$H NMR (DMSO-$d_6$) δ=4.97 (s, 2H), 5.01 (s, 2H), 6.34 (dd, J=3.1, 8.8 Hz, 1H), 6.49 (d, J=3.1 Hz, 1H), 6.85 (d, J=8.8 Hz, 1H), 7.28-7.46 (m, 10H), 9.1 (br s, 1H).

d) 2-[2,5-Bis(benzyloxy)phenoxy]-1-phenylethanone

A mixture of 2,5-bis(benzyloxy)phenol (0.28 g), 2-bromoacetophenone (0.22 g), potassium hydrogen-carbonate (0.25 g) and 18-Crown-6 (3 mg) in acetonitrile (4.2 ml) was stirred at 22° C. for one week. The mixture was filtered and evaporated to dryness under reduced pressure. The residue was triturated with the mixture of ether (8.2 ml) and water (1.4 ml) at the ice bath temperature. The product was collected by filtration, washed with cold ether and dried under reduced pressure. Yield is 0.14 g. $^1$H NMR (DMSO-$d_6$) δ=4.98 (s, 2H), 5.06 (s, 2H), 5.58 (s, 2H), 6.51 (dd, J=8.9, 2.3 Hz, 1H), 6.68 (d, J=2.3 Hz, 1H), 6.94 (d, J=8.9 Hz, 1H), 7.28-8.03 (m, 15H).

e) 2-[2,5-Bis(benzyloxy)phenoxy]-1-phenylethanol

To the solution of 2-[2,5-bis(benzyloxy)phenoxy]-1-phenylethanone (0.14 g) in methanol (0.5 ml) and tetrahydrofuran (1.9 ml) was added at the 0° C. temperature sodium borohydride (6.5 mg). The reaction was stirred 15 minutes at 0° C. and 2 hrs at 22° C. temperature. After adding water (5 ml) methanol and tetrahydrofuran were evaporated off. After the residue was stirred at 22° C. 0.5 hr the product was filtered, washed with cold water and dried under reduced pressure. Yield is 0.09 g. $^1$H NMR (DMSO-$d_4$) δ=4.05 (m, 2H), 4.91 (m, 1H), 4.95 (s, 2H), 5.01 (s, 2H), 5.59 (d, J=4.7 Hz, 1H), 6.47 (dd, J=2.8, 8.8 Hz, 1H), 6.68 (d, J=2.8 Hz, 1H), 6.89 (d, J=8.8 Hz, 1H), 7.24-7.45 (m, 15H).

f) 2-(2-Hydroxy-2-phenylethoxy)benzene-1,4-diol

A solution of 2-[2,5-bis(benzyloxy)phenoxy]-1-phenylethanol (3.9 g) in ethanol (175 ml) was hydrogenated in the presence of 10% palladium on charcoal (100 mg) at 30 psi. The catalyst was removed by filtration and the solvent was evaporated under reduced pressure. The residue was recrystallized from the mixture of toluene-ethyl acetate 8:1 (15 ml). The yield of 2-(2-Hydroxy-2-phenylethoxy)-benzene-1,4-diol is 1.2 g. $^1$H NMR (DMSO-$d_6$) δ=3.79 (dd, J=9.6, 8.3 Hz, 1H), 4.00 (dd, J=9.6, 3.6 Hz, 1H), 4.94 (ddd, J=3.6, 8.3, 3.9 Hz, 1H), 5.66 (d, J=3.9 Hz, 1H), 6.18 (dd, J=8.5, 2.3 Hz, 1H), 6.34 (d, J=2.3, 1H), 6.57 (d, J=8.5 Hz, 1H), 7.26-7.47 (m, 5H), 7.97 (s, 1H), 8.66 (s, 1H).

g) 2,3-Dihydro-2-phenyl-benzo[1,4]dioxin-6-ol

A solution of 2-(2-hydroxy-2-phenylethoxy)benzene-1,4-diol (1.2 g) in toluene (75 ml) was heated with Amberlyst 15 catalyst (0.5 g) under reflux for 7 hrs. After filtering the solvent was evaporated under reduced pressure. The residue was purified by column chromatography on silica gel (toluene/ethyl acetate/acetic acid=8:1:1). The yield of 2,3-dihydro-2-phenyl-benzo[1,4]dioxin-6-ol is 0.5 g. $^1$H NMR (DMSO-$d_6$) δ=4.02 (dd, J=8.5, 11.4 Hz, 1H), 4.35 (dd, J=2.3, 11.4 Hz, 1H), 5.11 (dd, J=8.5, 2.3 Hz, 1H), 6.29 (dd, J=2.8, 8.5 Hz, 1H), 6.32 (d, J=2.8 Hz, 1H), 6.75 (d, J=8.5 Hz, 1H), 7.36-7.47 (m, 5H), 8.99 (s, 1H).

h) 2-(2,3-Dihydro-2-phenyl-benzo[1,4]dioxin-6-yloxy)-5-nitropyridine

A solution of 2,3-dihydro-2-phenyl-benzo[1,4]dioxin-6-ol (80 mg), 2-chloro-5-nitropyridine (56 mg) and potassium carbonate (52 mg) in dimethylformamide (1.0 ml) was stirred at 120° C. for 2 hrs. After cooling the mixture water (10 ml) was added and the precipitated product was filtered, washed with water and 2-propanol and dried under reduced pressure. Yield is 60 mg and mp 163-170° C. $^1$H NMR (DMSO-$d_6$) δ=4.16 (dd, J=8.5, 11.6 Hz, 1H), 4.47 (dd, J=11.6, 2.6 Hz, 1H), 5.28 (dd, J=2.6, 8.5 Hz, 1H), 6.75 (dd, J=2.6, 8.8 Hz, 1H), 6.88 (d, J=2.6 Hz, 1H), 7.05 (d, J=8.8 Hz, 1H), 7.21 (d, J=9.1 Hz, 1H), 7.39-7.52 (m, 5H), 8.60 (dd, J=2.8, 9.1 Hz, 1H), 9.05 (d, J=2.8 Hz, 1H).

Example 21

2-(2,3-Dihydro-2-phenyl-benzo[1,4]dioxin-6-yloxy-3-nitropyridine 2-(2,3-Dihydro-2-phenyl-benzo[1,4]dioxin-6-yloxy)-3-nitropyridine was prepared in the same way as 2-(2,3-dihydro-2-phenyl-benzo[1,4]dioxin-6-yloxy)-5-nitropyridine above from 2,3-dihydro-2-phenyl-benzo[1,4]dioxin-6-ol (80 mg) and 2-chloro-3-nitropyridine (56 mg). Yield is 30 mg and mp <60° C. $^1$H NMR (DMSO-$d_6$) δ=4.16 (dd, J=8.6, 11.4 Hz, 1H), 4.46 (dd, J=11.4, 2.5 Hz, 1H), 5.27 (dd, J=2.5, 8.6 Hz, 1H), 6.73 (dd, J=2.5, 8.6 Hz, 1H), 6.85 (d, J=2.5 Hz, 1H), 7.03 (d, J=8.6 Hz, 1H), 7.34-7.52 (m, 6H), 8.43 (dd, J=1.9, 4.8 Hz, 1H), 8.55 (dd, J=7.8, 1,9 Hz, 1H).

Example 22

2-(2,3-Dihydro-2-phenyl-benzo[1,4]dioxin-6-yloxy)-5-trifluoromethylpyridine 2-(2,3-dihydro-2-phenyl-benzo[1,4]dioxin-6-yloxy)5-trifluoromethylpyridine was prepared in the same way as 2-(2,3-dihydro-2-phenyl-benzo[1,4]dioxin-6-yloxy)-5-nitropyridine above from 2,3-dihydro-2-phenyl-benzo[1,4]dioxin-6-ol (80 mg) and 2-chloro-5-(trifluoromethyl)pyridine (64 mg). Yield is 50 mg and mp 104-110° C. $^1$H NMR (DMSO-$d_6$) δ=4.15 (dd, J=8.3, 11.4 Hz, 1H), 4.46 (dd, J=2.3, 11.4 Hz, 1H), 5.27 (dd, J=2.3, 8.3 Hz, 1H), 6.72 (dd, J=2.8, 8.8 Hz, 1H), 6.84 (d, J=2.8 Hz, 1H), 7.03 (d, J=8.8 Hz, 1H), 7.19 (d, J=8.8 Hz, 1H), 7.39-7.52 (m, 5H), 8.20 (dd, J=8.8, 2.6 Hz, 1H), 8.58 (d, J=2.6 Hz, 1H).

Example 23

5-Nitro-2-(6-phenyl-5,6,7,8-tetrahydro-naphthalen-2-yloxy)-pyridine a) 6-Methoxy-2-phenyl-3,4-dihydro-2H-naphthalen-1-one

A mixture of palladium(II) acetate (0.57 g), rac-2,2'-bis(diphenylphosphino)-1,1'-binaphtyl (1.91 g) and potassium tert-butoxide (4.15 g) in dry toluene was stirred under argon for 10 minutes. Bromobenzene (5.34 g) and 6-methoxy-1-tetralone (3.0 g) solvated in dry toluene were added and the mixture was stirred at 100° C. for 2 h. The reaction mixture was cooled to room temperature and poured into saturated aqueous ammonium chloride and extracted with ethyl ether. Organic extract was washed with brine, dried and evaporated. The crude product was purified by flash chromatography on silica gel using toluene and toluene-ethyl acetate (9:1) as an eluant. $^1$H NMR (400 MHz, d$_6$-DMSO) δ: 7.87 (d, 1H, J 7.8 Hz), 7.16-7.33 (m, 5H), 6.91-6.94 (m, 2H), 3.85 (s, 3H), 3.82-3.88 (m, 1H), 3.06-3.14 (m, 1H), 2.92-2.98 (m, 1H), 2.23-2.38 (m, 2H).

b)
6-Hydroxy-2-phenyl-3,4-dihydro-2H-naphthalen-1-one

6-Methoxy-2-phenyl-3,4-dihydro-2H-naphthalen-1-one (1.0 g) was refluxed with 47% HBr (20 ml) until disappearance of the starting material. The mixture was poured into water and extracted with ethyl acetate. Ethyl acetate was dried and evaporated. The product was recrystallised from toluene. $^1$H NMR (400 MHz, d$_6$-DMSO) δ: 10.35 (s, 1H), 7.79 (d, 1H, J 8.6 Hz), 7.15-7.33 (m, 5H), 6.75 (dd, 1H, J 8.6, 2.4 Hz), 6.68 (d, 1H, J 2.3 Hz), 3.79-3.85 (m, 1H), 2.99-3.06 (m, 1H), 2.83-2.90 (m, 1H), 2.19-2.33 (m, 2H).

c) 6-Phenyl-5,6,7,8-tetrahydro-naphthalen-2-ol

To a solution of 6-hydroxy-2-phenyl-3,4-dihydro-2H-naphthalen-1-one (50 mg) in trifluoroacetic acid was added triethylsilane (98 mg). The mixture was heated at 60° C. for 3 h. Solvent was evaporated, water added to the residue and the mixture extracted with ethyl acetate. Organic extract was dried and evaporated. $^1$H NMR (400 MHz, d$_6$-DMSO) δ: 9.02 (s, 1H), 7.18-7.32 (m, 5H), 6.87 (d, 1H, J 7.9), 6.50-6.53 (m, 2H), 2.68-2.92 (m, 5H), 1.94-1.99 (m, 1H), 1.81-1.89 (m, 1H).

d) 5-Nitro-2-(6-phenyl-5,6,7,8-tetrahydro-naphthalen-2-yloxy)-pyridine

6-Phenyl-5,6,7,8-tetrahydro-naphthalen-2-ol (30 mg), 2-chloro-5-nitropyridine (21 mg) and potassium fluoride (23 mg) in dry dimethylformamide were heated at 120° C. until disappearance of the starting material. Water and 1 N HCl were added and the mixture extracted with ethyl acetate. Ethyl acetate was washed with brine and water, dried and evaporated. The product was recrystallised from toluene. $^1$H NMR (400 MHz, d$_6$-DMSO) δ: 9.04 (d, 1H, J 2.4 Hz), 8.61 (dd, 1H, J 9.0, 2.5), 7.18-7.35 (m, 7H), 6.95-6.99 (m, 2H), 2.83-3.01 (m, 5H), 1.87-2.04 (m, 2H).

Example 24

6-(5-Nitro-pyridin-2-yloxy)-2-phenyl-3,4-dihydro-2H-naphthalen-1 one 6-(5-Nitro-pyridin-2-yloxy)-2-phenyl-3,4-dihydro-2H-naphthalen-1-one was prepared as described for 5-nitro-2-(6-phenyl-5,6,7,8-tetrahydro-naphthalen-2-yloxy)-pyridine in Example 23(d) using 50 mg 6-hydroxy-2-phenyl-3,4-dihydro-2H-naphthalen-1-one, 33 mg 2-chloro-5-nitropyridine and 37 mg potassium fluoride. $^1$H NMR (400 MHz, d$_6$-DMSO) δ: 9.07 (d, 1H, J 2.8 Hz), 8.68 (dd, 1H, J 9.0, 2.9), 8.01 (d, 1H, J 8.5), 7.37 (d, 1H, J 9.1 Hz), 7.21-7.38 (m, 7H), 3.96-4.04 (m, 1H), 3.15-3.23 (m, 1H), 2.98-3.04 (m, 1H), 2.39-2.48 (m, 1H), 2.25-2.31 (m, 1H).

Example 25

3-N-Acetylamino-4-(2-phenylchroman-6-yloxy)-anisole

3-Amino-4-(2-phenylchroman-6-yloxy)-anisole of Example 3 (0.174 g) was dissolved in 2 ml of dry pyridine under nitrogen. Acetic anhydride (0.15 ml) and 10 mol-% of 4-(N,N-dimethylamino)pyridine (DMAP) were added and the reaction solution was stirred for 2.5 hours at room temperature and quenched with addition of 1 ml of H$_2$O. Toluene was added into the reaction mixture and evaporated to dryness. Toluene evaporation was repeated. Product was purified by column chromatography (CH$_2$Cl$_2$:EtOAc/98:2). $^1$H-NMR (400 MHz; d$_6$-DMSO): δ 9.38 (s, 1H), 7.68 (s, 1H), 7.47-7.25 (m, 5H), 6.85-6.66 (m, 4H), 6.63 (dd, 1H, J=8.8 Hz, J=3.0 Hz), 5.07 (dd, 1H, J=9.9 Hz, J=1.9 Hz), 3.71 (s, 3H), 3.0-2.85 (m, 1H), 2.75-2.62 (s, 1H), 2.20-2.10 (m, 1H), 2.05 (s, 3H), 2.08-1.90 (m, 1H).

Example 26

5-Amino-2-(2-phenylchroman-6-yloxy-pyridine

5-Nitro-2-(2-phenylchroman-6-yloxy)-pyridine of Example 1 (2.26 g) was dissolved in 350 ml of glacial acetic acid. Zinc powder (8.48 g) was added in few portions due to exothermic reaction. The mixture was stirred at room temperature for 2 hours and filtered. The zinc was washed with glacial acetic acid. The acid was evaporated and toluene was added and evaporated again. A product mixture was dissolved in CH$_2$Cl$_2$ and washed with 1M NaOH. Water phase was further washed with CH$_2$Cl$_2$. Both organic fractions were combined and dried over Na$_2$SO$_4$. Product was purified by column chromatography. 1H-NMR (400 MHz; d$_6$-DMSO): δ 7.52 (d, 1H, J=2.8 Hz), 7.46-7.30 (m, 5H), 7.05 (dd, 1H, J=8.6 Hz, J=3.0 Hz), 6.82-6.72 (m, 3H), 6.69 (d, 1H, J=8.6 Hz), 5.08 (dd, 1H, J=10.0 Hz; J=2.1 Hz), 5.00 (s, 2H), 3.00-2.87 (m, 1H), 2.74-2.64 (m, 1H), 2.19-2.10 (m, 1H), 2.05-1.91 (m, 1H).

Example 27

5-N-Acetylamino-2-(2-phenylchroman-6-yloxy pyridine

5-Amino-2-(2-phenylchroman-6-yloxy)-pyridine of Example 26 (0.955 g) was dissolved in 8 ml of dry pyridine under nitrogen. DMAP (0.038 g) was added. AcCl (0.26 ml) was added at room temperature into the reaction solution dropwise because of vigorous and exothermic reaction. The reaction was stirred for 90 minutes at room temperature and quenched with slow addition of 1 ml of H$_2$O. 50 ml of toluene was added and evaporated to dryness. Toluene evaporation was repeated twice. Brownish product mixture was purified with column chromatography (EtOAc:CH$_2$Cl$_2$/60:40) to give of crystalline slightly yellowish product. The product was further purified with recrystallization from MeOH:H$_2$O (71: 29). The precipitate was filtered and washed with 2×10 ml of ice cold MeOH:H$_2$O (1:1). $^1$H-NMR (400 MHz; (d$_6$-DMSO): δ 10.04 (s, 1H), 8.27 (d, 1H, J=2.4 Hz), 8.01 (dd, 1H, J=8.9 Hz; J=2.8 Hz), 7.47-7.31 (m, 5H), 6.93 (d, 1H, J=8.9 Hz), 6.85 (d, 2H, J=6.8 Hz), 6.84 (s, 1H), 5.11 (dd, 1H, J=10.1 Hz; J=2.2 Hz), 3.02-2.90 (m, 1H), 2.71 (ddd, 1H, J=16.8 Hz; J=5.1 Hz, J=1.8 Hz), 2.22-2.11 (m, 1H), 2.08-1.92 (m, 1H).

Example 28

5-N,N-Diacetylamino-2-(2-phenylchroman-6-yloxy)-pyridine

5-Amino-2-(2-phenylchroman-6-yloxy)-pyridine of Example 26 (0.40 g) was dissolved in 1.5 ml of dry pyridine under nitrogen. DMAP (10 mol-%) and Ac$_2$O (1.0 ml) were added and the solution was stirred at room temperature for 2.5 hours. Toluene was added and evaporated to dryness. Toluene evaporation was repeated twice. Product was purified by column chromatography (EtOAc:CH$_2$Cl$_2$/60:40). $^1$H-NMR (400 MHz; d$_6$-DMSO): δ 8.05 (d, 1H, J=2.6 Hz), 7.78 (dd, 1H, J=8.7 Hz; J=2.6 Hz), 7.48-7.31 (m, 5H), 7.07 (d, 1H, J=8.9 Hz), 6.99-6.85 (m, 3H), 5.13 (dd, 1H, J=10.1 Hz; J=1.9 Hz), 3.05-2.92 (m, 1H), 2.78-2.70 (m, 1H), 2.21 (s, 6H), 2.25-2.12 (m, 1H), 2.08-1.94 (m, 1H).

Example 29

2-(2-Phenylchroman-6-yloxy)-aniline a) 2-Nitro-1-(2-phenylchroman-6-yloxy)-benzene

6-Hydroxyflavane (0.150 g) was dissolved in dry DMSO (5 ml) under nitrogen. KI (0.166 g) and KOH (0.074g) were added and solution was stirred at room temperature for 15 minutes. 2-Chloro-1-nitrobenzene (0.104 g) was added and the solution was stirred at +90° C. for 2.5 hours. Cooled solution was taken up with CH$_2$Cl$_2$ and washed with H$_2$O and 2M NaOH. Phases were separated and water phase was washed CH$_2$Cl$_2$. All organic phases were combined and washed with 1M HCl and then H$_2$O (until pH~7) and brine. Solution was dried over Na$_2$SO$_4$ and purified with filtration through the small silica column in CH$_2$Cl$_2$:n-heptane (60:40). $^1$H-NMR (300 MHz; d$_6$-DMSO): δ 8.01 (dd, 1H, J=8.1 Hz; J=1.7 Hz), 7.69 (m, 1H), 7.50-7.31 (m, 5H), 7.31-7.24 (m, 1H), 7.04 (dd, 1H, J=8.5 Hz; J=1.2 Hz), 6.92 (s, 1H), 6.90 (s, 2H), 5.12 (dd, 1H, J=10.1 Hz; J=2.3 Hz), 2.95 (ddd, 1H, J=16.9 Hz; J=11.2 Hz, J=5.8 Hz), 2.73 (ddd, 1H, J=16.9 Hz; J=3.2 Hz, J=1.7 Hz), 2.25-2.10 (m, 1H), 2.08-1.90 (m, 1H).

b) 2-(2-Phenylchroman-6-yloxy)-aniline

2-Nitro-1-(2-phenylchroman-6-yloxy)-benzene (0.160 g) was mostly dissolved in 30 ml of glacial acetic acid. Zinc powder (1.190 g) was added in few portions and the mixture was stirred for 90 minutes at room temperature. The zinc was filtered and washed with glacial acetic acid and evaporated. The evaporation residue was taken up with toluene and evaporated again. The residue was dissolved in CH$_2$Cl$_2$ and washed with 1M NaOH. NaOH solution was further washed with CH$_2$Cl$_2$. Both organic fractions were combined and dried over Na$_2$SO$_4$. The purification of the crude product was done by elution in CH$_2$Cl$_2$ through a small silica column. $^1$H-NMR (400 MHz; d$_6$-DMSO): δ 7.45-7.28 (m, 5H), 6.89-6.83 (m, 1H), 6.80 (d, 1H, J=8.5 Hz), 6.77 (dd, 1H, J=8.0 Hz; J=1.7 Hz), 6.73-6.67 (m, 3H), 6.54-6.48 (m, 1H), 5.06 (dd, 1H, J=10.1 Hz; J=2.3 Hz), 4.85 (s, 2H), 2.99-2.87 (m, 1H), 2.73-2.61 (m, 1H), 2.19-2.09 (m, 1H), 2.03-1.90 (m, 1H).

Example 30

5-Trifluoromethyl-2-(2-phenylchroman-6-yloxy)-aniline a) 2-Nitro-1-(2-phenylchroman-6-yloxy)-4trifluoromethylbenzene

2-Nitro-1-(2-phenylchroman-6-yloxy)-4-trifluoromethylbenzene was prepared as described for $^2$-nitro-1-(2-phenylchroman-6-yloxy)-benzene in Example 29(a) except that 6-hydroxyflavane (0.339 g) was used in 7 ml of dry DMSO under nitrogen. Also KI (0.374 g) and KOH (0.168 g) and 4-chloro-3-nitro-1-trifluoromethylbenzene (0.24 ml) were added in similar manner. Product was purified by column chromatography (CH$_2$Cl$_2$:n-heptane/60:40). $^1$H-NMR (300 MHz; d$_6$-DMSO): δ 8.44 (d, 1H, J=2.1 Hz), 7.99 (dd, 1H, J=9.0 Hz; J=2.2 Hz), 7.51-7.29 (m, 5H), 7.15 (d, 1H, J=8.7 Hz), 7.09-6.91 (m, 3H), 5.15 (dd, 1H, J=10.1 Hz; J=2.3 Hz), 3.08-2.90 (m, 1H), 2.83-2.68 (m, 1H), 2.25-2.11 (m, 1H), 2.09-1.91 (m, 1H).

b) 5-Trifluoromethyl-2-(2-phenylchroman-6-yloxy)-aniline

2-Nitro-1-(2-phenylchroman-6-yloxy)-4-trifluoromethylbenzene (0.311 g) was reduced in 25 ml of glacial acetic acid with zinc (1.48 g) as described for 2-(2-phenylchroman-6-yloxy)-aniline in Example 29. Product was purified by column chromatography (CH$_2$Cl$_2$:n-heptane/70:30 as the eluant). $^1$H-NMR (300 MHz; d$_6$-DMSO): δ 7.48-7.28 (m, 5H), 7.06 (d, 1H, J=2.2 Hz), 6.86 (dd, 1H, J=7.8 Hz, J=1.5 Hz), 6.85-6.56 (m, 3H), 6.72 (d, 1H, J=8.4 Hz), 5.40 (s, 2H), 5.10 (dd, 1H, J=10.0 Hz; J=2.3 Hz), 3.04-2.87 (m, 1H), 2.78-2.65 (m, 1H), 2.24-2.10 (m, 1H), 2.08-1.89 (m, 1H).

Example 31

5-Amino-2-(2-phenylchroman-6-yloxy)-aniline a) 2,4-Dinitro-1-(2-phenylchroman-6-yloxy)-benzene 2,4-Dinitro-1-(2-phenylchroman-6-yloxy)-benzene was prepared as described for 2-nitro-1-(2-phenylchroman-6-yloxy)-benzene in Example 29(a) except that 6-hydroxyflavane (0.226 g) was used in 5 ml of dry DMSO under nitrogen. Also KI (0.249 g) and KOH (0.112g) and 2,4-dinitrochlorobenzene (0.210 mg) were added in similar manner. Product was purified by column chromatography (CH$_2$Cl$_2$:n-heptane/75:25 as the eluant). $^1$H-NMR (400 MHz; d$_6$-DMSO): δ 8.88 (d, 1H, J=2.8 Hz), 8.45 (dd, 1H, J=9.4 Hz, J=2.9 Hz), 7.48-7.30 (m, 5H), 7.14 (d, 1H, J=9.3 Hz), 7.10 (d, 1H, J=2.8 Hz), 7.05 (dd, 1H, J=8.8 Hz, J=2.9 Hz), 6.98 (d, 1H, J=8.7 Hz), 5.16 (dd, 1H, J=10.2 Hz, J=2.1 Hz), 3.08-2.93 (m, 1H), 2.83-2.71 (m, 1H), 2.25-2.13 (m, 1H), 2.08-1.94 (m, 1H).

b) 5-Amino-2-(2-phenylchroman-6-yloxy)-aniline 2,4-Dinitro-1-(2-phenylchroman-6-yloxy)-benzene (0.04 g) was dissolved in 12 ml of glacial acetic acid and zinc (0.131 g) was added. The reaction stirred at room temperature for 30 minutes. Workup was done as described for 2-(2-phenylchroman-6-yloxy)-aniline in Example 29. Product was purified by column chromatography (CH$_2$Cl$_2$:Et$_3$N /96:4 as the eluant). $^1$H-NMR (300 MHz; d$_6$-DMSO): δ 7.48-7.28 (m, 5H), 6.74 (d, 1H, J=8.8 Hz), 6.63 (dd, 1H, J=8.8 Hz, J=2.9 Hz), 6.57 (d, 1H, J=2.8 Hz), 6.49 (d, 1H, J=8.4 Hz), 6.02 (d, 1H, J=2.6 Hz), 5.81 (dd, 1H, J=8.4 Hz, J=2.6 Hz), 5.03 (dd, 1H, J=10.0 Hz, J=2.3 Hz), 4.62 (s, 2H), 4.48 (s, 2H), 2.99-2.82 (m, 1H), 2.71-2.57 (m, 1H), 2.20-2.06 (m, 1H), 2.03-1.86 (m, 1H)

Example 32

5-Cyano-2-(2-phenylchroman-6-yloxy)-aniline a) 4-Cyano-2-nitro-1-(2-phenylchroman-6-yloxy)-benzene 4-Cyano-2-nitro-1-(2-phenylchroman-6-yloxy)-benzene was prepared as described for 2-nitro-1-(2-phenylchroman-6-yloxy)-benzene in Example 29(a) except that 6-hydroxy-flavane (0.453 g) was used in 10 ml of dry DMSO under nitrogen. Also KI (0.498 g) and KOH (0.224 g) and 4-chloro-3-nitro benzonitrile (0.365 mg) were added in similar manner. Product was purified by column chromatography ($CH_2Cl_2$:n-heptane/90:10 as the eluant). $^1$H-NMR (400 MHz; $d_6$-DMSO): δ 8.64 (d, 1H, J=2.0 Hz), 8.06 (dd, 1H, J=8.8 Hz, J=2.1 Hz), 7.08 (d, 1H, J=8.8 Hz), 7.07-6.93 (m, 3H), 5.15 (dd, 1H, J=10.1 Hz, J=2.1 Hz), 3.05-2.91 (m, 1H), 2.82-2.70 (m, 1H), 2.24-2.12 (m, 1H), 2.08-1.92 (m, 1H).

b) 5-Cyano-2-(2-phenylchroman-6-yloxy)-aniline

4-Cyano-2-nitro-1-(2-phenylchroman-6-yloxy)-benzene (0.155 g; 0.4 mmol) was reduced to the corresponding aniline as described for 2-(2-phenylchroman-6-yloxy)-aniline in Example 29 except that 40 ml of glacial acetic acid and 0.93 g of zinc powder were used. Product was purified by column chromatography (100% $CH_2Cl_2$ as the eluant). $^1$H-NMR (300 MHz; $d_6$-DMSO): δ 7.57-7.28 (m, 5H), 7.06 (d, 1H, J=2.0 Hz), 6.95-6.78 (m, 4H), 6.65 (d, 1H, J=8.3 Hz), 5.46 (s, 2H), 5.11 (dd, 1H, J=10.0 Hz, J=2.1 Hz), 3.03-2.88 (m, 1H), 2.78-2.66 (m, 1H), 2.23-2.10 (m, 1H), 2.08-1.89 (m, 1H).

Example 33

N-Acetyl-2-(2-Penylchroman-6-yloxy)-aniline 2-(2-Penylchroman-6-yloxy)-aniline (0.093 g) was dissolved in 1 ml of dry pyridine under nitrogen. DMAP (10 mol-%) and acetic acid anhydride (0.1 ml) were added and the solution was stirred for 4 hours at room temperature followed with quenching with 0.5 ml of $H_2O$. The solution was evaporated to dryness and toluene was added and evaporated again. Toluene evaporation was repeated. Product was purified by column chromatography ($CH_2Cl_2$:i-PrOH/98:2 as the eluant) and recrystallized from 0.5 ml of heated absolute ethanol by cooling and adding 0.5 ml of $^1$H-NMR (400 MHz; $d_6$-DMSO): δ 9.43 (s, 1H), 7.96 (m, 1H), 7.48-7.30 (m, 5H), 7.08-6.99 (m, 2H), 6.89-6.74 (m, 4H), 5.10 (dd, 1H, J=9.9, J=2.0), 3.03-2.88 (m, 1H), 2.76-2.65 (m, 1H), 2.21-2.11 (m, 1H), 2.10-1.91 (m, 1H), 2.06 (s, 3H).

Example 34

3-Nitro-2-(2-phenylchroman-6-yloxy)-pyridine

6-Hydroxyflavane (0.150 g) was dissolved in 3 ml of dry DMF under nitrogen. KF (0.117 g) was added and the solution was stirred for 30 minutes at +120° C. The solution was cooled a bit and 2-chloro-3-nitropyridine was added (0.212 g) and stirred for 7 hours at +120° C. and overnight at room temperature. The reaction mixture was taken up with EtOAc and 1M HCl and water were added and phases separated. Organic phase was washed with water and pH was adjusted to 7 with 1M NaOH. Organic phase was washed with water, brine and dried over $Na_2SO_4$. Product was purified by column chromatography ($CH_2Cl_2$:n-heptane/80:20). $^1$H-NMR (400 MHz; $d_6$-DMSO): δ 8.55 (dd, 1H, J=7.9 Hz, J=1.7 Hz), 8.42 (dd, 1H, J=4.9 Hz, J=1.7 Hz), 7.51-7.29 (m, 6H), 7.02-6.92 (m, 2H), 6.88 (d, 1H, J=8.7 Hz), 5.14 (dd, 1H, J=10.0 Hz, J=2.1 Hz), 3.05-2.92 (m, 1H), 2.78-2.68 (m, 1H), 2.22-2.13 (m, 1H), 2.07-1.95 (m, 1H).

Example 35

3-Amino-5-(trifluoromethyl)-2-(2-phenylchroman-6-yloxy)-aniline a) 2,6-Dinitro-1-(2-phenylchroman-6-yloxy)-4-trifluoromethylbenzene 2,6-Dinitro-1-(2-phenylchroman-6-yloxy)-4-trifluoromethylbenzene was prepared as described for 2-nitro-1-(2-phenylchroman-6-yloxy)-benzene in Example 29(a) except that 6-hydroxyflavane (0.453 g) was used in 10 ml of dry DMSO under nitrogen. Also KI (0.498 g) and KOH (0.224 g) and 4-chloro-3,5-dinitro benzotrifluoride (0.541 mg) were added in similar manner. $^1$H-NMR (400 MHz; $d_6$-DMSO): δ 8.87 (s, 2H), 7.46-7.29 (m, 5H), 6.89-6.75 (m, 4H), 5.09 (dd, 1H, J=10.3 Hz, J=2.1 Hz), 2.98-2.85 (m, 1H), 2.75-2.62 (m, 1H), 2.19-2.08 (m, 1H), 2.03-1.88 (m, 1H).

b) 3-Amino-5-(trifluoromethyl)-2-(2-phenylchroman-6-yloxy)-aniline 2,6-Dinitro-1-(2-phenylchroman-6-yloxy)-4-trifluoromethylbenzene (0.198 g; 0.43 mmol) was reduced to corresponding diamino compound as described for 2-(2-phenylchroman-6-yloxy)-aniline in Example 29 except that 25 ml of glacial acetic acid and 1.525 g of metallic zinc powder were used. Product was purified by column chromatography (100% $CH_2Cl_2$ as the eluant). $^1$H-NMR (400 MHz; $d_6$-DMSO): δ 7.45-7.28 (m, 5H), 6.76 (d, 1H, J=8.8 Hz), 6.65 (dd, 1H, J=8.7 Hz, J=3.0 Hz), 6.62 (d, 1H, J=2.8 Hz), 5.04 (dd, 1H, J=10.0 Hz, J=2.1 Hz), 4.98 (s, 4H), 2.98-2.86 (m, 1H), 2.70-2.60 (m, 1H), 2.18-2.09 (m, 1H), 2.00-1.88 (m, 1H).

Example 36

5-Succinimido-2-(2-phenylchroman-6-yloxy)-pyridine

5-Amino-2-(2-phenylchroman-6-yloxy)-pyridine of Example 26 (0.16 g) was dissolved in 7.5 ml of glacial acetic acid under nitrogen. Succinic anhydride (0.0563 g) was added and the solution refluxed 60 minutes and solution was cooled and evaporated to dryness. Toluene (25 ml) was added and evaporated again to dryness. Product was purified by column chromatography ($CH_2Cl_2$:i-PrOH/95:5 as the eluant. $^1$H-NMR (400 MHz; $d_6$-DMSO): δ 8.03 (d, 1H, J=2.6 Hz), 7.73 (dd, 1H, J=8.7 Hz, J=2.6 Hz), 7.48-7.31 (m, 5H), 7.10 (d, 1H, J=8.7 Hz), 6.95 (d, 1H, J=2.6 Hz), 6.92 (dd, 1H, J=8.7 Hz, J=2.7 Hz), 6.88 (d, 1H, J=8.6 Hz), 5.13 (dd, 1H, J=10.2 Hz, J=2.2 Hz), 3.05-2.92 (m, 1H), 2.84-6.68 (m, 1H), 2.79 (s, 4H), 2.22-2.12 (m, 1H), 2.08-1.93 (m, 1H).

Example 37

5-(O,O'-Diacetyl-L-tartaricimido)-2-(2-phenylchroman-6-yloxy)-pyridine 5-(O,O'-Diacetyl-L-tartaricimido)-2-(2-phenylchroman-6-yloxy)-pyridine was prepared as described for 5-succinimido-2-(2-phenylchroman-6-yloxy)-pyridine in Example 36 except that 5-amino-2-(2-phenylchroman-6-yloxy)-pyridine (0.318 g) and (+)-diacetyl-L-tartaric acid anhydride (0.227 g) were refluxed in 15 ml of glacial acetic acid for 60 minutes. $^1$H-NMR (400 MHz; $d_6$-DMSO): δ 8.10 (d, 1H, J=2.6 Hz), 7.79 (dd, 1H, J=8.7 Hz, J=2.6 Hz), 7.49-7.30 (m, 5H), 7.13 (d, 1H, J=8.8 Hz), 6.97 (d, 1H, J=2.5 Hz), 6.93 (dd, 1H, J=8.7 Hz, J=2.7 Hz), 6.88 (d, 1H, J=8.7 Hz), 6.08 (s, 2H), 5.13 (dd, 1H, J=10.1 Hz, J=1.9 Hz), 3.06-2.92 (m, 1H), 2.80-2.69 (m, 1H), 2.23-2.12 (m, 1H), 2.18 (s, 6H), 2.08-1.93 (m, 1H).

Example 38

5-Nitro-2-(2-phenylindan-5-yloxy)-pyridine a) 3-(4-Methoxyphenyl)-2-phenylacrylic Acid

Triethylamine was added to solution of p-anisaldehyde (10 g) and phenylacetic acid (10 g) in acetic anhydride (25 ml). Reaction mixture was stirred at 90° C. for 8 h. Reaction mixture was cooled and water (600 ml) solution of potassium carbonate (81 g) was added. After addition reaction mixture was heated at 60° C. for an hour. Before neutralising with concentrated hydrochloric acid the reaction mixture was cooled below 10° C. Precipitate was filtered and washed with water. $^1$H-NMR (400 MHz, $d_6$-DMSO): 12.6 (bs, 1H), 7.67 (s, 1H), 7.4-7.3 (m, 3H), 7.2-7.1 (m, 2H), 7.0-6.9 (m, 2H), 6.8-6.7 (m, 2H), 3.70 (s, 3H). (M)$^+$=254 (100%).

b) 3-(4-Methoxyphenyl)-2-phenylpropionic Acid 13 g of 3-(4-methoxyphenyl)-2-phenylacrylic acid was dissolved to 600 ml of ethyl acetate and 2.6 g of 10% palladium on charcoal was added under inert atmosphere. Starting material was hydrogenated at room temperature to give quantitative yield of 3-(4-methoxyphenyl)-2-phenylpropionic acid. $^1$H-NMR (400 MHz, $d_6$-DMSO): 12.3 (bs, 1H), 7.32-7.20 (m, 5H), 7.1-7.0 (m, 2H), 6.8-6.7 (m, 2H), 3.79 (dd, 1H, J 6.9, 8.7 Hz), 3.70 (s, 3H), 3.22 (dd, 1H, J 8.7, 13.7 Hz), 2.87 (dd, 1H, J 6.9, 13.7 Hz).

c) 6-Methoxy-2-phenylindan-1-one

To solution of 3-(4-methoxyphenyl)-2-phenylpropionic acid (4.6 g) in dry methylenechloride (26 ml) was added two drops of dry DMF. Thionylchloride (3 ml) was added and reaction mixture was stirred at 40° C. for 4 h. Solvent was evaporated under vacuum. Precipitate was dissolved to methylenechloride. Solution was cooled to 0-3° C. This solution and aluminium chloride (2.5g) were mixed slowly over 4 hours keeping temperature under 4° C. After mixing reaction mixture was stirred at room temperature for 2 h. Reaction was quenched by pouring to dilute ice cold hydrochloric acid. Layers were separated and water solution was extracted with methylenechloride. Combined organic layers were washed with water, dried and evaporated. Crude product was triturated to give 2.9 g of 6-Methoxy-2-phenylindan-1-one. $^1$H-NMR (400 MHz, $d_6$-DMSO): 7.56 (d, 1H), 7.35-7.23 (m, 4H), 7.18-7.13 (m, 3H), 4.02 (dd, 1H, J 3.9, 8.0 Hz), 3.82 (s, 3H), 3.61 (dd, 1H, J 8.0, 17.2 Hz), 3.11 (dd, 1H, J 3.9, 17.2 Hz).

d) 5-Methoxy-2-phenylindane

5-Methoxy-2-phenylindane was prepared as described for 2-phenylchroman-6-ol in Example 1(a) using 600 mg of 6-methoxy-2-phenylindan-1-one. $^1$H-NMR (400 MHz, $d_6$-DMSO): 7.32-7.27 (m, 4H), 7.21-7.18 (m, 1H), 7.13 (d, 1H, J 8.2 Hz), 6.83 (d, 1H, J 2.4 Hz), 6.72 (dd, 1H, J 2.4, 8.2 Hz), 3.72 (s, 3H), 3.64 (k, 1H, J 8.5 Hz), 3.23 (dt, 2H, J 8.5, 15.9 Hz), 2.92 (m, 2H).

e) 2-Phenylindan-5-ol

Mixture of 5-methoxy-2-phenylindane (200 mg) and concentrated HBr (4 ml) was refluxed for 5.5 h. Reaction mixture was allowed to cool to room temperature and 20 ml of ice water and it was extracted with methylenechloride. The combined organic layers were washed with brine and dried with $Na_2SO_4$. The solvents were evaporated to give 2-phenylindan-5-ol. $^1$H-NMR (400 MHz, $d_6$-DMSO): 9.05 (bs, 1H), 7.3-7.28 (m, 4H), 7.26-7.15 (m, 1H), 7.0 (d, 1H, J 8.1 Hz), 6.64 (d, 1H, J 1.9 Hz), 6.55 (dd, 1H, J 1.9, 8.1 Hz), 3.60 (k, 1H, J 8.6 Hz), 3.18 (m, 2H), 2.86 (dt, 2H, J 8.6, 16 Hz).

f) 5-Nitro-2-(2-phenylindan-5-yloxy)pyridine

5-Nitro-2-(2-phenylindan-5-yloxy)pyridine was prepared as described for 2-phenylchroman-6-yloxy)pyridine in Example 1(b) using 107 mg of 2-phenylindan-5-ol. $^1$H-NMR (400 MHz, $d_6$-DMSO): 9.04 (d, 1H, J 2.9 Hz), 8.61 (dd, 1H, J 2.9, 9.1 Hz), 7.38-7.28 (m, 5H), 7.24-7.20 (m, 2H), 7.11 (d, 1H, J 2.2 Hz), 7.00 (dd, 1H, J 2.2, 8.0 Hz), 3.72 (k, 1H, J 8.9 Hz), 3.36-3.28 (m, 2H), 3.01 (dd, 2H, J 8.9, 15.3 Hz).

Example 39

5-Methoxy-2-(2-phenylindan-5-yloxy)phenylamine a) 5-(4-Methoxy-2-nitrophenoxy)-2-phenylindane 5-(4Methoxy-2-nitrophenoxy)-2-phenylindan was prepared as described for 6-(4-methoxy-2-nitrophenoxy)-2-phenylchroman in Example 3(a) using 575 mg of 2-phenylindan-5-ol. $^1$H-NMR (400 MHz, $d_6$-DMSO): 7.60 (d, 1H, J 3.1 Hz), 7.35-7.28 (m, 5H), 7.25-7.16 (m, 3H), 6.86 (d, 1H, J 2.3 Hz), 6.78 (dd, 1H, J 2.3, 8.2 Hz), 3.84 (s, 3H), 3.67 (k, 1H, J 8.3 Hz), 3.25 (dd, 2H, J 8.3, 15.7 Hz), 2.95 (m, 2H). (M)$^+$=361 (60%), 209 (100%)

b) 5-Methoxy-2-(2-phenylindan-5-yloxy)phenylamine

5-Methoxy-2-(2-phenylindan-5-yloxy)phenylamine was prepared as described for 5-methoxy-2-(2-phenylchroman-6-yloxy)phenylamine in Example 3(b) using 200 mg of 5-(4-methoxy-2-nitrophenoxy)-2-phenylindane. $^1$H-NMR (400 MHz, $d_6$-DMSO): 7.33-7.27 (m, 4H), 7.23-7.18 (m, 2H), 6.82 (d, 1H, J 8.4 Hz), 6.81 (s, 1H), 6.77 (dd, 1H, J 2.3, 8.4 Hz), 6.69 (d, 1H, J 2.3 Hz), 6.48 (bd, 1H, J 6.4 Hz), 3.71 (s, 3H), 3.66 (k, 1H, J 8.3 Hz), 3.24 (dd, 2H, J 8.3, 15.6 Hz), 2.93 (m, 2H). (M)$^+$=331 (100%)

Example 40

2-[2-(3-Fluorophenyl)-indan-5-yloxy]-5-methoxyphenylamine a) 2-(3-Fluorophenyl)indan-5-ol 2-(3-Fluorophenyl)indan-5-ol was prepared as described for 2-phenylindan-5-ol in Example 25(a-e) using 5 g of 3-fluorophenylacetic acid. $^1$H-NMR (400 MHz, d$_6$-DMSO): 9.09 (s, 1H), 7.37-7.29 (m, 1H), 7.14-7.7.09 (m, 2H), 7.02-6.98 (m, 2H), 6.64 (d, 1H, J 1.7 Hz), 6.55 (dd, 1H, J 2.3, 8.1 Hz), 3.63 (k, 1H, J 8.3 Hz), 3.24-3.12 (m, 2H), 2.94-2.79 (m, 2H).

b) 5-Methoxy-2-[2-(3-fluorophenyl)indan-5-yloxy]phenylamine

5-Methoxy-2-[2-(3-fluorophenyl)indan-5-yloxy]phenylamine was prepared as described for 5-methoxy-2-(2-phenylchroman-6-yloxy)phenylamine in Example 3(a-b) using 500 mg of 2-(3-fluorophenyl)indan-5-ol. $^1$H-NMR (400 MHz, CDCl$_3$): 7.26-7.21 (m, 1H), 7.16 (d, 1H, J 2.9 Hz), 7.09 (d, 1H, J 8.2 Hz), 7.02 (d, 1H, J 7.7 Hz), 6.96-6.88 (m, 4H), 6.83 (d, 1H, J 9.1 Hz), 6.72 (dd, 1H, J 2.9, 9.1 Hz), 3.69 (s, 3H), 3.65 (k, 1H, J 8.8 Hz), 3.26-3.19 (m, 2H), 2.94 (dd, 2H, J 8.8, 15.1 Hz).

Example 41

2-(2-Phenylindan-5-yloxy)phenylamine a) 5-(2-Nitrophenoxy)-2-phenylindane 5-(2-nitrophenoxy)-2-phenylindane was prepared as described for 6-(4-methoxy-2-nitrophenoxy)-2-phenylchroman in Example 3(a) using 200 mg 2-phenylindan-5-ol and 150 mg of 1-chloro-2-nitrobenzene. $^1$H-NMR (400 MHz, d$_6$-DMSO): 8.04 (dd, 1H, J 1.6, 8.3 Hz), 7.68 (ddd, 1H, J 1.6, 7.4, 8.3 Hz), 7.36-7.27 (m, 6H), 7.24-7.17 (m, 1H), 7.11 (dd, 1H, J 1.1, 8.4 Hz), 6.98 (bd, 1H, J 2.3 Hz), 6.89 (dd, 1H, J 2.3, 8.1 Hz), 3.69 (k, 1H, J 8.5 Hz), 3.28 (dd, 2H J 8.5, 15.8 Hz), 3.05-2.95 (m, 2H).

b) 2-(2-Phenylindan-5-yloxy)phenylamine 2-(2-Phenylindan-5-yloxy)phenylamine was prepared as described for 2-(2-phenylchroman-6yloxy)-phenylamine in Example 29(b) using 170 mg of 5-(2-nitrophenoxy)-2-phenylindane. $^1$H-N (400 MHz, d$_6$-DMSO): 7.32-7.27 (m, 4H), 7.23-7.16 (m, 2H), 6.92-6.87 (m, 1H), 6.81-6.71 (m, 4H), 6.56-6.53 (m, 1H), 4.85 (bs, 2H), 3.65 (k, 1H, J 8.3 Hz), 3.23 (dd, 2H, J 8.3, 15.5 Hz), 2.97-2.88 (m, 2H).

Example 42

2-(2-Phenylindan-5-yloxy)-5-trifluoromethylbenzene-1,3-diamine a) 5-(2,6-Dinitro-4-trifluoromethylphenoxy)-2-phenylindan

Potassium-t-butoxide (117 mg) was added into a solution of 2-phenylindan-5-ol (200 mg) in dry DMF (3 ml). After stirring resulting mixture at room temperature for 30 min 4-chloro-3,5-dinitrobenzotrifluoride (275 mg) was added. Reaction mixture was stirred for a further three hours at 150° C. After cooling into room temperature water and ethyl acetate was added into the mixture. 1 M Hydrochloric acid was added into water layer and the solution was extracted with ethyl acetate. Combined organic layers were washed with water and brine, dried with Na$_2$SO$_4$ and evaporated. 5-(2,6-Dinitro-4-trifluoromethylphenoxy)-2-phenylindan was recrystallised from ethanol. $^1$H-NMR (400 MHz, d$_6$-DMSO): 8.89 (s, 2H), 7.33-7.27 (m, 4H), 7.23-7.18 (m, 2H), 6.96 (d, 1H, J 2.5 Hz), 6.83 (dd, 1H, J 2.5, 8.2 Hz), 3.67 (k, 1H, J 8.6 Hz), 3.27-3.19 (m, 2H), 2.97-2.89 (m, 2H).

b) 2-(2-Phenylindan-5-yloxy)-5-trifluoromethylbenzene-1,3-diamine 2-(2-Phenylindan-5-yloxy)-5-trifluoromethylbenzene-1,3-diamine was prepared as described for 2-(2-phenylchroman-6-yloxy)-5-trifluoromethylbenzene-1,3-diamine in Example 35(b) using 230 mg of 5-(2,6-dinitro-4-trifluoromethylphenoxy)-2-phenylindan. $^1$H-NMR (300 MHz, d$_6$-DMSO): 7.33-7.27 (m, 4H), 7.22-7.18 (m, 1H), 7.14 (d, 1H, J 8.1 Hz), 6.73-6.69 (m, 2H), 6.31 (s, 2H), 4.98 (s, 4H), 3.64 (k, 1H, J 8.5 Hz), 3.26-3.18 (m, 2H), 2.96-2.86 (m, 2H).

Example 43

6-(5-Nitropyridin-2-yloxy)-2-phenylchroman-4-ylamine a) 6-Hydroxy-2-phenylchroman-4-one Oxime

Sodium hydroxide (122 mg) was added into a cooled solution of 6-hydroxyflavanone (2 g) and hydroxylamine hydrochloride (900 mg) in ethanol (5 ml) and water (2 ml). Resulting mixture was refluxed for 6 hours and hydroxylamine hydrochloride (450 mg) and sodium hydroxide (61 mg) were added after every 45 min. After cooling into room temperature water (23 ml) and concentrated hydrochloric acid (5.6 ml) were added into the mixture. Precipitate was filtered, washed with water and dried in vacuum. $^1$H-NMR (400 MHz, d$_6$-DMSO): 11.3 (s, 1H), 9.11 (s, 1H), 7.50-7.48 (m, 2H), 7.43-7.33 (m, 3H), 7.21 (d, 1H, J 2.9 Hz), 6.80 (d, 1H, J 8.8 Hz), 6.72 (dd, 1H, J 2.9, 8.8 Hz), 5.07 (dd, 1H, J 3.2, 11.9 Hz), 3.28 (dd, 1H, J 3.2, 17.1 Hz), 2.64 (dd, 1H, J 11.9, 17.1 Hz).

b) 4-Amino-2-phenylchroman-6-ol

A solution of 6-hydroxy-2-phenylchroman-4-one oxime (2.07 g) in 1,2-dimethoxy ethane (20 ml) was added into a cooled solution of titanium(IV)chloride (1.9 ml) and sodium borohydride (1.29 g) in 1,2-dimethoxy ethane (20 ml). Resulting mixture was stirred for a further 4 hours at room temperature. Reaction was quenched with ice and pH was adjusted to 2-3. Resulting mixture was extracted with toluene. Water layer was made alkaline with solution of sodium hydroxide. Dark precipitate was filtered and washed with methanol. Methanol washings were evaporated to dryness, dissolved to water and neutralised and finally precipitate was filtered. Mixture of diastereomers of 4-amino-2-phenylchroman-6-ol was isolated as its hydrochloride salt. (M)$^+$=241 (4.4%), 224 (10%), 137 (100%).

c) 6-(5-Nitropyridin-2-yloxy)-2-phenylchroman-4-ylamine 6-(5-Nitropyridin-2-yloxy)-2-phenylchroman-4-ylamine was prepared as described for 2-phenylchroman-6-yloxy)pyridine in Example 1(b) using 100 mg of hydrochloride salt of 4-amino-2-phenylchroman-6-ol. Mixture of diastereomers of 6-(5-nitropyridin-2-yloxy)-2-phenylchroman-4-ylamine was isolated as its hydrochloride salt.(M)$^+$=363 (22%), 259 (100%), 242 (70%), 224 (64%), 223 (62%).

Example 44

N-[6-(5-Nitropyridin-2-yloxy)-2-phenylchroman-4-yl]-acetamide

Acetic anhydride (60 µl) was added into a cooled solution of 6-(5-nitropyridin-2-yloxy)-2-phenylchroman-4-ylamine hydrochloride (100 mg) and pyridine (41 µl) in dry DMF. Resulting mixture was stirred for a further 20 hours at 0° C. Reaction was quenched with ice water and neutralised. Resulting mixture was extracted with dichloromethane, dried with $Na_2SO_4$ and evaporated. Mixture of diastereomers of N-[6-(5-nitropyridin-2-yloxy)-2-phenylchroman-4-yl]-acetamide was recrystallised from dichloromethane. (M)$^+$=405 (24%), 301 (14%), 259 (100%), 242 (55%), 224 (96%).

Example 45

Dimethyl-[6-(5-nitropyridin-2-yloxy)-2-phenylchroman-4-yl]-amine a) 4-N,N-Dimethylamino-2-phenylchroman-6-ol Sodium cyanoborohydride (274 mg) was added into a solution of free base of 4-amino-2-phenylchroman-6-ol (263 mg) and 37% formaldehyde (1.4 ml) in acetonitrile (15 ml). After 30 min pH was adjusted to 6-7 with acetic acid. Resulting mixture was stirred at room temperature over night. Reaction mixture was evaporated to dryness, precipitate was dissolved to 10% solution of potassium hydroxide and extracted with methylene chloride. Combined organic layers were dried and evaporated to give 4-N,N-dimethylamino-2-phenylchroman-6-ol as mixture of diastereomers. $^1$H-NMR (400 MHz, $d_6$-DMSO): 8.79 (bs, 1H, major and minor), 7.5-7.3 (m, 5H, major and minor), 6.96 (d, 1H, J 2.8 Hz, major), 6.75 (d, 1H, J 2.9 Hz, minor), 6.69 (d, 1H, 8.7 Hz, minor), 6.63-6.60 (m, 1H, major and minor), 6.53 (dd, 1H, J 2.8, 8.7 Hz, major), 5.17 (dd, 1H, J 2.7, 9.7 Hz, minor), 5.04 (d, 1H, J 10.7 Hz, major), 4.17 (dd, 1H, J 5.7, 11.4 Hz, major), 3.35 (m, 1H, minor), 2.24 (s, 3H, minor), 2.21 (s, 3H, major), 2.2-1.7 (m, 2H, major and minor).

b) Dimethyl-[6-(5-nitropyridin-2-yloxy)-2-phenyl-chroman-4-yl]-amine

N,N-Dimethyl-[6-(5-nitropyridin-2-yloxy)-2-phenylchroman-4-yl]-amine was prepared as described for 2-phenylchroman-6-yloxy)pyridine in Example 1(b) using 220 mg of 4-N,N-dimethylamino-2-phenylchroman-6-ol. N,N-Dimethyl-[6-(5-nitropyridin-2-yloxy)-2-phenylchromanyl-4-yl]-amine was isolated as a mixture of diastereomers. (M)$^+$=391 (8%), 347 (8%), 346 (8%), 287 (68%), 147 (100%).

Example 46

N-[6-(2-Phenylchroman-6-yloxy)pyridin-3-yl]methanesulfonamide

Pyridine (77 µl) and methanesufonyl chloride (32 µl) were added into a cooled solution of 6-(2-phenylchroman-6-yloxy) pyridin-3-ylamine (121 mg) in dry THF (2 ml). After stirring resulting mixture at 0° C. for additional 2 hours 1 M hydrochloric acid was added. Solution was extracted with ethyl acetate. Combined organic layers were dried with $Na_2SO_4$ and evaporated. N-[6-(2-Phenylchroman-6-yloxy)pyridin-3-yl]methanesulfonamide was recrystallised from diethyl ether. $^1$H NMR (300 MHz, $d_6$-DMSO) δ: 9.64 (s, 1H), 7.99 (d, 1H, J 2.8 Hz), 7.67 (dd, 1H, J 2.8, 8.8 Hz), 7.47-7.31 (m, 5H), 6.97 (d, 1H, J 8.8 Hz), 6.89-6.82 (m, 3H), 5.12 (dd, 1H, J 2.2, 10.1 Hz), 3.0-2.9 (m, 1H), 2.98 (s, 3H), 2.77-2.69 (m, 1H), 2.20-2.13 (m, 1H), 2.04-1.96 (m, 1H).

Example 47

1-Methyl-3-[6-(2-phenylchroman-6-yloxy)pyridin-3-yl]thiourea

Solution of 6-(2-phenylchroman-6-yloxy)pyridin-3-ylamine (150 mg) and methyl isothiocyanate (94 µl) in ethanol was refluxed for 10 hours. After cooling solvents were evaporated. Crude product of 1-methyl-3-[6-(2-phenylchroman-6-yloxy)pyridin-3-yl]thiourea was purified by column chromatography (5% methanol in dichloromethane). $^1$H NMR (400 MHz, $d_6$-DMSO) δ: 9.45 (bs, 1H), 8.02 (d, 1H, J 2.7 Hz), 7.81 (dd, 1H, J 2.7, 8.8 Hz), 7.70 (bs, 1H), 7.47-7.38 (m, 4H), 7.36-7.32 (m, 1H), 6.94-6.86 (m, 4H), 5.12 (dd, 1H J 2.3, 10.1 Hz), 2.98-2.93 (m, 1H), 2.90 (d, 3H, J 4.3 Hz), 2.76-2.71 (m, 1H), 2.19-2.15 (m, 1H), 2.15-1.99 (m, 1H).

Example 48

3-[6-(5-Nitropyridin-2-yloxy)chroman-2-yl]phenol a) 6-Hydroxy-2-(3-hydroxyphenyl)chroman-4-one
6-Hydroxy-2-(3-hydroxyphenyl)chroman-4-one was prepared as described for 6-hydroxy-2-(3-fluorophenyl)chroman-4-one in Example 9(a). The product was recrystallised from ethanol. $^1$H NMR (400 MHz, $d_6$-DMSO) δ: 9.50 (bs, 1H), 9.41 (bs, 1H), 7.22-7.17 (m, 1H), 7.11 (d, 1H, J 3.0 Hz), 7.03 (dd, 1H J 3.0, 8.9 Hz), 6.64 (d, 1H, J 8.9 Hz), 6.92-6.90 (m, 2H), 6.76-6.73 (m, 1H), 5.46 (dd, 1H J 2.9, 12.7 Hz), 3.09 (dd, 1H, J 12.7, 16.9 Hz), 2.75 (dd, 1H, J 2.9, 16.9 Hz).

b) 2-(3-Hydroxyphenyl)chroman-4,6-diol 2-(3-Hydroxyphenyl)chroman-4,6-diol was prepared as described for 2-phenylchroman-4,6-diol in Example 8(a) starting from 6-hydroxy-2-(3-hydroxyphenyl)chroman-4-one. $^1$H NMR (400 MHz, $d_6$-DMSO) δ: 9.43 (bs, 1H), 8.88 (bs, 1H), 7.19-7.15 (m, 1H), 6.87 (d, 1H, J 2.7 Hz), 6.84-6.82 (m, 2H), 6.72-6.69 (m, 1H), 6.58 (d, 1H, J 8.7 Hz), 6.53 (dd, 1H, J 2.7, 8.7), 5.01 (d, 1H, J 11.3 Hz), 4.86 (dd, 1H, J 6.2, 10.8 Hz), 2.25-2.19 (m, 1H), 1.88-1.75 (m, 1H).

c) 2-(3-Hydroxyphenyl)chroman-6-ol 2-(3-Hydroxyphenyl)chroman-6-ol was prepared as described for 2-(3-fluorophenyl)chroman-6-ol in Example 9(c) starting from 2-(3-hydroxyphenyl)chroman-4,6-diol. $^1$H NMR (400 MHz, $d_6$-DMSO) δ: 9.38 (s, 1H), 8.77 (s, 1H), 7.17-7.13 (m, 1H), 6.82-6.79 (m, 2H), 6.70-6.67 (m, 1H), 6.62 (d, 1H, J 8.6 Hz), 6.52-6.47 (m, 2H), 4.89 (dd, 1H, J 2.1, 9.9Hz), 2.86-2.82 (m, 1H), 2.65-2.59 (m, 1H), 2.09-2.04 (m, 1H), 1.91-1.85 (m, 1H).

d)
3-[6-(5-Nitropyridin-2-yloxy)chroman-2-yl]phenol

3-[6-(5-Nitropyridin-2-yloxy)chroman-2-yl]phenol was prepared as described for 5-nitro-2-(2-phenylchroman-6-yloxy)pyridine in Example 1 (b) starting from 2-(3-hydroxyphenyl)chroman-6-ol. $^1$H NMR (400 MHz, d$_6$-DMSO) δ: 9.44 (s, 1H), 9.04 (d, 1H, J 2.8 Hz), 8.60 (dd, 1H, J 2.8, 9.1 Hz), 7.21-7.16 (m, 2H), 7.00-6.94 (m, 2H), 6.91-6.84 (m, 3H), 6.73-6.70 (m, 1H), 5.06 (dd, 1H, J 2.1, 9.9 Hz), 2.99-2.92 (m, 1H), 2.75-2.69 (m, 1H), 2.17-2.01 (m, 1H), 2.00-1.93 (m, 1H).

Example 49

6-[2-(2,5-Difluorophenyl)chroman-6-yloxy]-pyridin-3-ylamine

6-[2-(2,5-Difluorophenyl)chroman-6-yloxy]-pyridin-3-ylamine was prepared as described for 5-amino-2-(2-phenylchroman-6-yloxy)pyridine in Example 26 starting from 830 mg of 2-[2-(2,5-Difluorophenyl)chroman-6-yloxy]-5-nitropyridine (Example 14(d)). $^1$H NMR (300 MHz, d$_6$-DMSO) δ: 7.51 (d, 1H, J 2.9 Hz), 7.36-7.25 (m, 3H), 7.05 (dd, 1H, J 8.6, 2.9 Hz), 6.84-6.68 (m, 4H), 5.29 (d, 1H, J 8.6), 4.99 (s, 2H), 2.96 (m, 1H), 2.72 (m, 1H), 2.14 (m, 1H), 2.01 (m, 1H).

Example 50

N-{6-[2-(2,5-Difluorophenyl)chroman-6-yloxy]pyridin-3-yl}acetamide

N-{6-[2-(2,5-Difluorophenyl)chroman-6-yloxy]pyridin-3-yl}acetamide was prepared as described for 5-N'-acetylamino-2-(2-phenylchroman-6-yloxy)pyridine in Example 27 starting from 370 mg of 6-[2-(2,5-difluorophenyl)chroman-6-yloxy]-pyridin-3-ylamine (Example 49). The product was purified on preparative TLC-plate covered with silica gel using ethyl acetate-heptane (4:1) as an eluant. $^1$H NMR (400 MHz, CD$_3$OD) δ: 8.27 (d, 1H, J 2.7 Hz), 8.01 (dd, 1H, J 8.9, 2.7 Hz), 7.26 (m, 1H), 7.13 (m, 1H), 7.08 (m, 1H), 6.92-6.84 (m, 4H), 5.32 (dd, 1H, J 10.1, 1.6 Hz), 2.99 (ddd, 1H, J −16.9, 11.4, 5.9 Hz), 2.78 (ddd, 1H, J −16.9, 8.4, 5.1 Hz), 2.26 (m, 1H), 2.13 (s, 3H), 1.97 (m, 1H).

Example 51

6-[2-(2-Fluorophenyl)chroman-6-yloxy]-pyridin-3-ylamine

6-[2-(2-Fluorophenyl)chroman-6-yloxy]-pyridin-3-ylamine was prepared as described for 5-amino-2-(2-phenylchroman-6-yloxy)pyridine in Example 26 starting from 240 mg of 2-[2-(2-fluorophenyl)chroman-6-yloxy]-5-nitropyridine (Example 19(d)). $^1$H NMR (400 MHz, d$_6$-DMSO) δ: 7.52 (m, 1H), 7.51 (d, 1H, J 3.0 Hz), 7.41 (m, 1H), 7.28-7.24 (m, 2H), 7.05 (dd, 1H, J 8.6, 3.0 Hz), 6.81-6.73 (m, 3H), 6.70 (d, 1H, J 8.6 Hz), 5.31 (dd, 1H, J 10.3, 2.2 Hz), 5.00 (s, 2H), 2.98 (m, 1H), 2.72 (m, 1H), 2.15 (m, 1H), 2.06 (m, 1H).

Example 52

N-{6-[2-(2-Fluorophenyl)chroman-6-yloxy]pyridin-3-yl}acetamide

N-{6-[2-(2-Fluorophenyl)chroman-6-yloxy]pyridin-3-yl}acetamide was prepared as described for 5-N'-acetylamino-2-(2-phenylchroman-6-yloxy)pyridine in Example 27 starting from 220 mg of 6-[2-(2-fluorophenyl)chroman-6-yloxy]-pyridin-3-ylamine (Example 51). The product was recrystallised from a mixture of methanol and diethyl ether. $^1$H NMR (400 MHz, d$_6$-DMSO) δ: 10.06 (s, 1H), 8.27 (d, 1H, J 2.7 Hz), 8.01 (dd, 1H, J 8.8, 2.7 Hz), 7.55 (m, 1H), 7.42 (m, 1H), 7.29-7.23 (m, 2H), 6.93 (d, 1H, J 8.8 Hz), 6.89-6.85 (m, 3H), 5.34 (dd, 1H, J 10.2, 2.2 Hz), 3.01 (m, 1H), 2.75 (m, 1H), 2.17 (m, 1H), 2.05 (m, 1H), 2.04 (s, 3H).

Example 53

N-{6-[2-(2-Fluorophenyl)chroman-6-yloxy]pyridin-3-yl}methanesulfonamide

N-{6-[2-(2-Fluorophenyl)chroman-6-yloxy]pyridin-3-yl}methanesulfonamide was prepared as described for N-[6-(2-phenylchroman-6-yloxy)pyridin-3-yl]methane sulfonamide in Example 46 starting from 400 mg of 6-[2-(2-fluorophenyl)chroman-6-yloxy]-pyridin-3-ylamine (Example 51). The product was crystallised from a mixture of methanol and diethyl ether. $^1$H NMR (400 MHz, d$_6$-DMSO) δ: 9.67 (s, 1H), 7.99 (d, 1H, J 2.8 Hz), 7.67 (dd, 1H, J 8.8, 2.8 Hz), 7.55 (m, 1H), 7.42 (m, 1H), 7.29-7.23 (m, 2H), 6.98 (dd, 1H, J 8.8 Hz), 6.92-6.84 (m, 3H), 5.35 (dd, 1H, J 10.4, 2.3 Hz), 3.01 (m, 1H), 2.99 (s, 3H), 2.76 (m, 1H), 2.16 (m, 1H), 2.04 (m, 1H).

Example 54

6-[2-(3-fluorophenyl)chroman-6-yloxy]-pyridin-3-ylamine

6-[2-(3-fluorophenyl)chroman-6-yloxy]-pyridin-3-ylamine was prepared as described for 5-amino-2-(2-phenylchroman-6-yloxy)pyridine in Example 26 starting from 2.34 g of 2-[2-(3-fluorophenyl)chroman-6-yloxy]-5-nitropyridine (Example 9(d)). $^1$H NMR (400 MHz, d$_6$-DMSO) δ: 7.51 (d, 1H, J 3.0 Hz), 7.44 (m, 1H), 7.30-7.25 (m, 2H), 7.16 (m, 1H), 7.05 (dd, 1H, J 8.6, 3.0 Hz), 6.83-6.73 (m, 3H), 6.69 (d, 1H, J 8.6 Hz), 5.13 (dd, 1H, J 10.0, 3.0 Hz), 5.00 (s, 2H), 2.93 (ddd, 1H, −16.8, 10.5, 5.3 Hz), 2.68 (ddd, 1H, J −16.8, 8.0, 4.4 Hz), 2.18 (m, 1H), 1.96 (m, 1H).

Example 55

N-{6-[2-(3-fluorophenyl)chroman-6-yloxy]pyridin-3-yl}acetamide

N-{6-[2-(3-fluorophenyl)chroman-6-yloxy]pyridin-3-yl}acetamide was prepared as described for 5-N'-acetylamino-2-(2-phenylchroman-6-yloxy)pyridine in Example 27 starting from 300 mg of 6-[2-(3-fluorophenyl)chroman-6-yloxy]pyridin-3-ylamine (Example 54). The product was recrystallised from a mixture of methanol and diethyl ether. $^1$H NMR (400 MHz, d$_6$-DMSO) δ: 10.09 (s, 1H), 8.28 (d, 1H, J 2.7 Hz), 8.02 (dd, 1H, J 8.8, 2.7 Hz), 7.46 (m, 1H), 7.31-7.27 (m, 2H), 7.17 (m, 1H), 6.93 (d, 1H, J 8.8 Hz), 6.89-6.83 (m, 3H), 5.16 (dd, 1H, J 10.1, 2.1 Hz), 2.95 (ddd, 1H, J −16.5, 11.0, 6.5 Hz), 2.71 (ddd, 1H, J −16.5, 8.7, 4.4 Hz), 2.19 (m, 1H), 2.04 (s, 3H), 1.96 (m, 1H).

Example 56

6-(5-Aminopyridin-2-yloxy)-2-phenylchroman-4-one 6-(5-Aminopyridin-2-yloxy)-2-phenylchroman-4-one was prepared as described for 5-amino-2-(2-phenylchroman-6-yloxy)pyridine in Example 26 starting from 100 mg of 6-(5-nitropyridin-2-yloxy)-2-phenylchroman-4-one (Example 6). $^1$H NMR (400 MHz, CD$_3$OD) δ: 7.62 (d, 1H, J 3.0 Hz), 7.51-7.49 (m, 2H), 7.42-7.33 (m, 3H), 7.25-7.18 (m, 3H), 7.06 (d, 1H, J 8.8 Hz), 6.76 (d, 1H, J 8.6Hz), 5.50 (dd, 1H, J 13.0, 2.9 Hz), 3.08 (dd, 1H, −17.0, 13.0 Hz), 2.82 (dd, 1H, J −17.0, 2.9 Hz).

Example 57

Acetic Acid 6-(5-nitropyridin-2-yloxy)-2-phenylchroman-4-yl Ester

Acetanhydride (0.26 ml) was added dropwise into a solution of 100 mg of 6-(5-nitropyridin-2-yloxy)-2-phenylchroman-4-ol (Example 8(b)) in dry pyridine. The reaction mixture was refluxed for 1½ hours. It was then poured in ice-water and extracted with ethyl acetate. The organic phase was washed with 1 M HCl-solution, water and saturated NaCl-solution. It was then dried with MgSO$_4$ and evaporated to dryness. $^1$H NMR (400 MHz, d$_6$-DMSO) δ: 9.05 (d, 1H, J 2.8 Hz), 8.61 (dd, 1H, J 9.1, 2.8 Hz), 7.52-7.35 (m, 5H), 7.23 (d, 1H, J 9.1 Hz), 7.14-7.10 (m, 2H), 6.98 (d, 1H, J 8.5 Hz), 6.18 (dd, 1H, J 10.1, 6.4 Hz), 5.44(dd, 1H, J 11.4, 1.4Hz), 2.51 (m, 1H), 2.15 (m, 1H), 2.05 (s, 3H).

Example 58

6-(2-Aminoethoxy)-2-phenylchroman-4-one Methane Sulfonate a) 6-(2-Azidoethoxy)-2-phenylchroman-4-one 6-(2-Azidoethoxy)-2-phenylchroman-4-one was prepared as described for 6-(2-azidoethoxy)-2-phenylchroman in example 4(a) starting from 1.0 g of 6-hydroxy-flavanone. $^1$H NMR (400 MHz, CD$_3$OD) δ: 7.53-7.51 (m, 2H), 7.44-7.35 (m, 4H), 7.22 (dd, 1H, J 9.0, 3.1 Hz), 7.04 (d, 1H, J 9.0 Hz), 5.51 (dd, 1H, J 13.1, 3.0 Hz), 4.17 (t, 2H, J 4.9 Hz), 3.60 (t, 2H, J 4.9 Hz), 3.11 (dd, 1H, J −16.9, 13.1 Hz), 2.85 (dd, 1H, J −16.9, 3.0 Hz).

b) 6-(2-Aminoethoxy)-2-phenylchroman-4-one Methane Sulfonate 6-(2-Aminoethoxy)-2-phenylchroman-4-one methane sulfonate was prepared as described for 2-(2-phenylchroman-6-yloxy)ethylamine methane sulfonate in Example 4 (b) starting from 6-(2-azidoethoxy)-2-phenylchroman-4-one. $^1$H NMR (400 MHz, d$_6$-DMSO) δ: 7.91 (bs, 3H), 7.55-7.54 (m, 2H), 7.46-7.37 (m, 3H), 7.31 (d, 1H, J 3.1 Hz), 7.28 (dd, 1H, 8.8, 3.1 Hz), 7.12 (d, 1H, 8.8 Hz), 5.63 (dd, 1H, 13.0, 3.0 Hz), 4.17 (t, 2H, J 5.1 Hz), 3.25 (dd, 1H, J −16.9, 13.0 Hz), 3.23 (m, 2H), 2.86 (dd, 1H, J −16.9, 3.0 Hz), 2.29 (s, 3H).

Example 59

2-(3-Bromophenyl)-6-(5-nitropyridin-2-yloxy)chroman-4-ol 2-(3-Bromophenyl)-6-(5-nitropyridin-2-yloxy)chroman-4ol was prepared as described for 5-nitro-2-(2-phenylchroman-6-yloxy)pyridine in Example 1(b) starting from 215 mg of 2-(3-bromophenyl)chroman-4,6-diol (Example 15(b)). The product was recrystallised from a mixture of 2-propanol and acetone. $^1$H NMR (300 MHz, d$_6$-DMSO) δ: 9.04 (d, 1H, J 2.8 Hz), 8.61 (dd, 1H, J 9.1, 2.8 Hz), 7.69 (m, 1H), 7.58-7.50 (m, 2H), 7.40 (m, 1H), 7.25 (d, 1H, J 2.7 Hz), 7.22 (d, 1H, 9.1 Hz), 7.02 (dd, 1H, J 8.8, 2.7 Hz), 6.91 (d, 1H, J 8.8 Hz), 5.65 (d, 1H, J 6.4 Hz), 5.33 (d, 1H, J 10.8 Hz), 4.97 (m, 1H), 2.36 (m, 1H), 1.94 (m, 1H).

Example 60

2-(2-Fluorophenyl)-6-(5-nitropyridin-2-yloxy)chroman-4-ol 2-(2-Fluorophenyl)-6-(5-nitropyridin-2-yloxy)chroman-4-ol was prepared as described for 5-nitro-2-(2-phenylchroman-6-yloxy)pyridine in Example 1(b) starting from 315 mg of 2-(2-fluorophenyl)chroman-4,6-diol (Example 19(b)). The product was recrystallised from a mixture of 2-propanol and acetone. $^1$H NMR (400 MHz, d$_6$-DMSO) δ: 9.04 (d, 1H, J 2.9 Hz), 8.61 (dd, 1H, J 9.1, 2.9 Hz), 7.61 (m, 1H), 7.43 (m, 1H), 7.31-7.24 (m, 3H), 7.23 (d, 1H, J 9.1 Hz), 7.02 (dd, 1H, J 8.7, 3.1 Hz), 6.89 (d, 1H, J 8.7 Hz), 5.69 (d, 1H, J 6.3 Hz), 5.55 (d, 1H, J 11.9 Hz), 5.00 (m, 1H), 2.33 (m, 1H), 2.07 (m, 1H).

Example 61

2-(2,5-Difluorophenyl)-6-(5-nitropyridin-2-yloxy)chroman-4-ol 2-(2,5-Difluorophenyl)-6-(5-nitropyridin-2-yloxy)chroman-4-ol was prepared as described for 5-nitro-2-(2-phenylchroman-6-yloxy)pyridine in Example 1(b) starting from 200 mg of 2-(2,5-difluorophenyl)chroman-4,6-diol (Example 14(b)). The product was purified on preparative TLC-plate covered with silica gel using toluene-ethyl acetate (4:1) as an eluant. $^1$H NMR (400 MHz, CDCl$_3$) δ: 9.03 (d, 1H, J 2.8 Hz), 8.50 (dd, 1H, J 9.1, 2.8 Hz), 7-36-7.33 (m, 2H), 7.08-6.95 (m, 5H), 5.50 (d, 1H, J 11.1 Hz), 5.09 (m, 1H), 2.53 (m, 1H), 2.05 (m, 1H).

Example 62

2-(3-Fluorophenyl)-6-(5-nitropyridin-2-yloxy)chroman-4-ol 2-(3-Fluorophenyl)-6-(5-nitropyridin-2-yloxy)chroman-4-ol was prepared as described for 5-nitro-2-(2-phenylchroman-6-yloxy)pyridine in Example 1(b) starting from 890 mg of 2-(3-fluorophenyl)chroman-4,6-diol (Example 9(b)). The product was purified by column chromatography using gradient elution with ethyl acetate-heptane (20%→33%) and then crystallised from a mixture of 2-propanol and acetone. $^1$H NMR (400 MHz, d$_6$-DMSO) δ: 9.04 (d, 1H, J 2.9 Hz), 8.61 (dd, 1H, J 9.1, 2.9 Hz), 7.48 (m, 1H), 7.35-7.31 (m, 2H), 7.26-7.19 (m, 3H), 7.02 (dd, 1H, J 8.8, 2.9 Hz), 6.91 (d, 1H, J 8.8 Hz), 5.67 (d, 1H, J 6.4 Hz), 5.34 (d, 1H, J 10.4 Hz), 4.98 (m, 1H), 2.36 (m, 1H), 1.99 (m, 1H).

Example 63

2-[2-(2,5-Difluorophenyl)chroman-6-yloxy]-5-ethoxyphenylamine Hydrochloride a) 1-Chloro-4-ethoxy-2-nitrobenzene

4-Chloro-3-nitrobenzene (5.0 g) was dissolved in acetone and ethyl iodide (2.5 ml) and potassium carbonate (4.4 g) were added. The reaction mixture was stirred at 40° C. for 4½ hours. After cooling to room temperature the mixture was filtered and the filtrate was evaporated to dryness. $^1$H NMR (400 MHz, $d_6$-DMSO) δ: 7.64 (m, 2H), 7.27 (dd, 1H, J 9.0, 3.1 Hz), 4.12 (q, 2H, J 7.0 Hz), 1.34 (t, 3H, 7.0 Hz).

b) 2-(2,5-Difluorophenyl)-6-(4-ethoxy-2-nitrophenoxy)chroman 320 mg of 2-(2,5-Difluorophenyl)chroman-6-ol (Example 14(c)) was dissolved in dry DMF and potassium tert-butoxide (150 mg) was added. The resulting mixture was stirred for 30 minutes and 1-chloro-4-ethoxy-2-nitrobenzene (250 mg) was added. The reaction mixture was refluxed for 8 hours. After cooling to room temperature 1 M HCl-solution was added into the reaction mixture and it was extracted with ethyl acetate. The combined organic extracts were washed with water and saturated NaCl-solution. The product was purified by column chromatography using heptane-ethyl acetate (3:1) as an eluant. $^1$H NMR (300 MHz, $CDCl_3$) δ: 7.43 (d, 1H, J 2.9Hz), 7.25 (m, 1H), 7.08-6.97 (m, 4H), 6.89-6.75 (m, 3H), 5.31 (d, 1H, J 9.1 Hz), 4.06 (q, 2H, J 7.0 Hz), 2.97 (m, 1H), 2.74 (m, 1H), 2.26 (m, 1H), 1.98 (m, 1H), 1.44 (t, 3H, 7.0 Hz).

c) 2-[2-(2,5-Difluorophenyl)chroman-6-yloxy]-5-ethoxyphenylamine Hydrochloride 2-[2-(2,5-Difluorophenyl)chroman-6-yloxy]-5-ethoxyphenylamine hydrochloride was prepared as described for 5-methoxy-2-(2-phenylchroman-6-yloxy)phenylamine hydrochloride in example 3(b) starting from 120 mg of 2-(2,5-difluorophenyl)-6-(4-ethoxy-2-nitrophenoxy)chroman. $^1$H NMR (400 MHz, $CDCl_3$) δ: 7.26-7.22 (m, 2H), 7.01-6.74 (m, 7H), 5.22 (d, 1H, J 9.1 Hz), 3.90 (q, 2H, J 6.9 Hz), 2.90 (m, 1H), 2.68 (m, 1H), 2.19 (m, 1H), 1.90 (m, 1H), 1.34 (t, 3H, 6.9 Hz).

Example 64

5-Nitro-2-[2-(4-trifluoromethylphenyl)chroman-6-yloxy]pyridine a) 6-Hydroxy-2-(4-trifluoromethylphenyl)chroman-4-one

6-Hydroxy-2-(4-trifluoromethylphenyl)chroman-4-one was prepared as described for 2-(3-fluorophenyl)-6-hydroxychroman-4-one in Example 9(a) starting from 2.0 g of 2',5'-dihydroxyacetophenone and 2.1 ml of 4-trifluoromethylbenzaldehyde. The product was purified by column chromatography using heptane-ethyl acetate (2:1) as an eluant. Further purification was carried out by column chromatography using toluene-ethyl acetate (4:1) as an eluant. Finally the product was crystallised from ethanol. $^1$H NMR (400 MHz, $d_6$-DMSO) δ: 9.47 (s, 1H), 7.82-7.76 (m, 4H), 7.13 (d, 1H, J 3.0 Hz), 7.06 (dd, 1H, J 8.8, 3.0 Hz), 6.99 (d, 1H, J 8.8 Hz), 5.70 (dd, 1H, J 12.9, 2.9 Hz), 3.16 (dd, 1H, J −16.9, 12.9 Hz), 2.86 (dd, 1H, J −16.9, 2.9 Hz).

b) 2-(4-Trifluoromethylphenyl)chroman-4,6-diol 2-(4-Trifluoromethylphenyl)chroman-4,6-diol was prepared as described for 2-phenylchroman-4,6-diol in Example 8(a) starting from 860 mg of 2-(4-trifluoromethylphenyl)-6-hydroxychroman-4-one. $^1$H NMR (400 MHz, $d_6$-DMSO) δ: 8.86 (s, 1H), 7.77 (d, 2H, J 8.3 Hz), 7.68 (d, 2H, J 8.3 Hz), 6.89 (d, 1H, J 2.9 Hz), 6.63 (d, 1H, J 8.7 Hz), 6.56 (dd, 1H, J 8.7, 2.9 Hz), 5.45 (d, 1H, J 7.0 Hz), 5.26 (d, 1H, J 11.2 Hz), 4.90 (m, 1H), 2.32 (m, 1H), 1.85 (m, 1H).

c) 2-(4-Trifluoromethylphenyl)chroman-6-ol 2-(4-Trifluoromethyl phenyl)chroman-6-ol was prepared as described for 2-(3-fluorophenyl)chroman-6-ol in Example 9(c) starting from 730 mg of 2-(4-trifluoromethylphenyl)chroman-4,6-diol. $^1$H NMR (400 MHz, $d_6$-DMSO) δ: 8.82 (s, 1H), 7.75 (d, 2H, J 8.3 Hz), 7.65 (d, 2H, J 8.3 Hz), 6.67 (d, 1H, J 8.6 Hz), 6.53 (d, 1H, J 2.9 Hz), 6.51 (dd, 1H, 8.6, 2.9 Hz), 5.12 (d, 1H, J 8.3 Hz), 2.90 (m, 1H), 2.63 (m, 1H), 2.16 (m, 1H), 1.92 (m, 1H).

d) 2-[2-(4-Trifluoromethylphenyl)chroman-6-yloxy]-5-nitropyridine

2-[2-(4-Trifluoromethylphenyl)chroman-6-yloxy]-5-nitropyridine was prepared as described for 5-nitro-2-(2-phenylchroman-6-yloxy)pyridine in Example 1(b) starting from 605 mg of 2-(4-trifluoromethylphenyl)chroman-6-ol. The product was purified column chromatography using 1.5% ethyl acetate in toluene as an eluant and then crystallised from a mixture of 2-propanol and acetone. $^1$H NMR (400 MHz, $d_6$-DMSO) δ: 9.04 (d, 1H, J 2.9 Hz), 8.60 (dd, 1H, J 9.1, 2.9 Hz), 7.79 (d, 2H, J 8.2 Hz), 7.70 (d, 1H, J 8.2 Hz), 7.21 (d, 1H, J 9.1 Hz), 7.01 (dd, 1H, J 8.7, 2.7 Hz), 6.98 (d, 1H, J 2.7 Hz), 6.95 (d, 1H, 8.7 Hz), 5.29 (dd, 1H, J 10.1, 2.0 Hz), 3.00 (ddd, 1H, J −16.9, 10.1, 5.8 Hz), 2.4 (ddd, 1H, J −16.9, 8.4, 4.5 Hz), 2.24 (m, 1H), 1.99 (m, 1H).

Example 65

6-[2-(4-Trifluoromethylphenyl)chroman-6-yloxy]pyridin-3-ylamine

6-[2-(4-Trifluoromethylphenyl)chroman-6-yloxy]pyridin-3-ylamine was prepared as described for 5-amino-2-(2-phenylchroman-6-yloxy)pyridine in Example 26 starting from 275 mg of 2-[2-(4-trifluoromethylphenyl)chroman-6-yloxy]-5-nitropyridine (Example 64(d)). $^1$H NMR (400 MHz, $d_6$-DMSO) δ: 7.78 (d, 2H, J 8.4 Hz), 7.68 (d, 2H, J 8.4 Hz), 7.52 (dd, 1H, J 2.9, 0.5 Hz), 7.06 (dd, 1H, 8.6, 2.9 Hz) 6.84 (m, 1H), 6.77-6.75 (m, 2H), 6.70 (dd, 1H, J 8.6, 0.5 Hz), 5.23 (dd, 1H, J 10.0, 2.0 Hz), 5.01 (s, 2H), 2.95 (ddd, 1H, −16.8, 11.1, 5.9 Hz), 2.69 (ddd, 1H, J −16.8, 8.5, 4.8 Hz), 2.21 (m, 1H), 1.97 (m, 1H).

Example 66

N-{6-[2-(4-Trifluoromethylphenyl)chroman-6-yloxy]pyridin-3-yl}acetamide

N-{6-[2-(4-Trifluoromethylphenyl)chroman-6-yloxy]pyridin-3-yl}acetamide was prepared as described for 5-N'-acetylamino-2-(2-phenylchroman-6-yloxy)pyridine in Example 27 starting from 140 mg of 6-[2-(4-trifluoromethylphenyl)chroman-6-yloxy]-pyridin-3-ylamine (Example 65). $^1$H NMR (400 MHz, $d_6$-DMSO) δ: 10.11 (s, 1H), 8.29 (d, 1H, J 2.7 Hz), 8.02(dd, 1H, J 8.9, 2.7 Hz), 7.78 (d, 2H, J 8.3 Hz), 7.69 (d, 2H, J 8.3 Hz), 7.17 (m, 1H), 6.94-6.86 (m, 3H), 5.66 (d, 1H, J 8.2 Hz), 2.98 (m, 1H), 2.72 (m, 1H), 2.23 (m, 1H), 2.04 (s, 3H), 1.97 (m, 1H).

Example 67

N-{6-[2-(3-Fluorophenyl)chroman-6-yloxy]pyridin-3-yl}methane Sulfonamide

N-{6-[2-(3-Fluorophenyl)chroman-6-yloxy]pyridin-3-yl}methane sulfonamide was prepared as described for N-[6-(2-phenylchroman-6-yloxy)pyridin-3-yl]methanesulfonamide in Example 46 starting from 300 mg of 6-[2-(3-fluorophenyl)chroman-6-yloxy]-pyridin-3-ylamine (Example 54). The product was purified by passing through silica gel using ethyl acetate-heptane (5:1) as an eluant. $^1$H NMR (400 MHz, $d_6$-DMSO) δ: 9.67 (s, 1H), 7.99 (dd, 1H, J 2.8, 0.6 Hz), 7.67 (dd, 1H, J 8.8, 2.8 Hz), 7.46 (m, 1H), 7.31-7.27 (m, 2H), 7.17 (m, 1H), 6.98 (dd, 1H, J 8.8, 0.6 Hz), 6.90-6.88 (m, 3H), 5.16 (dd, 1H, J 10.0, 2.2 Hz), 2.99 (s, 3H), 2.96 (m, 1H), 2.72 (m, 1H), 2.20 (m, 1H), 1.99 (m, 1H).

Example 68

2-(4-Chlorophenyl)-6-(5-nitropyridin-2-yloxy)chroman-4-ol a) 6-Hydroxy-2-(4-chlorophenyl)chroman-4-one

6-Hydroxy-2-(4-chlorophenyl)chroman-4-one was prepared as described for 2-(3-fluorophenyl)-6-hydroxychroman-4-one in Example 9(a) starting from 3.0 g of 2',5'-dihydroxyacetophenone and 2.8 g of 4-chlorobenzaldehyde. The product was triturated from ethanol. $^1$H NMR (400 MHz, $d_6$-DMSO) δ: 9.46 (s, 1H), 7.56 (d, 2H, J 8.5 Hz), 7.45 (d, 2H, J 8.5 Hz), 7.11 (d, 1H, J 2.8 Hz), 7.04 (dd, 1H, J 8.9, 2.8 Hz), 6.96 (d, 1H, J 8.9 Hz), 5.58 (dd, 1H, J 13.1, 2.9 Hz), 3.15 (dd, 1H, J −16.8, 13.1 Hz), 2.79 (dd, 1H, J −16.8, 2.9 Hz).

b) 2-(4-Chlorophenyl)chroman-4,6-diol 2-(4-Chlorophenyl)chroman-4,6-diol was prepared as described for 2-phenylchroman-4,6-diol in Example 8(a) starting from 375 mg of 2-(4-chlorophenyl)-6-hydroxychroman-4-one. $^1$H NMR (400 MHz, $d_6$-DMSO) δ: 8.84 (s, 1H), 7.49-7.44 (m, 4H), 6.88 (d, 1H, J 2.8 Hz), 6.60 (d, 1H, J 8.6 Hz), 6.55 (dd, 1H, J 8.6, 2.8 Hz), 5.43 (bs, 1H), 5.14 (dd, 1H, J 11.9, 1.6 Hz), 4.87 (m, 1H), 2.26 (m, 1H), 1.85 (m, 1H).

c) 2-(4-Chlorophenyl)-6-(S-nitropyridin-2-yloxy)chroman-4ol 2-(4-Chlorophenyl)-6-(5-nitropyridin-2-yloxy)chroman-4-ol was prepared as described for 5-nitro-2-(2-phenylchroman-6-yloxy)pyridine in Example 1(b) starting from 330 mg of 2-(4-chlorophenyl)chroman-4,6-diol. The product was purified by column chromatography using heptane-ethyl acetate (2:1) as an eluant. $^1$H NMR (300 MHz, $d_6$-DMSO) δ: 9.04 (d, 1H, J 2.9 Hz), 8.61 (dd, 1H, J 9.1, 2.9 Hz), 7.54-7.47 (m, 4H), 7.25 (d, 1H, J 2.8 Hz), 7.22 (d, 1H, J 9.1 Hz), 7.02 (dd, 1H, J 8.8, 2.8 Hz), 6.89 (d, 1H, J 8.8 Hz), 5.65 (d, 1H, J 6.4 Hz), 5.33 (d, 1H, J 10.6 Hz), 4.98 (m, 1H), 2.34 (m, 1H), 1.94 (m, 1H).

Example 69

2-[2-(2.4-Difluorophenyl)chroman-6-yloxy]-5-nitropyridine a) 2-(2,4-Difluorophenyl)-6-hydroxychroman-4-one 2-(2,4-Difluorophenyl)-6-hydroxychroman-4-one was prepared as described for 2-(3-fluorophenyl)6-hydroxychroman-4-one in Example 9(a) starting from 3.0 g of 2',5'-dihydroxyacetophenone and 1,6 ml of 2,4-difluorobenzaldehyde. $^1$H NMR (400 MHz, $d_6$-DMSO) δ: 9.46 (s, 1H), 7.73 (m, 1H), 7.34 (m, 1H), 7.19 (m, 1H), 7.13 (d, 1H, J 2.9 Hz), 7.04 (dd, 1H, J 8.8, 2.9 Hz), 6.95 (d, 1H, J 8.8 Hz), 5.74 (dd, 1H, J 13.5, 2.8 Hz), 3.28 (dd, 1H, J −16.9, 13.5 Hz), 2.74 (dd, 1H, J −16.9, 2.8 Hz).

b) 2-(2,4-Difluorophenyl)chroman-4,6-diol 2-(2,4-Difluorophenyl)chroman-4,6-diol was prepared as described for 2-phenylchroman-4,6-diol in Example 8(a) starting from 1,47 g of 2-(2,4-difluorophenyl)-6-hydroxychroman-4-one. $^1$H NMR (400 MHz, $d_6$-DMSO) δ: 8.86 (s, 1H), 7.61 (m, 1H), 7.28 (m, 1H), 7.14 (m, 1H), 6.88 (d, 1H, J 2.7 Hz), 6.59 (d, 1H, J 8.9 Hz), 6.54 (dd, 1H, J 8.9, 2.7 Hz), 5.46 (s, 1H), 5.32 (dd, 1H, J 11.9, 1.4 Hz), 4.88 (m, 1H), 2.24 (m, 1H), 1.99 (m, 1H).

c) 2-(2,4-Difluorophenyl)chroman-6-ol 2-(2,4-Difluorophenyl)chroman-6-ol was prepared as described for 2-(3-fluorophenyl)chroman-6-ol in Example 9(c) starting from 800 mg of 2-(2,4-difluorophenyl)chroman-4,6-diol. $^1$H NMR (400 MHz, $d_6$-DMSO) δ: 8.83 (s, 1H), 7.56 (m, 1H), 7.28 (m, 1H), 7.13 (m, 1H), 6.63 (m, 1H), 6.53-6.50 (m, 2H), 5.17 (dd, 1H, J 10.3, 2.3 Hz), 2.92 (ddd, 1H, J −17.0, 11.5, 5.8 Hz), 2.66 (ddd, 1H, J −17.0, 5.0, 2.7 Hz), 2.09 (m, 1H), 1.98 (m, 1H).

d) 2-[2-(2,4-Difluorophenyl)chroman-6-yloxy]-5-nitropyridine

2-[2-(2,4-Difluorophenyl)chroman-6-yloxy]-5-nitropyridine was prepared as described for 5-nitro-2-(2-phenylchroman-6-yloxy)pyridine in Example 1(b) starting from 720 mg of 2-(2,4-difluorophenyl)chroman-6ol. $^1$H NMR (400 MHz, $d_6$-DMSO) δ: 9.04 (d, 1H, J 3.0 Hz), 8.60 (dd, 1H, J 9.0, 3.0 Hz), 7.61 (m, 1H), 7.31 (m, 1H), 7.21 (d, 1H, 9.0 Hz), 7.17 (m, 1H), 7.02 (d, 1H, J 2.9 Hz), 6.97 (dd, 1H, J 8.9, 2.9 Hz), 6.91 (d, 1H, 8.9 Hz), 5.34 (dd, 1H, J 9.9, 2.0 Hz), 3.03 (m, 1H), 2.78 (m, 1H), 2.17 (m, 1H), 2.07 (m, 1H).

Example 70

6-[2-(2,4-Difluorophenyl)chroman-6-yloxy]-pyridin-3-ylamine

6-[2-(2,4-Difluorophenyl)chroman-6-yloxy]-pyridin-3-ylamine was prepared as described for 5-amino-2-(2-phenylchroman-6-yloxy)pyridine in Example 26 starting from 845 mg of 2-[2-(2,4-difluorophenyl)chroman-6-yloxy]-5-nitropyridine (Example 69(d)). $^1$H NMR (400 MHz, $d_6$-DMSO) δ: 7.58 (m, 1H), 7.51 (d, 1H, J 3.3 Hz), 7.30 (m, 1H), 7.15 (m, 1H), 7.05 (dd, 1H, J 8.3, 3.3 Hz), 6.84-6.73 (m, 3H), 6.70 (d, 1H, J 8.3 Hz), 5.27 (dd, 1H, J 10.3, 2.3 Hz), 5.01 (s, 2H), 2.97 (m, 1H), 2.73 (m, 1H), 2.13 (m, 1H), 2.03 (m, 1H).

Example 71

N-{6-[2-(2,4-Difluorophenyl)chroman-6-yloxy]pyridin-3-yl}methane Sulfonamide

N-{6-[2-(2,4-difluorophenyl)chroman-6-yloxy]pyridin-3-yl}methane sulfonamide was prepared as described for N-[6-(2-phenylchroman-6-yloxy)pyridin-3-yl]methane sulfonamide in Example 46 starting from 100 mg of 6-[2-(2,4-difluorophenyl)chroman-6-yloxy]-pyridin-3-ylamine (Example 70). The product was crystallised from a mixture of methanol and diethyl ether. $^1$H NMR (400 MHz, d$_6$-DMSO) δ: 9.67 (s, 1H), 7.99 (d, 1H, J 2.8 Hz), 7.67 (dd, 1H, J 8.8, 2.8 Hz), 7.60 (m, 1H), 7.30 (m, 1H), 7.16 (m, 1H), 6.98 (d, 1H, J 8.8 Hz), 6.92-6.86 (m, 3H), 5.31 (dd, 1H, J 10.3, 2.3 Hz), 3.01 (m, 1H), 2.98 (s, 3H), 2.76 (m, 1H), 2.16 (m, 1H), 2.06 (m, 1H).

Example 72

2-(2,4-Difluorophenyl)-6-(5-nitropyridin-2-yloxy)chroman-4-ol 2-(2,4-Difluorophenyl)-6-(5-nitropyridin-2-yloxy)chroman-4-ol was prepared as described for 5-nitro-2-(2-phenylchroman-6-yloxy)pyridine in Example 1(b) starting from 520 mg of 2-(2,4-difluorophenyl)chroman-4,6-diol (Example 69(b)). The product was recrystallised from a mixture of 2-propanol and diethyl ether. 1H NMR (400 MHz, d$_6$-DMSO) δ: 9.04 (d, 1H, J 2.8 Hz), 8.61 (dd, 1H, J 9.1, 2.8 Hz), 7.66 (m, 1H), 7.32 (m, 1H), 7.26 (d, 1H, J 2.9 Hz), 7.23 (d, 1H, 9.1 Hz), 7.17 (m, 1H), 7.02 (dd, 1H, J 8.9, 2.9 Hz), 6.88 (d, 1H, J 8.9 Hz), 5.70 (bs, 1H), 5.52 (dd, 1H, J 11.9, 1.5 Hz), 5.00 (m, 1H), 2.31 (m, 1H), 2.09 (m, 1H).

Example 73

2-[2-(2-Chlorophenyl)chroman-6-yloxy]-5-nitropyridine a) 2-(2-Chlorophenyl)-6-hydroxychroman-4-one 2-(2-Chlorophenyl)-6-hydroxychroman-4-one was prepared as described for 2-(3-fluorophenyl)-6-hydroxychroman-4-one in Example 9(a) starting from 3.0 g of 2',5'-dihydroxyacetophenone and 2.8 g of 2-chlorobenzaldehyde. The product was passed though silica gel using heptane-ethyl acetate as an eluant and then triturated with ethanol. $^1$H NMR (400 MHz, d$_6$-DMSO) δ: 9.49 (s, 1H), 7.77 (dd, 1H, J 7.7, 2.0 Hz), 7.53 (dd, 1H, J 7.6, 1.8 Hz), 7.49-7.41 (m, 2H), 7.14 (d, 1H, J 2.9 Hz), 7.06 (dd, 1H, J 8.8, 2.9 Hz), 6.93 (d, 1H, J 8.8 Hz), 5.78 (dd, 1H, J 13.6, 2.6 Hz), 3.19 (dd, 1H, J –16.9, 13.6 Hz), 2.78 (dd, 1H, J –16.9, 2.6 Hz).

b) 2-(2-Chlorophenyl)chroman-4,6-diol 2-(2-Chlorophenyl)chroman-4,6-diol was prepared as described for 2-phenylchroman-4,6-diol in Example 8(a) starting from 1.12 g of 2(2-chlorophenyl)-6-hydroxychroman-4-one. $^1$H NMR (400 MHz, d$_6$-DMSO) δ: 7.63 (dd, 1H, J 7.7, 1.8 Hz), 7.49 (dd, 1H, J 7.8, 1.4 Hz), 7.45-7.36 (m, 2H), 6.89 (d, 1H, J 2.9 Hz), 6.63 (d, 1H, J 8.8 Hz), 6.56 (dd, 1H, J 8.9, 2.9 Hz), 5.39 (dd, 1H, J 11.7, 1.5 Hz), 4.90 (m, 1H), 2.33 (m, 1H), 1.82 (m, 1H).

c) 2-(2-Chlorophenyl)chroman-6-ol 2-(2-Chlorophenyl)chroman-6-ol was prepared as described for 2-(3-fluorophenyl)chroman-6-ol in Example 9(c) starting from 500 mg of 2-(2-chlorophenyl)-chroman-4,6-diol. $^1$H NMR (300 MHz, d$_6$-DMSO) δ: 7.58-7.36 (m, 4H), 6.66 (m, 1H), 6.55-6.51 (m, 2H), 5.23 (dd, 1H, J 10.1, 2.1 Hz), 2.92 (m, 1H), 2.68 (m, 1H), 2.17 (m, 1H), 1.87 (m, 1H).

d) 2-[2-(2-Chlorophenyl)chroman-6-yloxy]-5-nitropyridine

2-[2-(2-Chlorophenyl)chroman-6-yloxy]-5-nitropyridine was prepared as described for 5-nitro-2-(2-phenylchroman-6-yloxy)pyridine in Example 1(b) starting from 485 mg of 2-(2-chlorophenyl)chroman-6-ol. $^1$H NMR (400 MHz, d$_6$-DMSO) δ: 9.04 (d, 1H, J 2.9, 0.5 Hz), 8.60 (dd, 1H, J 9.1, 2.9 Hz), 7.62 (dd, 1H, J 7.5, 1.8 Hz), 7.51 (dd, 1H, J 7.6, 1.7 Hz), 7.45-7.40 (m, 2H), 7.21 (dd, 1H, J 9.1, 0.5 Hz), 7.04 (d, 1H, J 2.7 Hz), 6.99 (dd, 1H, J 8.8, 2.7 Hz), 6.94 (d, 1H, 8.8 Hz), 5.40 (dd, 1H, J 10.4, 2.1 Hz), 3.04 (m, 1H), 2.80 (m, 1H), 2.24 (m, 1H), 1.95 (m, 1H).

Example 74

2-(2-Chlorophenyl)-6-(5-nitropyridin-2-yloxy)chroman-4-ol 2-(2-Chlorophenyl)-6-(5-nitropyridin-2-yloxy)chroman-4-ol was prepared as described for 5-nitro-2-(2-phenylchroman-6-yloxy)pyridine in Example 1(b) starting from 520 mg of 2-(2-chlorophenyl)chroman-4,6-diol (Example 68(b)). The product was recrystallised from 2-propanol. $^1$H NMR (300 MHz, d$_6$-DMSO) δ: 9.04 (d, 1H, J 2.9 Hz), 8.61 (dd, 1H, J 9.1, 2.9 Hz), 7.68 (dd, 1H, J 7.6, 1.8 Hz), 7.51-7.40 (m, 3H), 7.27 (d, 1H, J 2.9 Hz), 7.23 (d, 1H, J 9.1 Hz), 7.04 (dd, 1H, J 8.8, 2.9 Hz), 6.92 (d, 1H, J 8.8 Hz), 5.59 (d, 1H, J 10.6 Hz), 5.02 (m, 1H), 2.40 (m, 1H), 1.93 (m, 1H).

Example 75

5-Nitro-2-[2-(4-Fluorophenyl)chroman-6-yloxy]pyridine a) 6-Hydroxy-2-(4-fluorophenyl)chroman-4-one 6-Hydroxy-2-(4-fluorophenyl)chroman-4-one was prepared as described for 2-(3-fluorophenyl)-6-hydroxychroman-4-one in Example 9(a) starting from 2.0 g of 2',5'-dihydroxyacetophenone and 1.6 ml of 4-fluorobenzaldehyde. The product was recrystallised from acetic acid. $^1$H NMR (400 MHz, d$_6$-DMSO) δ: 7.59 (m, 2H), 7.27 (m, 2H), 7.14 (d, 1H, J 3.1 Hz), 7.05 (dd, 1H, J 8.9, 3.1 Hz), 6.96 (d, 1H, J 8.9 Hz), 5.56 (dd, 1H, J 13.2, 2.8 Hz), 3.18 (dd, 1H, J-16.9, 13.2 Hz), 2.77 (dd, 1H, J –16.9, 2.8 Hz).

b) 2-(4-Fluorophenyl)chroman-4,6-diol 2-(4-Fluorophenyl)chroman-4,6-diol was prepared as described for 2-phenylchroman-4,6-diol in Example 8(a) starting from 1,5 g of 2-(4-fluorophenyl)-6-hydroxychroman-4-one. $^1$H NMR (400 MHz, d$_6$-DMSO) δ: 8.84 (s, 1H), 7.48 (m, 2H), 7.21 (m, 2H), 6.89 (d, 1H, J 2.7 Hz), 6.59 (d, 1H, J 8.7 Hz), 6.54 (dd, 1H, J 8.7, 2.7 Hz), 5.42 (bs, 1H), 5.12 (d, 1H, J 10.7 Hz), 4.87 (m, 1H), 2.25 (m, 1H), 1.89 (m, 1H).

c) 2-(4-Fluorophenyl)chroman-6-ol 2-(4-Fluorophenyl)chroman-6-ol was prepared as described for 2-(3-fluorophenyl)chroman-6-ol in Example 9(c) starting from 480 mg of 2-(4-fluorophenyl)-chroman-4,6-diol. $^1$H NMR (400 MHz, CDCl$_3$) δ: 7.38 (m, 2H), 7.06 (m, 2H), 6.77 (d, 1H, J 8.6 Hz), 6.61 (dd, 1H, J 8.6, 2.9 Hz), 6.57 (d, 1H, 8.6 Hz), 4.97 (dd, 1H, J 10.2, 2.4 Hz), 2.95 (ddd, 1H, J −16.8, 11.4, 6.2 Hz), 2.74 (ddd, 1H, J −16.8, 5.3, 3.1 Hz), 2.15 (m, 1H), 2.05 (m, 1H).

d) 2-[2-(4-Fluorophenyl)chroman-6-yloxy]-5-nitropyridine

2-[2-(4-Fluorophenyl)chroman-6-yloxy]-5-nitropyridine was prepared as described for 5-nitro-2-(2-phenylchroman-6-yloxy)pyridine in Example 1(b) starting from 160 mg of 2-(4-fluorophenyl)chroman-6-ol. The product was purified on preparative TLC-plate covered with silica gel using heptane-ethyl acetate (4:1) as an eluant. $^1$H NMR (400 MHz, d$_6$-DMSO) δ: 9.04 (dd, 1H, J 2.9, 0.4 Hz), 8.60 (dd, 1H, J 9.1, 2.9 Hz), 7.51 (m, 2H), 7.24 (m, 1H), 7.20 (dd, 1H, J 9.1, 0.4 Hz), 7.01 (d, 1H, J 2.8 Hz), 6.96 (dd, 1H, J 8.7, 2.8 Hz), 6.91 (d, 1H, 8.7 Hz), 5.15 (dd, 1H, J 10.3, 2.2 Hz), 2.94 (m, 1H), 2.76 (m, 1H), 2.17 (m, 1H), 2.01 (m, 1H).

Example 76

6-[2-(4-Fluorophenyl)chroman-6-yloxy]pyridin-3-ylamine

6-[2-(4-Fluorophenyl)chroman-6-yloxy]pyridin-3-ylamine was prepared as described for 5-amino-2-(2-phenylchroman-6-yloxy)pyridine in Example 26 starting from 3.04 g of 2-[2-(4-fluorophenyl)chroman-6-yloxy]-5-nitropyridine (Example 75(d)). $^1$H NMR (400 MHz, d$_6$-DMSO) δ: 7.52-7.47 (m, 3H), 7.24 (m, 2H), 7.05 (dd, 1H, J 8.6, 3.0 Hz), 6.84-6.68 (m, 4H), 5.09 (dd, 1H, J 10.2, 2.1 Hz), 5.00 (bs, 2H), 2.93 (m, 1H), 2.69 (m, 1H), 2.13 (m, 1H), 1.98 (m, 1H).

Example 77

N-{6-[2-(4-Fluorophenyl)chroman-6-yloxy]pyridin-3-yl}methane Sulfonamide

N-{6-[2-(4-Fluorophenyl)chroman-6-yloxy]pyridin-3-yl}methane sulfonamide was prepared as described for N-[6-(2-phenylchroman-6-yloxy)pyridin-3-yl] methane sulfonamide in Example 46 starting from 442 mg of 6-[2-(4-fluorophenyl)-chroman-6-yloxy]-pyridin-3-ylamine (Example 76). The product was passed through silica gel using ethyl acetate-heptane (10:3) as an eluant and then crystallised from diethyl ether. $^1$H NMR (400 MHz, CDCl$_3$) δ: 8.09 (d, 1H, J 2.8 Hz), 7.72 (dd, 1H, J 8.9, 2.8 Hz), 7.40 (m, 2H), 7.08 (m, 2H), 6.92-6.87 (m, 4H), 6.74 (s, 1H), 5.03 (dd, 1H, J 10.4, 2.3 Hz), 3.01 (m, 1H), 3.00 (s, 3H), 2.80 (m, 1H), 2.19 (m, 1H), 2.07 (m, 1H).

Example 78

2-[2-(2,3-Difluorophenyl)chroman-6-yloxy]5-nitropyridine a) 2-(2,3-Difluorophenyl)-6-hydroxychroman-4-one 2-(2,3-Difluorophenyl)-6-hydroxychroman-4-one was prepared as described for 2-(3-fluorophenyl)-6-hydroxychroman-4-one in Example 9(a) starting from 3.0 g of 2',5'-dihydroxyacetophenone and 2.6 ml of 2,3-difluorobenzaldehyde. $^1$H NMR (400 MHz, d$_6$-DMSO) δ: 9.51 (s, 1H), 7.53-7.46 (m, 2H), 7.31 (m, 1H), 7.14 (d, 1H, J 3.0 Hz), 7.05 (dd, 1H, 3 8.8, 3.0 Hz), 6.96 (d, 1H, J 8.8 Hz), 5.82 (dd, 1H, J 13.4, 2.8 Hz), 3.26 (dd, 1H, J −16.9, 13.4 Hz), 2.79 (dd, 1H, J −16.9, 2.8 Hz).

b) 2-(2,3-Difluorophenyl)chroman-4,6-diol 2-(2,3-Difluorophenyl)chroman-4,6-diol was prepared as described for 2-phenylchroman-4,6-diol in Example 8(a) starting from 2.91 g of 2-(2,3-difluorophenyl)-6-hydroxychroman-4-one. $^1$H NMR (400 MHz, d$_6$-DMSO) δ: 8.88 (s, 1H), 7.45-7.36 (m, 2H), 7.28 (m, 1H), 6.89 (d, 1H, J 2.8 Hz), 6.61 (d, 1H, J 8.7 Hz), 6.55 (dd, 1H, J 8.7, 2.8 Hz), 5.49 (bs, 1H), 5.40 (dd, 1H, J 11.8, 1.4 Hz), 4.90 (m, 1H), 2.28 (m, 1H), 1.99 (m, 1H).

c) 2-(2,3-Difluorophenyl)chroman-6-ol 2-(2,3-Difluorophenyl)chroman-6-ol was prepared as described for 2-(3-fluorophenyl)chroman-6-ol in Example 9(c) starting from 1.5 g of 2-(2,3-difluorophenyl)chroman-4,6-diol. $^1$H NMR (400 MHz, d$_6$-DMSO) δ: 8.85 (s, 1H), 7.41 (m, 1H), 7.33 (m, 1H), 7.26 (m, 1H), 6.64 (dd, 1H, 9.0, 2.8 Hz), 6.54-6.51 (m, 2H), 5.25 (dd, 1H, J 10.2, 2.2 Hz), 2.93 (m, 1H), 2.66 (m, 1H), 2.14 (m, 1H), 2.01 (m, 1H).

d) 2-[2-(2,3-Difluorophenyl)chroman-6-yloxy]-5-nitropyridine

2-[2-(2,3-Difluorophenyl)chroman-6-yloxy]-5-nitropyridine was prepared as described for 5-nitro-2-(2-phenylchroman-6-yloxy)pyridine in Example 1(b) starting from 1.88 g of 2-(2,3-difluorophenyl)chroman-6-ol. $^1$H NMR (400 MHz, d$_6$-DMSO) δ: 9.04 (d, 1H, J 3.0 Hz), 8.60 (dd, 1H, J 9.1, 3.0 Hz), 7.45 (m, 1H), 7.38 (m, 1H), 7.30 (m, 1H), 7.21 (d, 1H, 9.1 Hz), 7.03 (d, 1H, J 2.7 Hz), 6.98 (dd, 1H, J 8.8, 2.7 Hz), 6.92 (d, 1H, 8.8 Hz), 5.42 (dd, 1H, J 10.4, 2.3 Hz), 3.04 (m, 1H), 2.79 (m, 1H) 2.21 (m, 1H), 2.08 (m, 1H).

Example 79

2-(2,6-Difluorophenyl)-6-(5-nitropyridin-2-yloxy)chroman-4-ol a) 6-Hydroxy-2-(2,6-difluorophenyl)chroman-4-one

6-Hydroxy-2-(2,6-Difluorophenyl)chroman-4-one was prepared as described for 2-(3-fluorophenyl)-6-hydroxychroman-4-one in Example 9(a) starting from 3.0 g of 2',5'-dihydroxyacetophenone and 2.6 ml of 2,6-difluorobenzaldehyde. The product was triturated from ethanol. $^1$H NMR (400 MHz, d$_6$-DMSO) δ: 7.55 (m, 1H) 7.22-7.18 (m, 2H), 7.14 (d, 1H, J 3.0 Hz), 7.03 (dd, 1H, J 8.9, 3.0 Hz), 6.93 (d, 1H, J 8.9 Hz), 5.84 (dd, 1H, J 14.0, 3.0 Hz), 3.38 (dd, 1H, J −17.0, 14.0 Hz), 2.80 (dd, 1H, J −17.0, 3.0 Hz).

b) 2-(2,6-Difluorophenyl)chroman-4,6-diol 2-(2,6-Difluorophenyl)chroman-4,6-diol was prepared as described for 2-phenylchroman-4,6-diol in Example 8(a) starting from 4.45 g of 2-(2,6-difluorophenyl)-6-hydroxychroman-4one. $^1$H NMR (400 MHz, d$_6$-DMSO) δ: 8.87 (s, 1H), 7.48 (m, 1H), 7.17-7.13 (m, 2H), 6.90 (d, 1H, J 2.9 Hz), 6.55-6.54 (m, 2H), 5.46 (dd, 1H, J 12.2, 1.8 Hz), 4.87 (m, 1H), 2.37 (m, 1H), 2.23 (m, 1H).

c) 2-(2,6-Difluorophenyl)-6-(5-nitropyridin-2-yloxy)chroman-4-ol 2-(2,6-Difluorophenyl)-6-(5-nitropyridin-2-yloxy)chroman-4-ol was prepared as described for 5-nitro-2-(2-phenylchroman-6-yloxy)pyridine in Example 1(b) starting from 1.9 g of 2-(2,6-difluorophenyl)chroman-4,6-diol. $^1$H NMR (300 MHz, $d_6$-DMSO) δ: 9.03 (d, 1H, J 2.9 Hz), 8.61 (dd, 1H, J 9.1, 2.9 Hz), 7.52 (m, 1H), 7.26-7.16 (m, 4H), 7.01 (dd, 1H, J 8.8, 2.9 Hz), 6.83 (d, 1H, 8.8 Hz), 5.69-5.64 (m, 2H), 4.98 (m, 1H), 2.37 (m, 1H), 2.29 (m, 1H).

Example 80

6-(5-Nitropyridin-2-yloxy)-2-(2-trifluoromethylphenyl)chroman-4-ol a) 6-Hydroxy-2-(2-trifluoromethylphenyl)chroman-4-one 6-Hydroxy-2-(2-trifluoromethylphenyl)chroman-4-one was prepared as described for 2-(3-fluorophenyl)-6-hydroxychroman-4-one in Example 9(a) starting from 3.0 g of 2',5'-dihydroxyacetophenone and 3.0 ml of 2-trifluoromethylbenzaldehyde. The product was triturated from ethanol. $^1$H NMR (300 MHz, $d_6$-DMSO) δ: 9.48 (s, 1H), 8.07 (m, 1H), 7.86-7.79 (m, 2H), 7.66 (m, 1H), 7.15 (d, 1H, J 3.0 Hz), 7.06 (dd, 1H, J 8.8, 3.0 Hz), 6.95 (d, 1H, J 8.8 Hz), 5.70 (dd, 1H, J 13.8, 2.4 Hz), 3.38 (dd, 1H, J −16.9, 13.8 Hz), 2.66 (dd, 1H, J −16.9, 3.0 Hz).

b) 2-(2-Trifluoromethylphenyl)chroman-4,6-diol 2-(2-Trifluoromethylophenyl)chroman-4,6-diol was prepared as described for 2-phenylchroman-4,6-diol in Example 8(a) starting from 1.43 g of 2-(2-trifluoromethylphenyl)-6-hydroxychroman-4-one. $^1$H NMR (300 MHz, $d_6$-DMSO) δ: 8.89 (s, 1H), 7.83 (m, 1H), 7.79-7.74 (m, 2H), 7.58 (m, 1H), 6.90 (d, 1H, J 2.7 Hz), 6.61 (d, 1H, J 8.9 Hz), 6.56 (dd, 1H, J 8.7, 2.7 Hz), 5.51 (d, 1H, J 6.5 Hz), 5.34 (d, 1H, J 11.6 Hz), 4.88 (m, 1H), 2.21 (m, 1H), 1.95 (m, 1H).

c) 6-(5-Nitropyridin-2-yloxy)-2-(2-trifluoromethylphenyl)chroman-4-ol 6-(5-Nitropyridin-2-yloxy)-2-(2-trifluoromethylphenyl)chroman-4-ol was prepared as described for 5-nitro-2-(2-phenylchroman-6-yloxy)pyridine in Example 1(b) starting from 350 mg of 2-(2-trifluoromethylphenyl)chroman-4,6-diol. $^1$H NMR (400 MHz, $d_6$-DMSO) δ: 9.04 (d, 1H, J 2.8 Hz), 8.62 (dd, 1H, J 9.1, 2.8 Hz), 7.89 (m, 1H), 7.82-7.78 (m, 2H), 7.62 (m, 1H), 7.28 (d, 1H, J 2.7 Hz), 7.24 (d, 1H, 9.1 Hz), 7.04 (dd, 1H, J 8.7, 2.7 Hz), 6.90 (d, 1H, J 8.7 Hz), 5.7 (bs, 1H), 5.38 (d, 1H, J 11.6 Hz), 5.01 (m, 1H), 2.29 (m, 1H), 2.05 (m, 1H).

Example 81

2-[3-(3-Fluorophenyl)chroman-7-yloxy]-5-nitropyridine a) 2-(3-Fluorophenyl)-1-(2-hydroxy-4-methoxyphenyl)ethanone (3-Fluorophenyl)acetic acid (3.7 g) and 3-methoxyphenol (3.0 g) were dissolved into $BF_3Et_2O$ (60 ml, 20 eq) under argon. The mixture was stirred at 60-70° C. until disappearance of the starting materials (9 h) and poured into large volume of ice water. After extraction with ethyl acetate the combined organic layers were washed with water, dried and evaporated. The crude product was purified by column chromatography using $CH_2Cl_2$ as an eluant. $^1$H NMR (400 MHz, $d_6$-DMSO) δ: 12.41 (br s, 1H), 8.02 (d, 1H, J 9.0 Hz), 7.34-7.38 (m, 1H), 7.09-7.13 (m, 3H), 6.56 (dd, 1H, J 9.0, 2.5 Hz), 6.49 (d, 1H, J 2.5 Hz), 4.41 (s, 2H), 3.83 (s, 3H).

b) 3-(3-Fluorophenyl)-7-methoxychromen-4-one 2-(3-Fluorophenyl)-1-(2-hydroxy-4-methoxyphenyl)ethanone (1.76 g) was dissolved in pyridine (88 ml). Piperidine (8.8 ml) and triethylorthoformate (88 ml) were added and the mixture was stirred at 120° C. for 3.5 hours. After pouring the mixture into water and acidification with conc. HCl the crude product was filtered. Purification by column chromatography using heptane-ethyl acetate (7:3) as an eluant afforded 3-(3-fluorophenyl)-7-methoxychromen-4-one. $^1$H NMR (400 MHz, $d_6$-DMSO) δ: 8.57 (s, 1H), 8.06 (d, 1H, J 8.9 Hz), 7.45-7.50 (m, 3H), 7.21-7.25 (m, 1H), 7.20 (d, 1H, J 2.4 Hz), 7.12 (dd, 1H, J 8.9, 2.4 Hz), 3.92 (s, 3H).

c) 3-(3-Fluorophenyl)-7-hydroxychromen-4-one 3-(3-Fluorophenyl)-7-methoxychromen-4one (320 mg) was refluxed with 47% HBr (18 ml) until disappearance of the starting material. The mixture was poured into water and the precipitate was filtrated and dried yielding 3-(3-fluorophenyl)-7-hydroxychromen-4-one. $^1$H NMR (400 MHz, $d_6$-DMSO) δ: 10.87 (s, 1H), 8.49 (s, 1H), 7.99 (d, 1H, J 8.7 Hz), 7.43-7.49 (m, 3H), 7.20-7.24 (m, 1H), 6.97 (dd, 1H, J 8.7, 2.2 Hz), 6.90 (d, 1H, J 2.2 Hz).

d) 3-(3-Fluorophenyl)chroman-7-ol 3-(3-Fluorophenyl)-7-hydroxychromen-4-one (160 mg) was dissolved in ethanol (40 ml) and 10% palladium on carbon (400 mg) was added. The reaction mixture was hydrogenated for 6 hours at normal pressure and room temperature. It was then filtered through Celite and washed with ethanol. The solvent was evaporated under reduced pressure to give 3-(3-fluorophenyl)chroman-7-ol. $^1$H NMR (400 MHz, $d_6$-DMSO) δ: 9.19 (br s, 1H), 7.38 (m, 1H), 7.17-7.21 (m, 2H), 7.08 (m, 1H), 6.88 (d, 1H, J 8.2 Hz), 6.30 (dd, 1H, J 8.2, 2.4 Hz), 6.20 (d, 1H, J 2.4 Hz), 4.22 (dd, 1H, J 10.3, 3.6 Hz), 4.02 (t, 1H, 10.3 Hz), 3.20 (m, 1H), 2.90 (m, 2H).

e) 2-[3-(3-Fluorophenyl)chroman-7-yloxy]-5-nitropyridine

2-[3-(3-Fluorophenyl)chroman-7-yloxy]-5-nitropyridine was prepared as described for 5-nitro-2-(2-phenylchroman-6-yloxy)pyridine in Example 1(b) using 125 mg of 3-(3-fluorophenyl)-chroman-7-ol. The product was recrystallised from ethanol. $^1$H NMR (400 MHz, $CDCl_3$) δ: 9.07 (d, 1H, J 2.8 Hz), 8.47 (dd, 1H, J 9.0, 2.8 Hz), 7.33 (m, 1H), 7.16 (d, 1H, J 8.9 Hz), 6.95-7.06 (m, 4H), 6.69-6.71 (m, 2H), 4.38 (dd, 1H, J 10.6, 4.3 Hz), 4.06 (t, 1H, 10.6 Hz), 3.30 (m, 1H), 3.06 (m, 2H).

Example 82

5-Nitro-2-(3-phenylchroman-7-yloxy)pyridine a) 7-Hydroxy-3-phenylchromen-4-one

7-Hydroxy-3-phenylchromen-4-one is commercially available or can be synthesised by methods described for 3-(3-fluorophenyl)-7-hydroxychromen-4-one (Example 81(a-c)). $^1$H NMR spectrum as reported in the literature (*Synth. Commun.*, 2000, 30(3), 469-484).

b) 3-Phenylchroman-7-ol

3-Phenylchroman-7-ol was prepared as described for 3-(3-fluorophenyl)-chroman-7-ol in Example 81(d) using 0.5 g of 7-hydroxy-3-phenylchromen-4-one. $^1$H NMR (400 MHz, $d_6$-DMSO) δ: 8.18 (br s, 1H), 7.31-7.34 (m, 4H), 7.25-7.27 (m, 1H), 6.88 (d, 1H, J 8.2 Hz), 6.30 (dd, 1H, J 8.2, 2.4 Hz), 6.20 (d, 1H, J 2.4 Hz), 4.21 (dd, 1H, J 10.3, 3.6 Hz), 4.00 (t, 1H, 10.3 Hz), 3.13 (m, 1H), 2.84-2.87 (m, 2H).

c) 5-Nitro-2-(3-phenylchroman-7-yloxy)pyridine

5-Nitro-2-(3-phenylchroman-7-yloxy)pyridine was prepared as described for 5-nitro-2-(2-phenylchroman-6-yloxy)pyridine in Example 1(b) using 200 mg of 3-phenylchroman-7-ol. $^1$H NMR (400 MHz, $d_6$-DMSO) δ: δ: 9.05 (d, 1H, J 2.9 Hz), 8.61 (dd, 1H, J 9.1, 2.9 Hz), 7.34-7.38 (m, 4H), 7.27-7.30 (m, 1H), 7.22 (m, 2H), 6.70-6.74 (m, 2H), 4.31 (dd, 1H, J 10.4, 3.5 Hz), 4.12 (t, 1H, 10.4 Hz), 3.24 (m, 1H), 3.01-3.11 (m, 2H).

Example 83

5-Methoxy-2-(3-phenylchroman-7-yloxy)phenylamine Hydrochloride a) 7-(4-Methoxy-2-nitrophenoxy)-3-phenylchroman 7-(4-Methoxy-2-nitrophenoxy)-3-phenylchroman was prepared as described for 6-(4-methoxy-2-nitrophenoxy)-2-phenylchroman in Example 3(a) using 0.5 g of 3-phenylchroman-7-ol. $^1$H NMR (400 MHz, $d_6$-DMSO) δ: 7.60 (d, 1H, J 3.1 Hz), 7.35 (m, 4H), 7.32 (dd, 1H, J 9.1, 3.1 Hz), 7.27-7.29 (m, 1H), 7.21 (d, 1H, J 9.1 Hz), 7.12 (d, 1H, J 8.3 Hz), 6.48 (dd, 1H, J 8.3, 2.5 Hz), 6.38 (d, 1H, J 2.5 Hz), 4.26 (dd, 1H, J 10.4, 3.5 Hz), 4.08 (t, 1H, J 10.4 Hz), 3.85 (s, 3H), 3.20 (m, 1H), 2.90-3.04 (m, 2H).

b) 5-Methoxy-2-(3-phenylchroman-7-yloxy)phenylamine Hydrochloride

5-Methoxy-2-(3-phenylchroman-7-yloxy)phenylamine hydrochloride was prepared as described for 5-methoxy-2-(2-phenylchroman-6-yloxy)phenylamine hydrochloride in Example 3(b) using 310 mg of 7-(4-methoxy-2-nitrophenoxy)-3-phenylchroman. $^1$H NMR (400 MHz, $d_6$-DMSO) δ: 7.32-7.35 (m, 4H), 7.23-7.29 (m, 1H), 7.05 (d, 1H, J 8.4 Hz), 6.76 (d, 1H, J 8.8 Hz), 6.46 (d, 1H, J 2.8 Hz), 6.43 (d, 1H, J 8.4, 2.5 Hz), 6.28 (d, 1H, J 2.5 Hz), 6.24 (dd, 1H, J 8.8, 2.8 Hz), 4.24 (dd, 1H, J 10.4, 3.4 Hz), 4.05 (t, 1H, J 10.4 Hz), 3.18 (m, 1H), 2.88-3.01 (m, 2H).

Example 84

5-Nitro-2-(2-phenyl-2,3-dihydrobenzo[1,4]oxathiin-6-yloxy)pyridine a) 2-(2-Hydroxy-1-phenylethylsulfanyl)benzene-1,4-diol

To a stirred solution of 2-mercaptobenzene-1,4-diol (0.5 g) and potassium carbonate (0.49 g) in water (5 ml) was added 2-phenyloxirane (0.40 ml) under argon. The mixture was stirred at room temperature for 2.5 hours and then treated with 2 M HCl and extracted with ethyl acetate. The combined organic layers were washed with water and brine, dried and evaporated. The crude product was purified by column chromatography using heptane-ethyl acetate (1:1) as an eluant. $^1$H NMR (400 MHz, $d_6$-DMSO) δ: 8.94 (br s, 1H), 8.72 (br s, 1H), 7.24-7.37 (m, 5H), 6.62-6.65 (m, 2H), 6.47 (dd, 1H, J 8.6, 2.8 Hz), 4.97 (br s, 1H), 4.34 (m, 1H), 3.72 (m, 2H).

b) 2-Phenyl-2,3-dihydrobenzo[1,4]oxathiin-6-ol

A solution of 2-(2-hydroxy-1-phenylethylsulfanyl)benzene-1,4-diol (0.83 g) in dry toluene (60 ml) was stirred with Amberlyst 15 (0.5 g) at 60° C. until disappearance of the starting material. After the mixture was filtered and solvent evaporated the crude product was purified by column chromatography using heptane-ethyl acetate (1:1) as an eluant. $^1$H NMR (400 MHz, CDCl$_3$) δ: 7.41 (m, 4H), 7.33-7.40 (m, 1H), 6.81 (d, 1H, J 8.7 Hz), 6.61 (d, 1H, J 3.0 Hz), 6.51 (dd, 1H, J 8.7, 3.0 Hz), 5.10 (dd, 1H, J 9.6, 1.9 Hz), 3.28 (dd, 1H, J 13.0, 9.6 Hz), 3.06 (dd, 1H, J 13.0, 1.9 Hz).

c) 5-Nitro-2-(2-phenyl-2,3-dihydrobenzo[1,4]oxathiin-6-yloxy)pyridine

5-Nitro-2-(2-phenyl-2,3-dihydrobenzo[1,4]oxathiin-6-yloxy)pyridine was prepared as described for 5-nitro-2-(2-phenylchroman-6-yloxy)pyridine in Example 1(b) using 269 mg 2-phenyl-2,3-dihydrobenzo[1,4]oxathiin-6-ol. The product was recrystallised from ethanol. $^1$H NMR (400 MHz, CDCl$_3$) δ: 9.07 (d, 1H, J 2.8 Hz), 8.47 (dd, 1H, J 9.1, 2.8 Hz), 7.43 (m, 4H), 7.37-7.41 (m, 1H), 7.02 (d, 1H, J 9.1 Hz), 6.99 (d, 1H, J 8.9 Hz), 6.95 (d, 1H, J 2.8 Hz), 6.82 (dd, 1H, J 8.9, 2.8 Hz), 5.21 (dd, 1H, J 9.7, 1.9 Hz), 3.31 (dd, 1H, 13.2, 9.7 Hz), 3.11 (dd, 1H, 13.2, 1.9 Hz).

Example 85

5-Nitro-2-(4-oxo-2-phenyl-3,4-dihydrobenzo[1.4]oxathiin-6-yloxy)pyridine

To 5-nitro-2-(2-phenyl-2,3-dihydrobenzo[1,4]oxathiin-6-yloxy)pyridine (214 mg) in methanol (80 ml) at 60° C., NaIO$_4$ (total 2.5 eq) was added in small portions until disappearance of the starting material. The mixture was poured into water and precipitate was filtered and washed with water. The crude product was purified by column chromatography using heptane-ethyl acetate (1:1) as an eluant. $^1$H NMR (400 MHz, CDCl$_3$) δ: 9.02 (d, 1H, J 2.8 Hz), 8.51 (dd, 1H, J 9.1, 2.8 Hz), 7.45-7.56 (m, 6H), 7.32 (dd, 1H, J 9.0, 2.8 Hz), 7.21 (d, 1H, J 9.0 Hz), 7.10 (d, 1H, J 9.1 Hz), 5.77 (dd, 1H, J 12.0, 1.5 Hz), 3.34 (dd, 1H, 14.4, 1.5 Hz), 3.13 (dd, 1H, 14.4, 12.0 Hz).

Example 86

2-(4,4-Dioxo-2-phenyl-3,4-dihydro-2-benzo[1,4]oxathiin-6-yloxy)-5-nitropyridine To stirred solution of 5-nitro-2-(2-phenyl-2,3-dihydrobenzo[1,4]oxathiin-6-yloxy)pyridine (150 mg) in AcOH (3.7 ml) and water (1.2 ml) was added $KMnO_4$ (125 mg) in an ice/water bath. The mixture was stirred at room temperature for 1.5 hours, then water (5 ml) and 30% $H_2O_2$ were added until decomposition of excess $KMnO_4$ was complete. The mixture was diluted with additional water (20 ml). The white precipitate was filtered, washed with water and dried to give 2-(4,4-dioxo-2-phenyl-3,4-dihydro-2-benzo[1,4]oxathiin-6-yloxy)-5-nitropyridine. $^1H$ NMR (400 MHz, $CDCl_3$) δ: 9.03 (d, 1H, J 2.8 Hz), 8.52 (dd, 1H, J 9.0, 2.8 Hz), 7.68 (d, 1H, J 2.8 Hz), 7.46-7.52 (m, 5H), 7.33 (dd, 1H, J 9.1, 2.8 Hz), 7.17 (d, 1H, J 9.1 Hz), 7.11 (d, 1H, J 9.0 Hz), 5.87 (dd, 1H, J 12.2, 1.6 Hz), 3.76 (dd, 1H, 14.1, 12.2 Hz), 3.55 (dd, 1H, 14.1, 1.6 Hz).

Example 87

5-Nitro-2-[2-(4-nitrophenyl)chroman-6-yloxy]pyridine a) 6-Hydroxy-2-(4-nitrophenyl)chroman-4-one

6-Hydroxy-2-(4-nitrophenyl)chroman-4-one was prepared as described for 6-hydroxy-2-(3-fluorophenyl)chroman-4-one in Example 9(a). The product was recrystallised from ethanol. $^1H$ NMR (400 MHz, $d_6$-DMSO) δ: 9.48 (s, 1H), 8.29 (d, 2H, J 6.9 Hz), 7.83 (d, 2H, J 6.9 Hz), 7.13 (d, 1H J 2.9 Hz), 7.06 (dd, 1H, J 8.8, 2.9 Hz), 7.01 (d, 1H, J 8.8 Hz), 5.77 (dd, 1H, J 13.0, 3.0 Hz), 3.15 (dd, 1H, J 16.8, 13.0 Hz), 2.89 (dd, 1H, J 16.8, 3.0 Hz).

b) 2-(4-Nitrophenyl)chroman-4,6-diol 2-(4-Nitrophenyl)chroman-4,6-diol was prepared as described for 2-phenylchroman-4,6-diol in Example 8(a) staring from 6-hydroxy-2-(4-nitrophenyl)-chroman-4-one. $^1H$ NMR (300 MHz, $d_6$-DMSO) δ: 8.86 (s, 1H), 8.26 (d, 2H, J 6.9 Hz), 7.74 (d, 2H, J 6.9 Hz), 6.89 (d, 1H J 2.8 Hz), 6.65 (d, 1H, J 8.6 Hz), 6.56 (d, 1H, J 8.6, 2.8 Hz), 5.46 (d, 1H, J 6.9 Hz), 5.32 (d, 1H, J 10.5 Hz), 4.86-4.94 (m, 1H), 2.31-2.38 (m, 1H), 1.78-1.89 (m, 1H).

c) 2-(4-Nitrophenyl)chroman-6-ol 2-(4-Nitrophenyl)chroman-6-ol was prepared as described for 2-(3-fluorophenyl)chroman-6-ol in Example 9(c) starting from 2-(4-nitrophenyl)chroman-4,6-diol. $^1H$ NMR (400 MHz, $d_6$-DMSO) δ: 8.84 (s, 1H), 8.26 (d, 2H, J 6.9 Hz), 7.71 (d, 2H, J 6.9 Hz), 6.69 (d, 1H, J 8.6 Hz), 6.53 (dd, 1H, J 8.6, 2.8 Hz), 6.50 (d, 1H, J 2.8 Hz), 5.19 (dd, 1H, J 9.9, 2.2 Hz), 2.87-2.91 (m, 1H), 2.61-2.66 (m, 1H), 2.16-2.21 (m, 1H), 1.89-1.93 (m, 1H).

d) 5-Nitro-2-[2-(4-nitrophenyl)chroman-6-yloxy]pyridine

5-Nitro-2-[2-(4-nitrophenyl)chroman-6-yloxy]pyridine was prepared as described for 5-nitro-2-(2-phenylchroman-6-yloxy)pyridine in Example 1(b) starting from 2-(4-nitrophenyl)chroman-6-ol. $^1H$ NMR (300 MHz, $d_6$-DMSO) δ: 9.04 (d, 1H, J 2.9 Hz), 8.60 (dd, 1H, J 9.1, 2.9 Hz), 8.29 (d, 2H, J 6.9 Hz), 7.76 (d, 2H, J 6.9 Hz), 7.21 (d, 1H, J 9.1 Hz), 6.98-7.02 (m, 3H), 5.35 (dd, 1H, J 9.9, 2.2 Hz), 2.96-3.05 (m, 1H), 2.73-2.78 (m, 1H), 2.24-2.29 (m, 1H), 1.96-2.04 (m, 1H).

Example 88

6-[2-(4-Aminophenyl)chroman-6-yloxy]-pyridin-3-ylamine

6-[2-(4-Aminophenyl)chroman-6-yloxy]-pyridin-3-ylamine was prepared as described for 5-amino-2-(2-phenylchroman-6-yloxy)pyridine in Example 26 using 100 mg 5-nitro-2-[2-(4-nitrophenyl)chroman-6-yloxy]pyridine (Example 87(d)) and 665 mg of Zn. $^1H$ NMR (400 MHz, $d_6$-DMSO) δ: 7.50 (d, 1H, J 2.9 Hz), 7.07 (d, 2H, 8.4 Hz), 7.04 (dd, 1H, J 8.6, 2.9 Hz), 6.71 (s, 3H), 6.68 (d, 1H, J 8.6 Hz), 6.56 (d, 2H, J 8.4 Hz), 5.07 (s, 2H), 4.99 (s, 2H), 4.84 (dd, 1H, J 9.7, 2.3 Hz), 2.86-2.95 (m, 1H), 2.66-2.71 (m, 1H), 1.95-2.05 (m, 2H).

Example 89

5-Nitro-2-[2-(2-nitrophenyl)chroman-6-yloxy]pyridine a) 6-Hydroxy-2-(2-nitrophenyl)chroman-4-one

6-Hydroxy-2-(2-nitrophenyl)chroman-4-one was prepared as described for 6-hydroxy-2-(3-fluorophenyl)chroman-4-one in Example 9(a). $^1H$ NMR (400 MHz, $d_6$-DMSO) δ: 9.49 (s, 1H), 8.05-8.06 (m, 1H), 7.96-7.98 (m, 1H), 7.83-7.87 (m, 1H), 7.65-7.69 (m, 1H), 7.14 (d, 1H, J 3.1 Hz), 7.05 (dd, 1H, J 8.8, 3.1 Hz), 6.91 (d, 1H, J 8.8 Hz), 5.69 (dd, 1H, J 13.0, 2.6 Hz), 3.22 (dd, 1H, J 16.8, 13.0 Hz), 2.98 (dd, 1H, J 16.8, 2.6 Hz).

b) 2-(2-Nitrophenyl)chroman-4,6-diol 2-(2-Nitrophenyl)chroman-4,6-diol was prepared as described for 2-phenylchroman-4,6-diol in Example 8(a) starting from 6-hydroxy-2-(2-nitrophenyl)-chroman-4-one. $^1H$ NMR (300 MHz, $d_6$-DMSO) δ: 8.87 (s, 1H), 7.99-8.02 (m, 1H), 7.77-7.86 (m, 2H), 7.59-7.64 (m, 1H), 6.89 (d, 1H, J 2.4 Hz), 6.56-6.57 (m, 2H), 5.51-5.55 (m, 2H), 4.85-4.92 (m, 1H), 2.42-2.47 (m, 1H), 1.85-1.96 (m, 1H).

c) 2-(2-Nitrophenyl)chroman-6-ol 2-(2-Nitrophenyl)chroman-6-ol was prepared as described for 2-(3-fluorophenyl)chroman-6-ol in Example 9(c) starting from 2-(2-nitrophenyl)chroman-4,6-diol. $^1H$ NMR (400 MHz, $d_6$-DMSO) δ: 8.85 (s, 1H), 8.00 (d, 1H, J 8.0 Hz), 7.79-7.80 (m, 2H), 7.59-7.63 (m, 1H), 6.59-6.62 (m, 1H), 6.50-6.53 (m, 2H), 5.36 (dd, 1H, J 10.2, 2.0 Hz), 2.89-2.93 (m, 1H), 2.67-2.73 (m, 1H), 2.26-2.31 (m, 1H), 1.90-1.95 (m, 1H).

d) 5-Nitro-2-[2-(2-nitrophenyl)chroman-6-yloxy]pyridine

5-Nitro-2-[2-(2-nitrophenyl)chroman-6-yloxy]pyridine was prepared as described for 5-nitro-2-(2-phenylchroman-6-yloxy)pyridine in Example 1(b) starting from 2-(2-nitrophenyl)chroman-6-ol. $^1H$ NMR (400 MHz, $d_6$-DMSO) δ: 9.04 (d, 1H, J 2.9 Hz), 8.60 (dd, 1H, J 9.1, 2.9 Hz), 8.03 (d, 1H, J 7.9 Hz), 7.80-7.85 (m, 2H), 7.62-7.66 (m, 1H), 7.22 (d, 1H, J 9.1 Hz), 7.04 (d, 1H, J 2.8 Hz), 6.98 (dd, 1H, J 8.8, 2.8 Hz), 6.88 (d, 1H, J 8.8 Hz), 5.52 (dd, 1H, J 10.3, 2.0 Hz), 2.99-3.31 (m, 1H), 2.80-2.85 (m, 1H), 2.35-2.40 (m, 1H), 1.99-2.04 (m, 1H).

Example 90

6-[2-(2Aminophenyl)chroman-6-yloxy]-pyridin-3-ylamine

6-[2-(2-Aminophenyl)chroman-6-yloxy]-pyridin-3-ylamine was prepared as described for 5-amino-2-(2-phenylchroman-6-yloxy)pyridine in Example 26 using 100 mg 5-nitro-2-[2-(2-nitrophenyl)chroman-6-yloxy]pyridine (Example 89(d)) and 700 mg of Zn. $^1$H NMR (300 MHz, $d_6$-DMSO) δ: 7.51 (d, 1H, J 2.9 Hz), 7.15-7.18 (m, 1H), 7.05 (dd, 1H, J 8.6, 2.9 Hz), 6.98-7.00 (m, 1H), 6.77 (d, 1H, J 8.6 Hz), 6.73-6.75 (m, 2H), 6.66-6.71 (m, 2H), 6.56-6.61 (m, 1H), 5.11 (dd, 1H, J 10.4, 2.0 Hz), 5.01 (s, 2H), 4.99 (s, 2H), 2.94-2.99 (m, 1H), 2.66-2.74 (m, 1H), 2.06-2.13 (m, 1H), 1.88-1.95 (m, 1H).

Example 91

N-{6-[2-(2-Acetylaminophenyl)chroman-6-yloxy]pyridin-3-yl}acetamide

N-{6-[2-(2-Acetylaminophenyl)chroman-6-yloxy]pyridin-3-yl}acetamide was prepared as described for 5-N'-acetylamino-2-(2-phenylchroman-6-yloxy)pyridine in Example 27 starting from 6-[2-(2-aminophenyl)chroman-6-yloxy]-pyridin-3-ylamine (Example 90). $^1$H NMR (300 MHz, $d_6$-DMSO) δ: 10.02 (s, 1H), 9.44 (s, 1H), 8.27 (d, 1H, J 2.7 Hz), 8.00 (dd, 1H, J 8.8, 2.7 Hz), 7.49 (d, 1H, J 8.8 Hz), 7.25-7.38 (m, 3H), 6.92 (d, 1H, J 8.9 Hz), 6.88 (s, 1H), 6.83 (s, 2H), 5.22 (d, 1H, J 8.7 Hz), 2.90-2.99 (m, 1H), 2.72-2.79 (m, 1H), 2.12-2.18 (m, 1H), 2.04 (s, 6H), 1.86-1.94 (m, 1H).

Example 92

5-Nitro-2-[2-(3-nitrophenyl)chroman-6-yloxy]pyridine a) 6-Hydroxy-2-(3-nitrophenyl)chroman-4-one 6-Hydroxy-2-(3-nitrophenyl)chroman-4-one was prepared as described for 6-hydroxy-2-(3-fluorophenyl)chroman-4-one in Example 9(a). The product was recrystallised from ethanol. $^1$H NMR (300 MHz, $d_6$-DMSO) δ: 8.40 (s, 1H), 8.24 (dd, 1H, J 8.2, 2.3 Hz), 8.01 (d, 1H, J 7.9 Hz), 7.74 (t, 1H, J 15.9, 7.9 Hz), 7.13 (d, 1H, J 2.9 Hz), 7.07 (dd, 1H, J 8.8, 2.9 Hz), 7.00 (d, 1H, 8.8 Hz), 5.75 (dd, 1H, J 13.1, 2.9 Hz), 3.21 (dd, 1H, J 16.8, 13.1 Hz), 2.88 (dd, 1H, J 16.8, 2.9 Hz).

b) 2-(3-Nitrophenyl)chroman-4,6-diol 2-(3-Nitrophenyl)chroman-4,6-diol was prepared as described for 2-phenylchroman-4,6-diol in Example 8(a) starting from 6-hydroxy-2-(3-nitrophenyl)chroman-4-one. $^1$H NMR (400 MHz, $d_6$-DMSO) δ: 8.89 (br s, 1H), 8.29 (s, 1H), 8.20 (dd, 1H, J 8.2, 2.3Hz), 7.93 (d, 1H, J 7.9Hz), 7.71 (t, 1H, J 15.9, 7.9Hz), 6.89 (d, 1H, J 2.8 Hz), 6.66 (d, 1H, J 8.7 Hz), 6.57 (dd, 1H, J 8.7, 2.9 Hz), 5.47 (br s, 1H), 5.33 (d, 1H, J 10.7 Hz), 4.88-4.92 (m, 1H), 2.33-2.39 (m, 1H), 1.83-1.92 (m, 1H).

c) 2-(3-Nitrophenyl)chroman-6-ol 2-3-Nitrophenyl)chroman-6-ol was prepared as described for 2-(3-fluorophenyl)chroman-6-ol in Example 9(c) starting from 2-(3-nitrophenyl)chroman-4,6-diol. $^1$H NMR (300 MHz, $d_6$-DMSO) δ: 8.80 (s, 1H), 8.26 (s, 1H), 8.19 (dd, 1H, J 8.1, 2.3 Hz), 7.90 (d, 1H, J 7.9Hz), 7.70 (t, 1H, J 15.9, 7.9 Hz), 6.70 (d, 1H, J 8.4 Hz), 6.51-6.55 (m, 2H), 5.19 (dd, 1H, J 10.0, 2.0), 2.86-2.91 (m, 1H), 2.61-2.68 (m, 1H), 2.17-2.23 (m, 1H), 1.91-1.97 (m, 1H).

d) 5-Nitro-2-[2-(3-nitrophenyl)chroman-6-yloxy]pyridine

5-Nitro-2-[2-(3-nitrophenyl)chroman-6-yloxy]pyridine was prepared as described for 5-nitro-2-(2-phenylchroman-6-yloxy)pyridine in Example 1(b) starting from 2-(3-nitrophenyl)chroman-6-ol. $^1$H NMR (400 MHz, $d_6$-DMSO) δ: 9.04 (d, 1H, J 2.9 Hz), 8.60 (dd, 1H, J 9.0, 2.9 Hz), 8.32 (s, 1H), 8.23 (d, 1H, J 8.3 Hz), 7.95 (d, 1H, J 7.9 Hz), 7.74 (t, 1H, J 15.8, 7.9 Hz), 7.21 (d, 1H, J 9.0 Hz), 6.96-7.03 (m, 3H), 5.35 (d, 1H, J 8.7 Hz), 2.98-3.06 (m, 1H), 2.72-2.79 (m, 1H), 2.26-2.33 (m, 1H), 1.99-2.06 (m, 1H).

Example 93

6-[2-(3-Aminophenyl)chroman-6-yloxy]-pyridin-3-ylamine

6-[2-(3-Aminophenyl)chroman-6-yloxy]-pyridin-3-ylamine was prepared as described for 5-amino-2-(2-phenylchroman-6-yloxy)pyridine in Example 26 using 150 mg 5-nitro-2-[2-(3-nitrophenyl)chroman-6-yloxy]pyridine (Example 92(d)) and 997 mg of Zn. $^1$H NMR (300 MHz, $d_6$-DMSO) δ: 7.51 (d, 1H, J 2.8 Hz), 7.05 (dd, 1H, J 8.6, 2.8 Hz), 7.01 (t, 1H, J 15.4, 7.7 Hz), 6.70-6.78 (m, 3H), 6.68 (d, 1H, J 8.6 Hz), 6.63 (s, 1H), 6.54 (d, 1H, J 7.7 Hz), 6.50 (d, 1H, J 8.6 Hz), 5.06 (s, 2H), 4.98 (s, 2H), 4.90 (dd, 1H, J 10.0, 2.2 Hz), 2.85-2.96 (m, 1H), 2.62-2.74 (m, 1H), 2.05-2.11 (m, 1H), 1.89-1.95 (m, 1H).

Example 94

2-(4-Methoxyphenyl)-6-(5-nitropyridin-2-yloxy)chroman-4-ol a) 6-Hydroxy-2-(4-methoxyphenyl)chroman-4-one 6-Hydroxy-2-(4-methoxyphenyl)chroman-4-one was prepared as described for 6-hydroxy-2-(3-fluorophenyl)chroman-4-one in Example 9(a). The product was recrystallised from ethanol. $^1$H NMR (400 MHz, $d_6$-DMSO) δ: 9.40 (s, 1H), 7.45 (d, 2H, J 8.7 Hz), 7.11 (d, 1H, J 3.0 Hz), 7.02 (dd, 1H, J 8.9, 3.0 Hz), 6.97 (d, 2H, J 8.7 Hz), 6.93 (d, 1H, J 8.9 Hz), 5.47 (dd, 1H, J 13.1, 2.8 Hz), 3.77 (s, 3H), 3.19 (dd, 1H, J 16.8, 13.1 Hz), 2.72 (dd, 1H, J 16.8, 2.8 Hz).

b) 2-(4-methoxyphenyl)chroman-4,6-diol 2-(4-Methoxyphenyl)chroman-4,6-diol was prepared as described for 2-phenylchroman-4,6-diol in Example 8(a) starting from 6-hydroxy-2-(4-methoxyphenyl)chroman-4-one. $^1$H NMR (300 MHz, $d_6$-DMSO) δ: 8.78 (s, 1H), 7.35 (d, 2H, J 8.7 Hz), 6.94 (d, 2H, J 8.7 Hz), 6.88 (d, 1H, J 2.5 Hz), 6.56 (d, 1H, J 8.7 Hz), 6.52 (dd, 1H, J 8.7, 2.5 Hz), 5.37 (br s, 1H), 5.04 (d, 1H, J 10.9 Hz), 4.83-4.89 (m, 1H), 3.76 (s, 3H), 2.18-2.25 (m, 1H), 1.85-1.97 (m, 1H).

c) 2-(4-Methoxyphenyl)-6-(5-nitropyridin-2-yloxy)chroman-4-ol 2-(4-Methoxyphenyl)-6-(5-nitropyridin-2-yloxy)chroman-4-ol was prepared as described for 5-nitro-2-(2-phenylchroman-6-yloxy)pyridine in Example 1(b) starting from 2-(4-methoxyphenyl)chroman-4,6-diol. $^1$H NMR (400 MHz, d$_6$-DMSO) δ: 9.04 (d, 1H, J 2.9 Hz), 8.61 (dd, 1H, J 9.1, 2.9 Hz), 7.40 (d, 2H, J 8.7 Hz), 7.24 (d, 1H, J 2.8 Hz), 7.22 (d, 1H, J 9.1 Hz), 7.00 (dd, 1H, J 8.7, 2.8 Hz), 6.97 (d, 2H, J 8.7 Hz), 6.84 (d, 1H, J 8.7 Hz), 5.63 (d, 1H, J 6.4 Hz), 5.23 (d, 1H, J 10.8 Hz), 4.95-5.02 (m, 1H), 3.78 (s, 3H), 2.25-2.29 (m, 1H), 1.98-2.04 (m, 1H).

Example 95

6-(5-Aminopyridin-2-yloxy-2-(4-methoxyphenyl)chroman-4-ol 6-(5-Aminopyridin-2-yloxy)-2-(4-methoxyphenyl)chroman-4-ol was prepared as described for 5-amino-2-(2-phenylchroman-6-yloxy)pyridine in Example 26 using 105 mg 2-(4-methoxyphenyl)-6-(5-nitropyridin-2-yloxy)chroman-4-ol (Example 94(c)) and 348 mg of Zn. $^1$H NMR (400 MHz, d$_6$-DMSO) δ: 7.52 (d, 1H, J 3.0 Hz), 7.38 (d, 2H, J 8.8 Hz), 7.06 (dd, 1H, J 8.7, 3.0 Hz), 7.04 (d, 1H, J 2.9 Hz), 6.96 (d, 2H, J 8.8 Hz), 6.77 (dd, 1H, J 8.7, 2.9 Hz), 6.72 (d, 1H, J 8.7 Hz), 6.70 (d, 1H, J 8.6 Hz), 5.52 (d, 1H, J 6.6 Hz), 5.15 (d, 1H, J 10.7 Hz), 5.01 (s, 2H), 4.87-4.93 (m, 1H), 3.77 (s, 3H), 2.22-2.26 (m, 1H), 1.90-1.99 (m, 1H).

Example 96

N-{6-[4-Hydroxy-2-(4-methoxyphenyl)chroman-6-yloxy]pyridin-3-yl}Acetamide

N-{6-[4-Hydroxy-2-(4-methoxyphenyl)chroman-6-yloxy]pyridin-3-yl}-acetamide was prepared as described for 5-N'-acetylamino-2-(2-phenylchroman-6-yloxy)pyridine in Example 27 starting from 6-(5-aminopyridin-2-yloxy)-2-(4-methoxyphenyl)chroman-4-ol (Example 95). $^1$H NMR (400 MHz, d$_6$-DMSO) δ: 10.05 (s, 1H), 8.28 (d, 1H, J 2.7 Hz), 8.01 (dd, 1H, J 8.8, 2.7 Hz), 7.39 (d, 2H, J 8.7 Hz), 7.14 (d, 1H, J 2.7 Hz), 6.97 (d, 2H, J 8.7 Hz), 6.94 (d, 1H, J 8.8 Hz), 6.88 (dd, 1H, J 8.8, 2.7 Hz), 6.77 (d, 1H, J 8.8 Hz), 5.57 (d, 1H, J 6.5 Hz), 5.19 (d, 1H, J 10.6 Hz), 4.90-4.97 (m, 1H), 3.77 (s, 3H), 2.24-2.27 (m, 1H), 2.04 (s, 3H), 1.93-2.01 (m, 1H).

Example 97

2-(2-Methoxyphenyl)-6-(5-nitropyridin-2-yloxy)chroman-4-ol a) 6-Hydroxy-2-(2-methoxyphenyl)chroman-4-one

6-Hydroxy-2-(2-methoxyphenyl)chroman-4-one was prepared as described for 6-hydroxy-2-(3-fluorophenyl)chroman-4-one in Example 9(a). The product was recrystallised from ethanol. $^1$H NMR (400 MHz, d$_6$-DMSO) δ: 9.40 (s, 1H), 7.56 (dd, 1H, J 7.6, 1.6 Hz), 7.37 (dt, 1H, J 8.6, 7.0, 1.6 Hz), 7.12 (d, 1H, J 2.9 Hz), 7.07 (d, 1H, J 8.6 Hz), 7.03 (d, 1H, J 8.9 Hz), 7.02 (d, 1H, J 7.0 Hz), 6.95 (d, 1H, J 8.9 Hz), 5.70 (dd, 1H, J 13.3, 2.7 Hz), 3.82 (s, 3H), 3.09 (dd, 1H, J 16.8, 13.3 Hz), 2.71 (dd, 1H, J 16.8, 2.7 Hz).

b) 2-(2-methoxyphenyl)chroman-4,6-diol 2-(2-Methoxyphenyl)chroman-4,6-diol was prepared as described for 2-phenylchroman-4,6-diol in Example 8(a) starting from 6-hydroxy-2-(2-methoxyphenyl)-chroman-4-one. $^1$H NMR (300 MHz, d$_6$-DMSO) δ: 8.79 (s, 1H), 7.45 (dd, 1H, J 7.6, 1.6 Hz), 7.31 (dt, 1H, J 8.5, 7.3, 1.6 Hz), 7.04 (d, 1H, J 8.5 Hz), 6.99 (d, 1H, J 7.3 Hz), 6.88 (d, 1H, J 2.7 Hz), 6.59 (d, 1H, J 8.7 Hz), 6.54 (dd, 1H, J 8.7, 2.7 Hz), 5.38 (s, 1H), 5.34 (d, 1H, J 11.4 Hz), 4.80-4.88 (m, 1H), 3.81 (s, 3H), 2.24-2.28 (m, 1H), 1.74-1.86 (m, 1H).

c) 2-(2-Methoxyphenyl)-6-5-nitropyridin-2-yloxy)chroman-4-ol 2-(2-Methoxyphenyl)-6-(5-nitropyridin-2-yloxy)chroman-4-ol was prepared as described for 5-nitro-2-(2-phenylchroman-6-yloxy)pyridine in Example 1(b) starting from 2-(2-methoxyphenyl)chroman-4,6-diol. $^1$H NMR (400 MHz, d$_6$-DMSO) δ: 9.04 (d, 1H, J 2.9 Hz), 8.61 (dd, 1H, J 9.1, 2.9 Hz), 7.49 (dd, 1H, J 7.6, 1.7 Hz), 7.34 (dt, 1H, J 8.3, 7.5, 1.7 Hz), 7.24 (d, 1H, J 2.8 Hz), 7.22 (d, 1H, J 9.1 Hz), 7.07 (d, 1H, J 8.3 Hz), 7.03 (d, 1H, J 7.5 Hz), 7.01 (dd, 1H, J 8.7, 2.8 Hz), 6.88 (d, 1H, J 8.7 Hz), 5.62 (d, 1H, J 6.3 Hz), 5.52 (d, 1H, J 10.4 Hz), 4.93-4.99 (m, 1H), 3.84 (s, 3H), 2.30-2.35 (m, 1H), 1.85-1.94 (m, 1H).

Example 98

6-(5-Aminopyridin-2-yloxy)-2-(2-methoxyphenyl)chroman-4-ol 6-(5-Aminopyridin-2-yloxy)-2-(2-methoxyphenyl)chroman-4-ol was prepared as described for 5-amino-2-(2-phenylchroman-6-yloxy)pyridine in Example 26 using 79 mg 2-(2-methoxyphenyl)-6-(5-nitropyridin-2-yloxy)chroman-4-ol (Example 97(c)) and 262 mg of Zn. $^1$H NMR (400 MHz, d$_6$-DMSO) δ: 7.52 (d, 1H, J 2.9 Hz), 7.47 (dd, 1H, J 7.5, 1.6 Hz), 7.33 (dt, 1H, J 8.5, 7.4, 1.6 Hz), 7.06 (d, 1H, J 2.8 Hz), 7.03-7.05 (m, 2H), 7.01 (d, 1H, J 7.4 Hz), 6.79 (dd, 1H, J 8.6, 2.8 Hz), 6.75 (d, 1H, J 8.7 Hz), 6.71 (d, 1H, J 8.6 Hz), 5.52 (d, 1H, J 6.5 Hz), 5.44 (d, 1H, J 10.5 Hz), 5.01 (s, 2H), 4.86-4.92 (m, 1H), 3.83 (s, 3H), 2.27-2.32 (m, 1H), 1.80-1.88 (m, 1H).

Example 99

2-[2-(3-Methoxyphenyl)chroman-6-yloxy]-5-nitropyridine a) 6-Hydroxy-2-(3-methoxyphenyl)chroman-4-one

6-Hydroxy-2-(3-methoxyphenyl)chroman-4-one was prepared as described for 6-hydroxy-2-(3-fluorophenyl)chroman-4-one in Example 9(a). The product was recrystallised from ethanol. $^1$H NMR (400 MHz, d$_6$-DMSO) δ: 9.42 (s, 1H), 7.33 (t, 1H, J 15.8, 8.3 Hz), 7.12 (d, 1H, J 3.0 Hz), 7.10 (s, 1H), 7.09 (d, 1H, J 8.3 Hz), 7.04 (dd, 1H, J 8.8, 3.0 Hz), 6.96 (d, 1H, 8.8 Hz), 6.93 (dd, 1H, J 8.0, 2.5 Hz), 5.52 (dd, 1H, J 12.9, 2.9 Hz), 3.77 (s, 3H), 3.17 (dd, 1H, J 16.9, 12.9 Hz), 2.77 (dd, 1H, J 16.9, 2.9 Hz).

b) 2-(3-methoxyphenyl)chroman-4,6-diol 2-(3-Methoxyphenyl)chroman-4,6-diol was prepared as described for 2-phenylchroman-4,6-diol in Example 8(a) starting from 6-hydroxy-2-(3-methoxyphenyl)-chroman-4-one. $^1$H NMR (400 MHz, d$_6$-DMSO) δ: 8.82 (s, 1H), 7.31 (t, 1H, J 15.7, 7.9 Hz), 6.99-7.02 (m, 2H), 6.88-6.90 (m, 2H), 6.59 (d, 1H, J 8.7 Hz), 6.54 (dd, 1H, J 8.7, 2.8 Hz), 5.40 (d, 1H, J 7.0 Hz), 5.08 (d, 1H, J 11.5 Hz), 4.83-4.89 (m, 1H), 3.77 (s, 3H), 2.23-2.28 (m, 1H), 1.83-1.92 (m, 1H).

c) 2-(3-Methoxyphenyl)chroman-6-ol 2-(3-Methoxyphenyl)chroman-6-ol was prepared as described for 2-(3-fluorophenyl)chroman-6-ol in Example 9(c) starting from 2-(3-methoxyphenyl)chroman-4,6-diol. $^1$H NMR (300 MHz, $d_6$-DMSO) δ: 8.75 (s, 1H), 7.28 (t, 1H, J 15.7, 7.9 Hz), 6.96-6.99 (m, 2H), 6.87 (dd, 1H, J 7.9, 2.5 Hz), 6.63 (d, 1H, J 8.3 Hz), 6.52 (d, 1H, J 2.9 Hz), 6.48 (s, 1H), 4.95 (dd, 1H, J 9.8, 2.2 Hz), 3.75 (s, 3H), 2.82-2.89 (m, 1H), 2.57-2.66 (m, 1H), 2.06-2.13 (m, 1H), 1.89-1.97 (m, 1H).

d) 2-[2-(3-Methoxyphenyl)chroman-6-yloxy]-5-nitropyridine

2-[2-(3-Methoxyphenyl)chroman-6-yloxy]-5-nitropyridine was prepared as described for 5-nitro-2-(2-phenylchroman-6-yloxy)pyridine in Example 1(b) starting from 2-(3-methoxyphenyl)chroman-6-ol. $^1$H NMR (400 MHz, $d_6$-DMSO) δ: 9.04 (d, 1H, J 2.9Hz), 8.60 (dd, 1H, J 9.1, 2.9 Hz), 7.32 (t, 1H, J 15.7, 7.9 Hz), 7.20 (d, 1H, J 9.1 Hz), 7.03 (d, 1H, J 8.4 Hz), 7.01 (s, 1H), 7.00 (d, 1H, J 2.8 Hz), 6.96 (dd, 1H, J 8.7, 2.8 Hz), 6.92 (d, 1H, J 8.7 Hz), 6.90 (dd, 1H, J 8.4, 2.6 Hz), 5.12 (dd, 1H, J 10.0, 2.3 Hz), 3.77 (s, 3H), 2.93-2.97 (m, 1H), 2.71-2.77 (m, 1H), 2.15-2.20 (m, 1H), 1.99-2.05 (m, 1H).

Example 100

6-[2-(3-Methoxyphenyl)chroman-6-yloxy]pyridin-3-ylamine

6-[2-(3-Methoxyphenyl)chroman-6-yloxy]pyridin-3-ylamine was prepared as described for 5-amino-2-(2-phenylchroman-6-yloxy)pyridine in Example 26 using 300 mg 2-[2-(3-methoxyphenyl)chroman-6-yloxy]-5-nitropyridine (Example 99(d)) and 1.0 g of Zn. H NMR (400 MHz, $d_6$-DMSO) δ: 7.51 (d, 1H, J 3.0 Hz), 7.31 (t, 1H, J 15.8, 7.9 Hz), 7.04 (dd, 1H, J 8.7, 3.0 Hz), 6.99-7.02 (m, 1H), 6.99 (d, 1H, J 2.6 Hz), 6.90 (dd, 1H, J 8.9, 2.6 Hz), 6.79-6.81 (m, 1H), 6.72-6.74 (m, 2H), 6.69 (d, 1H, J 8.9 Hz), 5.06 (dd, 1H, J 9.9, 2.2 Hz), 4.50 (s, 2H), 3.77 (s, 3H), 2.88-2.95 (m, 1H), 2.66-2.71 (m, 1H), 2.12-2.17 (m, 1H), 1.94-2.00 (m, 1H).

Example 101

N-{6-[2-(3-Methoxyphenyl)chroman-6-yloxy]pyridin-3-yl}acetamide

N-{6-[2-(3-Methoxyphenyl)chroman-6-yloxy]pyridin-3-yl}acetamide was prepared as described for 5-N'-acetylamino-2-(2-phenylchroman-6-yloxy)pyridine in Example 27 starting from 6-[2-(3-Methoxyphenyl)chroman-6-yloxy]pyridin-3-ylamine (Example 100). $^1$H NMR (400 MHz, $d_6$-DMSO) δ: 10.04 (s, 1H), 8.27 (d, 1H, J 2.7 Hz), 8.01 (dd, 1H, J 8.9, 2.7 Hz), 7.32 (t, 1H, J 15.7, 7.8 Hz), 7.02 (d, 1H, J 8.8 Hz), 7.00 (d, 1H, J 2.5 Hz), 6.92 (d, 1H, J 8.9 Hz), 6.90 (dd, 1H, J 8.2, 2.5 Hz), 6.84-6.86 (m, 3H), 5.09 (dd, 1H, J 9.9, 2.1 Hz), 3.77 (s, 3H), 2.91-2.95 (m, 1H), 2.68-2.74 (m, 1H), 2.14-2.18 (m, 1H), 2.04 (s, 3H), 1.97-2.02 (m, 1H).

Example 102

2-(3-Methoxyphenyl)-6-(5-nitropyridin-2-yloxy)chroman-4-ol 2-(3-Methoxyphenyl)-6-(5-nitropyridin-2-yloxy)chroman-4-ol was prepared as described for 5-nitro-2-(2-phenylchroman-6-yloxy)pyridine in Example 1(b) starting from 2-(3-methoxyphenyl)chroman-4,6-diol (Example 99(b)). $^1$H NMR (400 MHz, $d_6$-DMSO) δ: 9.04 (d, 1H, J 2.9 Hz), 8.61 (dd, 1H, 9.1, 2.9 Hz), 7.34 (t, 1H, J 15.7, 7.8 Hz), 7.25 (d, 1H, J 2.4 Hz), 7.22 (d, 1H, J 9.1 Hz), 7.00-7.06 (m, 3H), 6.92 (dd, 1H, J 8.8, 2.4 Hz), 6.88 (d, 1H, J 8.8 Hz), 5.64 (d, 1H, J 6.4 Hz), 5.27 (d, 1H, J 10.7 Hz), 4.95-5.00 (m, 1H), 3.79 (s, 3H), 2.30-2.35 (m, 1H), 1.92-2.01 (m, 1H).

Example 103

6-(5-Aminopyridin-2-yloxy)-2-(3-methoxyphenyl)chroman-4-ol 6-(5-Aminopyridin-2-yloxy)2-(3-methoxyphenyl)chroman-4-ol was prepared as described for 5-amino-2-(2-phenylchroman-6-yloxy)pyridine in Example 26 using 138 mg 2-(3-methoxyphenyl)-6-(5-nitropyridin-2-yloxy)chroman-4-ol (Example 102) and 457 mg of Zn. $^1$H NMR (400 MHz, $d_6$-DMSO) δ: 7.52 (d, 1H, J 3.0 Hz), 7.32 (t, 1H, J 15.7, 7.8 Hz), 7.06 (dd, 1H, 8.7, 3.0 Hz), 7.01-7.04 (m, 3H), 6.91 (dd, 1H, J 8.6, 2.4 Hz), 6.78-6.80 (m, 1H), 6.76 (d, 1H, J 8.7 Hz), 6.71 (d, 1H, J 8.6 Hz), 5.54 (d, 1H, J 6.5 Hz), 5.19 (d, 1H, J 10.6 Hz), 5.01 (s, 2H), 4.88-4.94 (m, 1H), 3.78 (s, 3H), 2.27-2.32 (m, 1H), 1.87-1.96 (m, 1H).

Example 104

6-(2-Phenyl-2,3-dihydrobenzo[1,4]oxathiin-6-yloxy)pyridin-3-ylamine Hydrochloride 6-(2-Phenyl-2,3-dihydrobenzo[1,4]oxathiin-6-yloxy)pyridin-3-ylamine was prepared as described for 5-amino-2-(2-phenylchroman-6-yloxy)pyridine in Example 26 starting from 5-nitro-2-(2-phenyl-2,3-dihydrobenzo[1,4]oxathiin-6-yloxy)pyridine (Example 84). 6-(2-Phenyl-2,3-dihydrobenzo[1,4]oxathiin-6-yloxy)pyridin-3-ylamine was isolated as its dihydrochloride salt. $^1$H NMR (400 MHz, CDCl$_3$) δ: 8.20 (d, 1H, J 2.1 Hz), 7.87 (dd, 1H, J 8.9, 2.1 Hz), 7.41-7.44 (m, 4H), 7.37-7.40 (m, 1H), 6.98 (d, 1H, J 8.9 Hz), 6.97 (d, 1H, J 8.8 Hz), 6.93 (d, 1H, J 2.7 Hz), 6.80 (dd, 1H, J 8.8, 2.7 Hz), 5.20 (dd, 1H, J 9.6, 1.9 Hz), 3.30 (dd, 1H, 13.2, 9.6 Hz), 3.12 (dd, 1H, 13.2, 1.9 Hz).

Example 105

N-[6-(2-Phenyl-2,3-dihydrobenzo[1,4]oxathiin-6-yloxy)pyridin-3-yl]acetamide

N-[6-(2-Phenyl-2,3-dihydrobenzo[1,4]oxathiin-6-yloxy)pyridin-3-yl]acetamide was prepared as described for 5-N'-acetylamino-2-(2-phenylchroman-6-yloxy)-pyridine in Example 27 starting from 6-(2-phenyl-2,3-dihydrobenzo[1,4]oxathiin-6-yloxy)pyridin-3-ylamine. $^1$H NMR (400 MHz, CDCl$_3$) δ: 8.07-8.11 (m, 2H), 7.40-7.42 (m, 4H), 7.36-7.39 (m, 1H), 7.15 (br s, 1H), 6.94 (d, 1H, J 8.8 Hz), 6.90 (d, 1H, J 2.8 Hz), 6.88 (d, 1H, J 9.1 Hz), 6.78 (dd, 1H, J 8.8, 2.8 Hz), 5.17 (dd, 1H, J 9.6, 1.9 Hz), 3.28 (dd, 1H, 13.2, 9.6 Hz), 3.08 (dd, 1H, 13.2, 1.9 Hz), 2.19 (s, 3H).

What is claimed is:

1. A compound of formula (I):

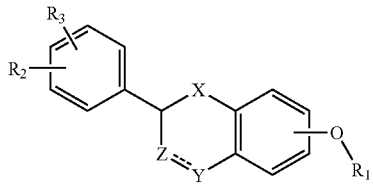

wherein
X is —O—;
Z is —CHR$_9$—;
Y is —CH$_2$—, —C(O)—, CH(OR$_{10}$)—, CH(NR$_{11}$R$_{12}$);
R$_1$ is

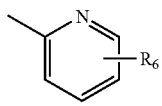

R$_2$ and R$_3$ are independently H, lower alkyl, lower alkoxy, —NO$_2$, halogen, —CF$_3$, —OH, —NHR$_8$ or —COOH,
R$_6$ is —NO$_2$, —NR$_{14}$R$_{19}$, —CF$_3$ or

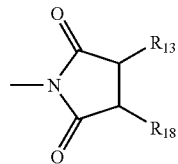

R$_8$ is H, alkylcarbonyl, or alkenylcarbonyl,
R$_9$ is H or lower alkyl,
R$_{10}$ is H, alkylsulfonyl, alkylcarbonyl, or alkenylcarbonyl;
R$_{11}$ and R$_{12}$ are independently H, lower alkyl, alkylcarbonyl, or alkenylcarbonyl,
R$_{13}$ and R$_{18}$ are independently H or —OR$_{20}$,
R$_{14}$ and R$_{19}$ are independently H, alkylcarbonyl, alkenylcarbonyl, alkylsulfonyl, C(S)NHR$_{17}$ or C(O)NHR$_{17}$,
R$_{17}$ is H or lower alkyl,
R$_{20}$ is H, alkylcarbonyl, or alkenylcarbonyl,
or a pharmaceutically acceptable salt thereof.

2. A compound according to claim 1, wherein formula (I) has the structure of formula (Ib)

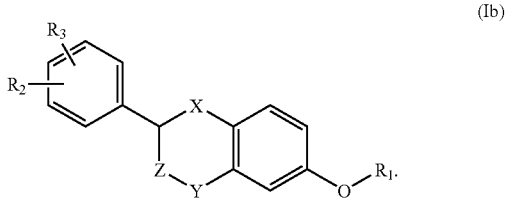

3. A compound according to claim 1, wherein X is O, and Z and Y are —CH$_2$—.

4. A compound according to claim 1, wherein X is O, Z is —CH$_2$ and Y is CHOH.

5. A compound according to claim 1, wherein R$_6$ is NO$_2$ or —NR$_{14}$R$_{19}$.

6. A compound according to claim 5, wherein R$_{14}$ and R$_{19}$ are independently H, alkylcarbonyl, alkenylcarbonyl, or alkylsulfonyl.

7. A compound according to claim 1, wherein R$_2$ and R$_3$ are independently H or halogen.

8. A compound according to claim 7, wherein halogen is fluorine.

9. A pharmaceutical composition comprising a compound of claim 1 together with a pharmaceutically acceptable carrier.

* * * * *

UNITED STATES PATENT AND TRADEMARK OFFICE
CERTIFICATE OF CORRECTION

PATENT NO. : 7,425,568 B2  Page 1 of 1
APPLICATION NO. : 10/482396
DATED : September 16, 2008
INVENTOR(S) : Tuula Koskelainen et al.

It is certified that error appears in the above-identified patent and that said Letters Patent is hereby corrected as shown below:

In Claim 1, col. 67, line 11, the line between Z and Y in formula I should be deleted.

Formula I should read -- 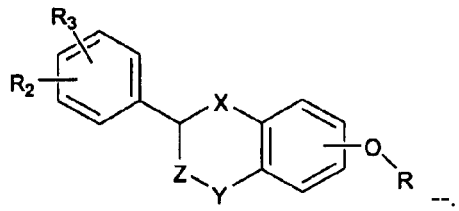 --.

Signed and Sealed this

Eleventh Day of November, 2008

JON W. DUDAS
*Director of the United States Patent and Trademark Office*